(12) United States Patent
Van Der Boom et al.

(10) Patent No.: US 11,053,434 B2
(45) Date of Patent: Jul. 6, 2021

(54) METHODS OF PREPARING MULTILAYERED ELECTROCHROMIC SYSTEMS

(71) Applicant: YEDA RESEARCH AND DEVELOPMENT CO. LTD., Rehovot (IL)

(72) Inventors: Milko E. Van Der Boom, Rishon Lezion (IL); Michal Lahav, Rehovot (IL); Neta Elool Dov, Rehovot (IL)

(73) Assignee: YEDA RESEARCH AND DEVELOPMENT CO. LTD., Rehovot (IL)

( * ) Notice: Subject to any disclaimer, the term of this patent is extended or adjusted under 35 U.S.C. 154(b) by 297 days.

(21) Appl. No.: 15/758,344

(22) PCT Filed: Sep. 8, 2016

(86) PCT No.: PCT/IL2016/051005
§ 371 (c)(1),
(2) Date: Mar. 8, 2018

(87) PCT Pub. No.: WO2017/042818
PCT Pub. Date: Mar. 16, 2017

(65) Prior Publication Data
US 2019/0023981 A1      Jan. 24, 2019

Related U.S. Application Data

(60) Provisional application No. 62/215,229, filed on Sep. 8, 2015.

(51) Int. Cl.
*G02F 1/1516*      (2019.01)
*B05D 5/06*      (2006.01)
(Continued)

(52) U.S. Cl.
CPC ............... *C09K 9/02* (2013.01); *B05D 1/005* (2013.01); *B05D 5/06* (2013.01); *B05D 7/51* (2013.01);
(Continued)

(58) Field of Classification Search
CPC .. B05D 1/005; B05D 7/51; B05D 5/06; G02F 1/1516; G02F 1/1523; C09K 9/02;
(Continued)

(56) References Cited

U.S. PATENT DOCUMENTS 4,267,212 A  *  5/1981  Sakawaki .............. G03F 7/162
                                                        427/240
5,252,354 A      10/1993  Cronin et al.
(Continued)

FOREIGN PATENT DOCUMENTS

WO      WO 2010/011407 A2      1/2010
WO      WO-2010069797 A1 *  6/2010  .............. C09K 9/02
(Continued)

OTHER PUBLICATIONS

Choudhury, J.; Kaminker, R.; Motiei, L.; Ruiter, G. de; Morozov, M.; Lupo, F.; Gulino, A.; Boom, M. E. Linear vs Exponential Formation of Molecular-Based Assemblies. Journal of the American Chemical Society 2010, 132 (27), 9295-9297. (Year: 2010).*
(Continued)

*Primary Examiner* — William P Fletcher, III
(74) *Attorney, Agent, or Firm* — Mark S. Cohen; Pearl Cohen Zedek Latzer Baratz LLP

(57) ABSTRACT

The invention is directed to methods for making an EC material comprising providing a substrate, applying at least one metal linker to the substrate, applying at least one metal-coordinated organic complex to form a layer, washing the layer, drying the layer, and repeating the applying steps to obtain a multiple layer EC material. The invention is
(Continued)

further directed to EC materials made by the methods of this invention.

36 Claims, 51 Drawing Sheets

(51) Int. Cl.
    *B05D 1/00*     (2006.01)
    *B05D 7/00*     (2006.01)
    *C09K 9/02*     (2006.01)
    *C07D 213/22*     (2006.01)
    *C07F 15/02*     (2006.01)
    *C09D 5/29*     (2006.01)

(52) U.S. Cl.
    CPC .......... *C07D 213/22* (2013.01); *C07F 15/025* (2013.01); *C09D 5/29* (2013.01); *G02F 1/1516* (2019.01); *C09K 2211/1029* (2013.01); *C09K 2211/185* (2013.01); *C09K 2211/187* (2013.01)

(58) Field of Classification Search
    CPC ...... C09K 2211/1029; C09K 2211/185; C09K 2211/187; C07D 213/22; C07F 15/025; C09D 5/29
    USPC ......................................................... 427/240
    See application file for complete search history.

(56) References Cited

U.S. PATENT DOCUMENTS

| | | | | |
|---|---|---|---|---|
| 8,722,879 | B2* | 5/2014 | Van Der Boom ... | H01G 9/2018 540/145 |
| 2013/0148413 | A1* | 6/2013 | Van Der Boom ...... | G11C 11/54 365/151 |
| 2014/0049923 | A1 | 2/2014 | Ma et al. | |
| 2014/0063584 | A1 | 3/2014 | Shi | |
| 2015/0007371 | A1 | 1/2015 | Van Der Boom et al. | |
| 2015/0303390 | A1* | 10/2015 | Van Der Boom .......................... | H01L 51/0098 428/426 |
| 2016/0293860 | A1* | 10/2016 | Van Der Boom ..... | B82Y 10/00 |

FOREIGN PATENT DOCUMENTS

| | | |
|---|---|---|
| WO | WO 2011/141913 A1 | 11/2011 |
| WO | WO 2014/061018 A2 | 4/2014 |
| WO | WO 2015/075714 A1 | 5/2015 |

OTHER PUBLICATIONS

Kaminker, R.; Motiei, L.; Gulino, A.; Fragalà Ignazio; Shimon, L. J.; Evmenenko, G.; Dutta, P.; Iron, M. A.; van der Boom, M. E. Stepwise Assembly of Coordination-Based Metal-Organic Networks. Journal of the American Chemical Society 2010, 132 (41), 14554-14561. (Year: 2010).*
Motiei, L.; Kaminker, R.; Sassi, M.; van der Boom, M. E. Molecule and Electron Transfer through Coordination-Based Molecular Assemblies. Journal of the American Chemical Society 2011, 133 (36), 14264-14266. (Year: 2011).*
Motiei, L.; Sassi, M.; Kaminker, R.; Evmenenko, G.; Dutta, P.; Iron, M. A.; van der Boom, M. E. Synergism in Multicomponent Self-Propagating Molecular Assemblies. Langmuir 2011, 27 (4), 1319-1325. (Year: 2011).*
Shinomiya, T.; Ozawa, H.; Mutoh, Y.; Haga, M.-aki. A Redox-Active Porous Coordination Network Film Based on a Ru Complex as a Building Block on an ITO Electrode. Dalton Transactions 2013, 42 (45), 16166. (Year: 2013).*
Addou et al. "Influence of hydroxyls on Pd Atom mobility and clustering on rutile TiO2 (011)-2×1" ACS nano. May 13, 2014;8(6):6321-33.
Altman et al. "Molecular assembly of a 3D-ordered multilayer" Journal of the American Chemical Society. Mar. 26, 2008;130(15):5040-1.
Altman et al. "Controlling structure from the bottom-up: Structural and optical properties of layer-by-layer assembled palladium coordination-based multilayers" Journal of the American Chemical Society. Jun. 7, 2006;128(22):7374-82.
Ariga et al. "Layer-by-layer assembly as a versatile bottom-up nanofabrication technique for exploratory research and realistic application" Physical Chemistry Chemical Physics. 2007;9(19):2319-40.
Choi et al. "Flexible electrochromic films based on CVD-graphene electrodes" Nanotechnology, Sep. 9, 2014;25(39):395702.
De Ruiter et al. "Composite molecular assemblies: Nanoscaie structural control and spectroelectrochemical diversity" Journal of the American Chemical Society. Oct. 25, 2013;135(44):16533-44.
Gillaspie et al. "Metal-oxide films for electrochromic applications: present technology and future directions" Journal of Materials Chemistry. 2010;20(43):9585-92.
Higuchi et al. "Electrochemical functions of metallosupramolecular nanomaterials" The Chemical Record. Jan. 1, 2007;7(4):203-9.
International Search Report for PCT Application No. PCT/IL2016/051005 dated Nov. 22, 2016.
Kim et al. "Electrical, optical, and structural properties of indium-tin-oxide thin films for organic light-emitting devices" Journal of Applied Physics. Dec. 1, 1999;86(11):6451-61.
Kwak et al. "Comparison of transparent conductive indium tin oxide, titanium-doped indium oxide, and fluorine-doped tin oxide films for dye-sensitized solar cell application" Journal of Electrical Engineering and Technology. 2011;6(5):684-7.
Layani et al. "Nanostructured electrochromic films by inkjet printing on large area and flexible transparent silver electrodes" Nanoscale. 2014;6(9):4572-6.
Lian et al. "Flexible electrochromic devices based on optoelectronically active polynorbornene layer and ultratransparent graphene electrodes" Macromolecules. Nov. 29, 2011;44(24):9550-5.
Liaw et al. "Novel organosoluble poly (pyridine—imide) with pendent pyrene group: Synthesis, thermal, optical, electrochemical, electrochromic, and protonation characterization" Macromolecules. May 15, 2007;40(10):3568-74.
Luo et al. "Rational Design, Synthesis, and Optical Properties of Film-Forming, Near-Infrared Absorbing, and Fluorescent Chromophores with Multidonors and Large Heterocyclic Acceptors" Chemistry—A European Journal. Sep. 7, 2009;15(35):8902-8.
Motiei et al. "Self-propagating assembly of a molecular-based multilayer" Journal of the American Chemical Society, Jun. 24, 2008;130(28):8913-5.
Sato et al. "Electrochromic properties of spin-coated nickel oxide films" Solid State Ionics. Dec. 1, 1998;113:443-7.
Shankar et al. "Coordination-based molecular assemblies as electrochromic materials: ultra-high switching stability and coloration efficiencies" Journal of the American Chemical Society, Mar. 20, 2015;137(12):4050-3.
Sharma et al. FTIR investigations of tungsten oxide electrochromic films derived from organically modified peroxotungstic acid precursors. Thin Solid Films. Dec. 17, 2001;401(1-2):45-51.
Shimizu et al. Electrochromic properties of spin-coated V2O5 thin films. Solid State Ionics. Jul. 1, 1992;53:490-5.
Shukla et al. "Electrochemical addressing of the optical properties of a monolayer on a transparent conducting substrate" Angewandte Chemie International Edition, May 20, 2005;44(21):3237-40.
Spielbauer et al. "Adsorption of palladium-ammino-aquo complexes on. gamma.-alumina and silica" Langmuir. Feb. 1993;9(2):460-6.
Van Deelen et al. "Transparent conducting materials: overview and recent results" In Thin Film Solar Technology IV Oct. 10, 2012 (vol. 8470, p. 84700P). International Society for Optics and Photonics.
Yu et al. "Side-chain engineering of green color electrochromic polymer materials: toward adaptive camouflage application" Journal of Materials Chemistry C. 2016;4(12):2269-73.

(56) References Cited

OTHER PUBLICATIONS

Supplementary European Search Report for European Application No. 16843847.1 dated Apr. 2, 2019.

* cited by examiner

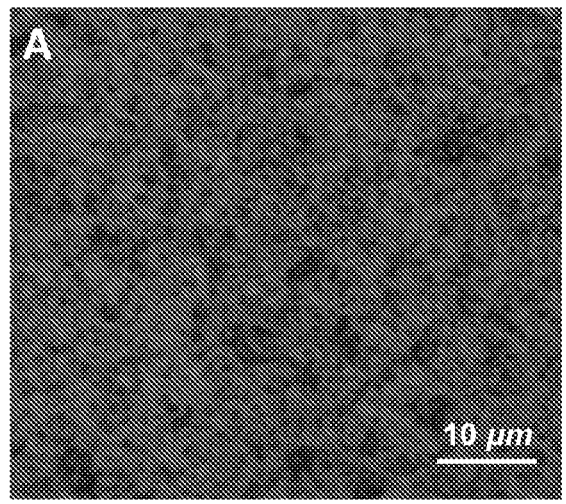
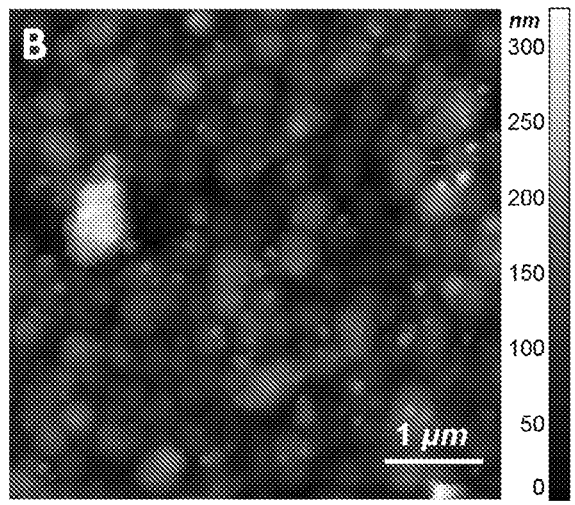
Figure 10A  Figure 10B
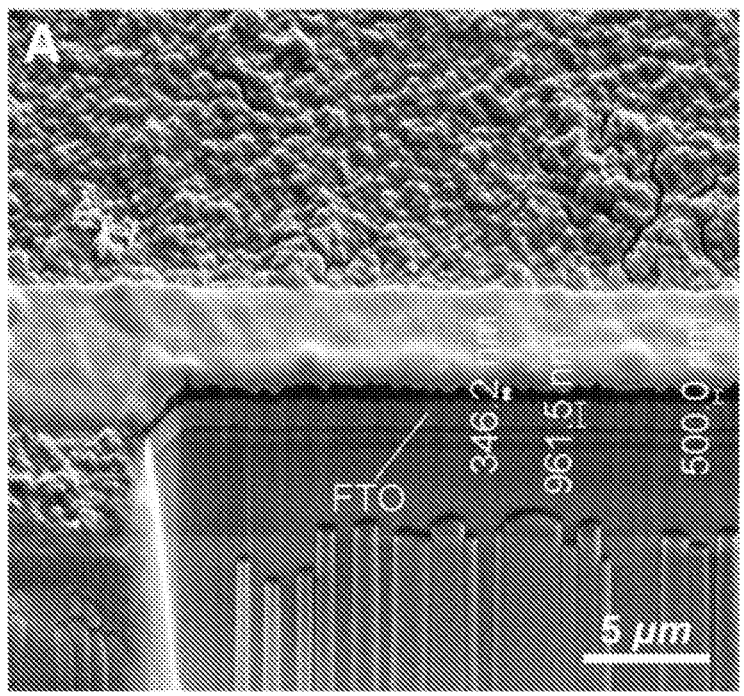
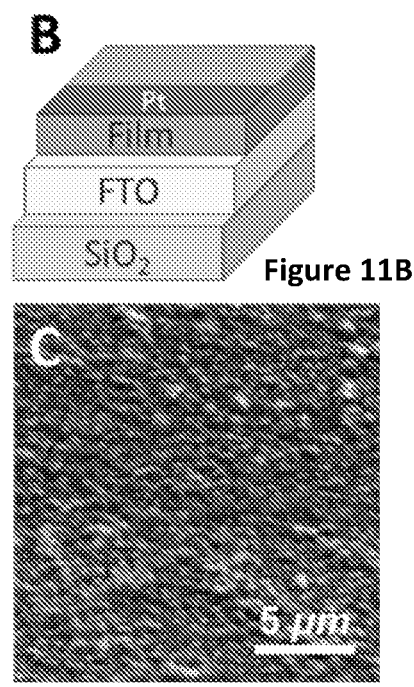
Figure 11A  Figure 11C Oxidation / Reduction

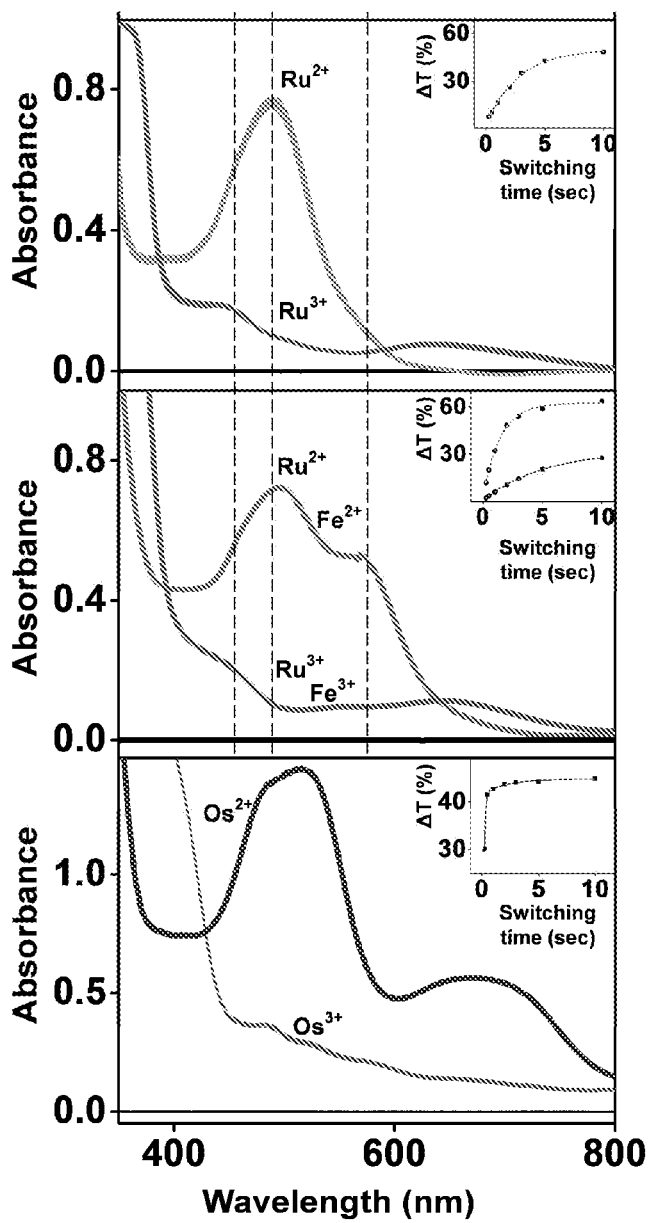
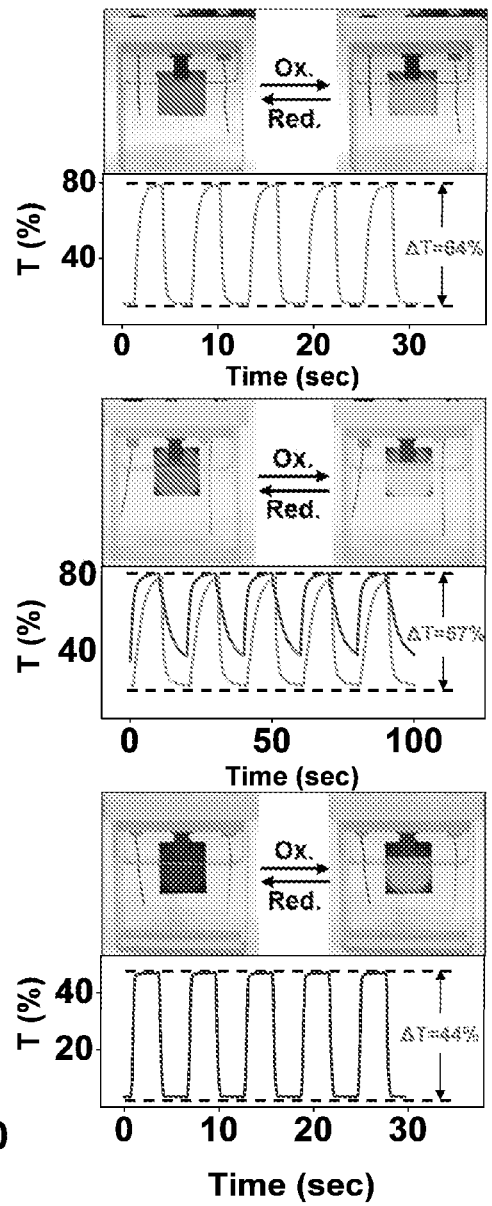
Figure 50A(cont.)
Figure 50B(cont.)

METHODS OF PREPARING MULTILAYERED ELECTROCHROMIC SYSTEMS

CROSS-REFERENCE TO RELATED APPLICATIONS

This application is a National Phase Applications of PCT International Application No. PCT/IL2016/051005, International Filing Date Sep. 8, 2016, claiming priority of US Provisional Patent Application(s) No(s). 62/215,229, filed Sep. 8, 2015, which are hereby incorporated by reference.

FIELD OF THE INVENTION

The invention encompasses processes for preparing a multilayered electrochromic film on transparent conductor using a combination of layer to layer coordination interactions and various deposition techniques.

BACKGROUND OF THE INVENTION

Electrochromic (EC) materials have distinct ability to alter their optical transparency in response to application of voltage. This property is particularly useful in smart windows, electrochromic windows, smart mirrors, optical filters, frequency doubling devices, spatial light modulators, pulse shapers, displays, signs, plastic electronics, lenses, sensors, and numerous other devices.

An interesting class of EC materials is metal-coordinated organic complexes where a metal ion is coordinately bonded to an organic molecule (a ligand). In order to obtain high-performance films of EC materials, the materials should be coated on a conducting, transparent substrate in a uniform manner. Film composition, film thickness, film density and film uniformity are properties that can greatly affect the EC performance of the material film. Such properties are important for various applications. EC applications include electronic displays systems such as color filter displays, monitors, TVs. Optoelectronics systems such as optical switches for optical telecommunication and optical/laser systems (e.g. for machining, medical treatments, army/military/space), construction materials products such as smart windows and light filtering windows, and products for the auto industry such as tintable reflective surfaces (e.g. car mirrors).

In view of the promising EC properties of metal-coordinated organic complexes, there exist a need to find a process for preparing high-performance EC materials and films comprising such complexes.

SUMMARY OF THE INVENTION

One embodiment of the invention encompasses a method for making an EC material comprising providing a substrate, applying at least one metal linker, applying at least one metal-coordinated organic complex to form a layer, washing the layer, drying the layer, and repeating the applying steps to obtain a multiple layer EC material.

In one embodiment, the metal-organic complex comprises at least one functional group, said functional group capable of binding to said metal linker. In one embodiment, the binding comprises a coordination bond between said functional group and said metal linker. In one embodiment, the metal complex is a polypyridyl complex.

In one embodiment, the applying steps comprise deposition techniques such as roll-to-roll, spin coating, dip coating, spray coating, physical vapor deposition (PVD), chemical vapor deposition (CVD) or combinations thereof. In one embodiment, the polypyridyl complex comprises one or more isomers of the same compound. In one embodiment, the polypyridyl complex comprises any mixture of isomers of the same compound. In one embodiment, the isomers are enantiomers. In one embodiment, the polypyridyl complex comprises one or two enantiomers of the same compound. In one embodiment, the polypyridyl complex comprises a mixture of said one or two enantiomers. In one embodiment, the enantiomer mixture is a racemic mixture. In one embodiment, the applying step(s) comprise spin coating.

According to this aspect and in one embodiment, this invention encompasses a method for making an EC material, the method comprising providing a substrate, applying at least one metal linker by spin coating, applying at least one polypyridyl complex by spin coating to form a layer, washing the layer, drying the layer, and repeating the applying steps to obtain a multiple layer EC material. In another embodiment of the invention the spin coating step to apply the metal linker has a first spin rate and a first spin time. In yet another embodiment of the invention the first spin rate is from about 100 to about 2000 rpm. In one embodiment of the invention the first spin time is from about 0.3 sec to about 60 sec. In another embodiment of the invention the spin coating step to apply the metal linker has a second spin rate and a second spin time. In one embodiment of the invention the second spin rate is from about 200 to about 3000 rpm. In one embodiment of the invention the second spin time is from about 1 second to about 120 seconds.

In one embodiment of the invention the washing solvent is selected from the group consisting of THF, alcohols, ethers, esters, halogenated solvents, hydrocarbons, and ketones. In one embodiment of the invention both applying steps are repeated to obtain from about 1 to about 80 layers.

In one embodiment of the invention the substrate is selected from the group consisting of ITO coated polyethylene terephthalate, ITO coated glass, and FTO coated glass. In one embodiment of the invention the metal linker is selected from the group consisting of Zn, Os, Ru, Fe, Pt, Pd, Ni, Ir, Rh, Co, Cu, Re, Tc, Mn, V, Nb, Ta, Hf, Zr, Cr, Mo, W, Ti, Sc, Ag, Au, and Y.

In one embodiment of the invention, the polypyridyl complex is represented by Formula I:

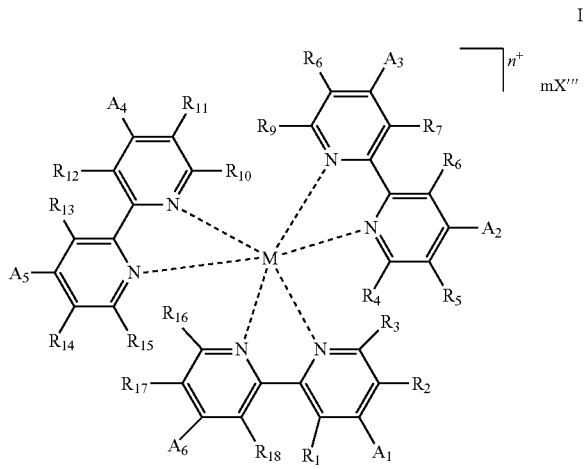

wherein

M is a transition metal selected from Mn, Fe, Co, Ni, Cu, Zn, Ti, C, Cr, Rh, Ru, Os or Ir;

n is the formal oxidation state of the transition metal, wherein n is 0-6;

X is a counter ion;

m is a number ranging from 0 to 6;

$R_1$ to $R_{18}$ each independently is selected from H, halogen, —OH, —$N_3$, —$NO_2$, —CN, —N($R_{20}$)$_2$, —CON($R_{20}$)$_2$, —COO$R_{20}$, —S$R_{20}$, —$SO_3H$, —CH=CH-pyridyl, —($C_1$-$C_{10}$)alkyl, —($C_2$-$C_{10}$)alkenyl, —($C_2$-$C_{10}$)alkynyl, —($C_1$-$C_{10}$)alkoxy, cycloalkyl, heterocycloalkyl, aryl, heteroaryl, protected carboxyl, or protected amino, wherein the ($C_1$-$C_{10}$)alkyl, ($C_2$-$C_{10}$)alkenyl, ($C_2$-$C_{10}$)alkynyl, cycloalkyl, heterocycloalkyl, aryl, or heteroaryl may optionally be substituted with halogen, —O$R_{20}$, —CO$R_{20}$, —COO$R_{20}$, —OCOO$R_{20}$, —OCON($R_{20}$)$_2$, —($C_1$-$C_8$)alkylene-COO$R_{20}$, —N($R_{20}$)$_2$, —$NO_2$, —S$R_{20}$, —($C_1$-$C_8$)alkyl, —O—($C_1$-$C_8$)alkyl, —CON($R_{20}$)$_2$, or —$SO_3H$;

$A_1$ to $A_6$ each independently is a group of Formula III, i.e., a pyridine or pyridine derivative moiety, or of Formula IV, i.e., pyrimidine or pyrimidine derivative moiety, linked to the ring structure of the complex of general Formula I via $R_{19}$

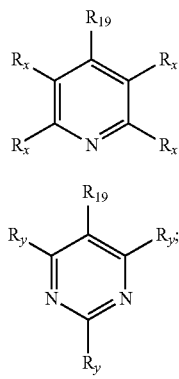

$R_{19}$ each independently is selected from a covalent bond, C—C, C=C, C≡C, N=N, C=N, N=C, C—N, N—C, —COO—, —CONH—, —CON(OH)—, —N$R_{20}$—, —Si($R_{20}$)$_2$—, an alkylene optionally interrupted by one or more heteroatoms selected from O, S, or N, phenylene, biphenylene, a peptide moiety consisting of 3 to 5 amino acid residues,

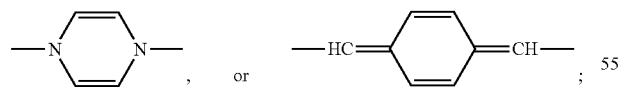

$R_x$ and $R_y$ each independently is selected from H, halogen, —OH, —$N_3$, —$NO_2$, —CN, —N($R_{20}$)$_2$, —CON($R_{20}$)$_2$, —COO$R_{20}$, —S$R_{20}$, —$SO_3H$, —CH=CH-pyridyl, —($C_1$-$C_{10}$)alkyl, —($C_2$-$C_{10}$)alkenyl, —($C_2$-$C_{10}$)alkynyl, —($C_1$-$C_{10}$)alkoxy, cycloalkyl, heterocycloalkyl, aryl, heteroaryl, protected carboxyl, or protected amino, wherein the ($C_1$-$C_{10}$)alkyl, ($C_2$-$C_{10}$)alkenyl, ($C_2$-$C_{10}$)alkynyl, cycloalkyl, heterocycloalkyl, aryl, or heteroaryl may optionally be substituted with halogen, —O$R_{20}$, —CO$R_{20}$, —COO$R_{20}$, —OCOO$R_{20}$, —OCON($R_{20}$)$_2$, ($C_1$-$C_8$)alkylene-COO$R_{20}$, —CN, —N($R_{20}$)$_2$, —$NO_2$, —S$R_{20}$, —O—($C_1$-$C_8$)alkyl, —CON($R_{20}$)$_2$, or —$SO_3H$; and $R_{20}$ each independently is H, ($C_1$-$C_6$)alkyl, or aryl.

In another embodiment of the invention, the polypyridyl complex is represented by Formula II:

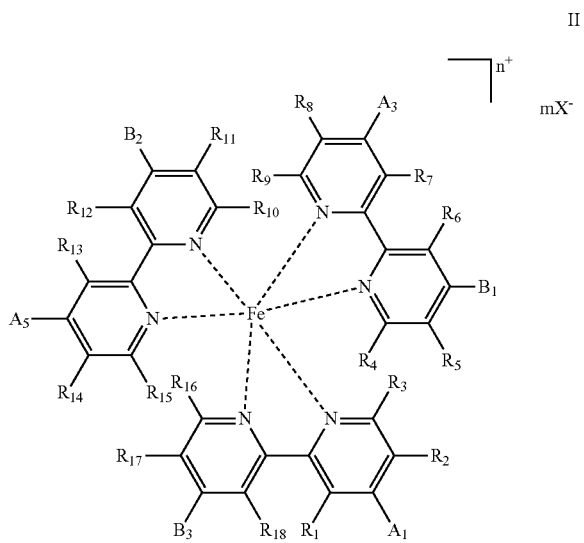

wherein n is the formal oxidation state of Fe, wherein n is 0-6;

X is a counter ion;

m is a number ranging from 0 to 6;

$R_1$ to $R_{18}$ each independently is selected from H, halogen, —OH, —$N_3$, —$NO_2$, —CN, —N($R_{20}$)$_2$, —CON($R_{20}$)$_2$, —COO$R_{20}$, —S$R_{20}$, —$SO_3H$, —CH=CH-pyridyl, —($C_1$-$C_{10}$)alkyl, —($C_2$-$C_{10}$)alkenyl, —($C_2$-$C_{10}$)alkynyl, —($C_1$-$C_{10}$)alkoxy, cycloalkyl, heterocycloalkyl, aryl, heteroaryl, protected carboxyl, or protected amino, wherein the ($C_1$-$C_{10}$)alkyl, ($C_2$-$C_{10}$)alkenyl, ($C_2$-$C_{10}$)alkynyl, cycloalkyl, heterocycloalkyl, aryl, or heteroaryl may optionally be substituted with halogen, —O$R_{20}$, —CO$R_{20}$, —COO$R_{20}$, —OCOO$R_{20}$, —OCON($R_{20}$)$_2$, —($C_1$-$C_8$)alkylene-COO$R_{20}$, —CN, —N($R_{20}$)$_2$, —$NO_2$, —S$R_{20}$, —($C_1$-$C_8$)alkyl, —O—($C_1$-$C_8$)alkyl, —CON($R_{20}$)$_2$, or —$SO_3H$;

$A_1$, $A_3$, and $A_5$ each independently is a group of Formula III, i.e., a pyridine or pyridine derivative moiety, or of Formula IV, i.e., pyrimidine or pyrimidine derivative moiety, linked to the ring structure of the complex of general Formula II via $R_{19}$

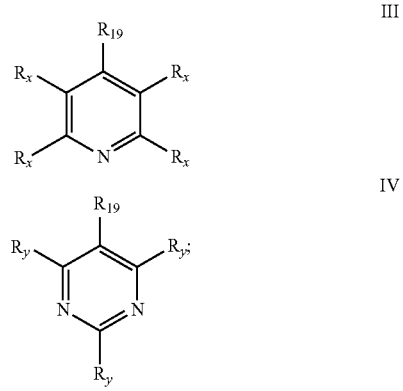

$R_{19}$ each independently is selected from a covalent bond, C—C, cis/tran C=C, C≡C, N=N, C=N, N=C, C—N, N—C, —COO—, —CONH—, —CON(OH)—, —NR$_{20}$—, —Si(R$_{20}$)$_2$—, an alkylene optionally interrupted by one or more heteroatoms selected from O, S, or N, phenylene, biphenylene, a peptide moiety consisting of 3 to 5 amino acid residues,

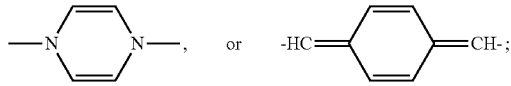

$R_x$ and $R_y$ each independently is selected from H, halogen, —OH, —N$_3$, —NO$_2$, —CN, —N(R$_{20}$)$_2$, —CON(R$_{20}$)$_2$, —COOR$_{20}$, —SR$_{20}$, —SO$_3$H, —CH=CH-pyridyl, —(C$_1$-C$_{10}$)alkyl, —(C$_2$-C$_{10}$)alkenyl, —(C$_2$-C$_{10}$)alkynyl, —(C$_1$-C$_{10}$)alkoxy, cycloalkyl, heterocycloalkyl, aryl, heteroaryl, protected carboxyl, or protected amino, wherein the (C$_1$-C$_{10}$)alkyl, (C$_2$-C$_{10}$)alkenyl, (C$_2$-C$_{10}$)alkynyl, cycloalkyl, heterocycloalkyl, aryl, or heteroaryl may optionally be substituted with halogen, —OR$_{20}$, —COR$_{20}$, —COOR$_{20}$, —OCOOR$_{20}$, —OCON(R$_{20}$)$_2$, —(C$_1$-C$_8$)alkylene-COOR$_{20}$, —CN, —N(R$_{20}$)$_2$, —NO$_2$, —SR$_{20}$, —(C$_1$-C$_8$)alkyl, —O—(C$_1$-C$_8$)alkyl, —CON(R$_{20}$)$_2$, or —SO$_3$H;

$B_1$ to $B_3$ each independently is selected from H, halogen, —OH, —N$_3$, —NO$_2$, —CN, —N(R$_{20}$)$_2$, —CON(R$_{20}$)$_2$, —COOR$_{20}$, —SR$_{20}$, —SO$_3$H, —CH=CH-pyridyl, —(C$_1$-C$_{10}$)alkyl, —(C$_2$-C$_{10}$)alkenyl, —(C$_2$-C$_{10}$)alkynyl, —(C$_1$-C$_{10}$)alkoxy, cycloalkyl, heterocycloalkyl, aryl, heteroaryl, protected carboxyl, or protected amino, wherein the (C$_1$-C$_{10}$)alkyl, (C$_2$-C$_{10}$)alkenyl, (C$_2$-C$_{10}$)alkynyl, cycloalkyl, heterocycloalkyl, aryl, or heteroaryl may optionally be substituted with halogen, —OR$_{20}$, —COR$_{20}$, —COOR$_{20}$, —OCOOR$_{20}$, —OCON(R$_{20}$)$_2$, —(C$_1$-C$_8$)alkylene-COOR$_{20}$, —CN, —N(R$_{20}$)$_2$, —NO$_2$, —SR$_{20}$, —(C$_1$-C$_8$)alkyl, —O—(C$_1$-C$_8$)alkyl, —CON(R$_{20}$)$_2$, or SO$_3$H; and $R_{20}$ each independently is H, (C$_1$-C$_6$)alkyl, or aryl.

In yet another embodiment of the invention, the pyridyl complex is represented by Formulas 1 or 2, with double bonds (1DB/2DB) single bonds (1SB/2SB) and triple bonds (1TB/2TB) as shown below:

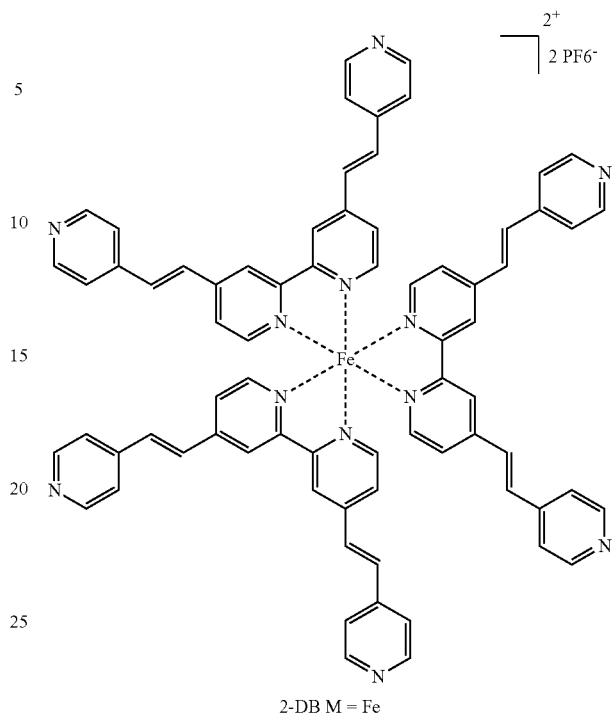

2-DB M = Fe

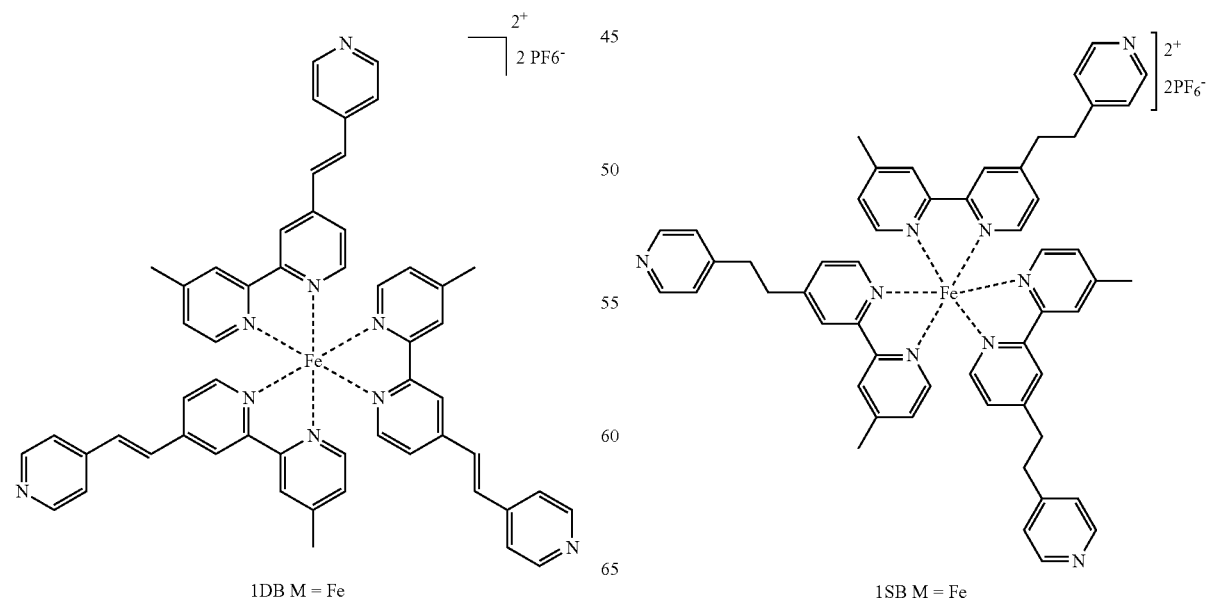

1DB M = Fe

1SB M = Fe

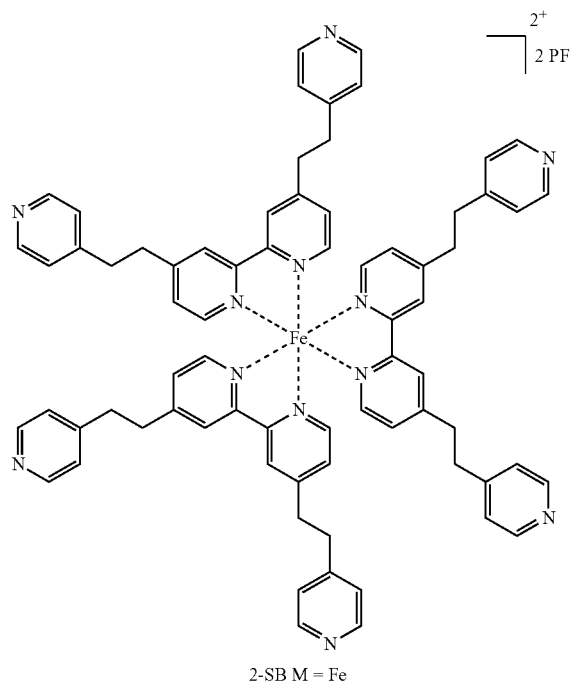

2-SB M = Fe

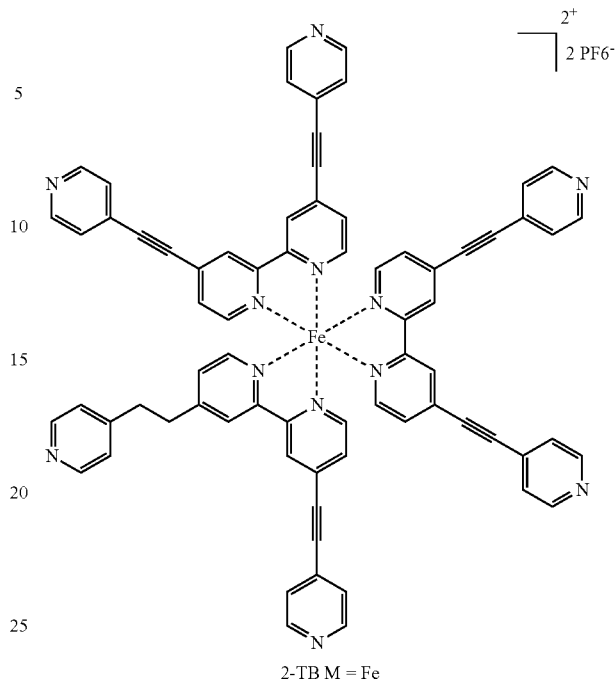

2-TB M = Fe

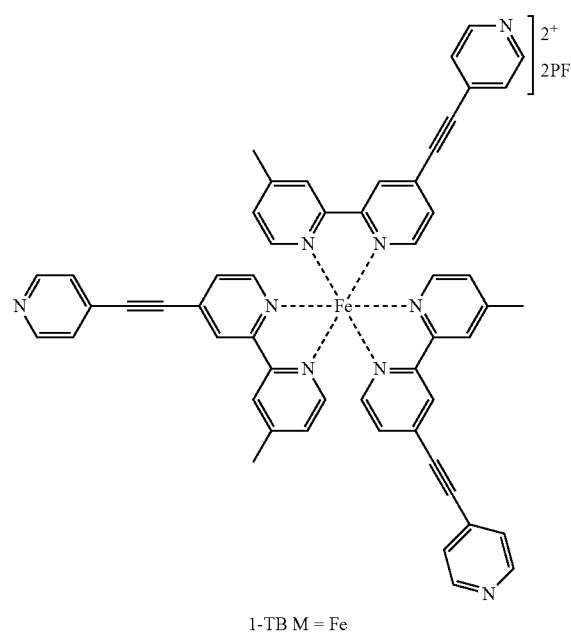

1-TB M = Fe

In the embodiments shown above, the charge on the counter ion is ($X^{1-}$). In other embodiments, other counter ions may be used with higher negative charge such as $X^{2-}$, $X^{3-}$, $X^{4-}$.

One embodiment of the invention encompasses substrates selected from the group consisting of ITO- or FTO-coated polyethylene terephthalate, ITO coated glass or quartz, and FTO coated glass or quartz. One embodiment of the invention encompasses an EC material made by the method of this invention having a transmittance difference between the oxidized and the reduced states of 10% and higher. In one embodiment, the EC material made by the method is able to retain at least 40% of its maximum contrast ratio after 50 switching cycles.

One embodiment of the invention encompasses a method for making an EC material comprising providing a substrate, applying at least one metal linker by spin coating, applying at least one polypyridyl complex by spin coating to form a layer, washing the layer, drying the layer, and repeating the applying steps to obtain a multiple layer EC material, wherein the step of applying the metal linker has a first spin rate, a second spin rate, a first spin time and a second spin time. In another embodiment, the step of applying the polypyridyl complex has a first spin rate, a second spin rate, a first spin time and a second spin time. In one embodiment, the metal linker is applied as a metal complex. According to this aspect and in one embodiment, the metal linker is present as a metal ion in a metal complex. The metal complex comprises the metal ion and organic ligand(s), inorganic ligand(s) or a combination thereof. The metal complex is a coordination complex according to this embodiment. Such metal complex is referred to as metal-linker complex or metal linker coordination complex in one embodiment.

In one embodiment the metal linker is a mixture of metal linkers. In one embodiment, the polypyridyl complex is a mixture of polypyridyl complexes.

In one embodiment, in methods of this invention, the step of applying at least one metal linker comprises applying the metal linker from a solution comprising said linker, and wherein the step of applying at least one polypyridyl complex comprises applying the polypyridyl complex from a solution comprising the polypyridyl complex, and wherein said solutions comprise a solvent, said solvent is selected from the group consisting of THF, alcohols, ethers, esters, halogenated solvents, hydrocarbons, ketones, or a mixture thereof. In one embodiment, the concentration of said linker in said solution and the concentration of said polypyridyl complex in said solution ranges between 0.1 mM and 10 mM. In one embodiment, the EC material made by methods of this invention is having a transmittance difference between the oxidized and the reduced states of 10% and higher. In one embodiment, the EC material made by methods of this invention is having a transmittance difference between the oxidized and the reduced states of 64% and higher. In one embodiment, the EC material made by methods of this invention is able to retain at least 40% of its maximum contrast ratio after 50 switching cycles between oxidized and reduced states. In one embodiment, the EC material made by methods of this invention is able to retain at least 54% of its maximum contrast ratio after 1000 switching cycles between oxidized and reduced states. In one embodiment, the metal linker is applied as a metal complex.

BRIEF DESCRIPTION OF THE DRAWINGS

FIG. 5A is the plot of the optical absorbance spectra after each deposition cycle. The baseline is the absorbance of a bare ITO substrate. FIG. 5B shows the intensities of the absorbance band at $\lambda=578$ nm ($R^2=0.998$).

FIG. 8A illustrates the purple color of an EC assembly made of Compound 1DB M=Fe film area of 6 cm×6 cm, while FIG. 8B illustrates the black color of an EC assembly made of Compound 2DB M=Fe on FTO/glass substrates film area of 4 cm×4 cm.

FIGS. 9A and 9C illustrate the optical absorbance spectra after every three deposition cycles for EC assembly made of Compound 1DB M=Fe and Compound 2DB M=Fe on an FTO/glass substrate, respectively, using $PbCl_2$ as the linker. FIGS. 9B and 9D illustrate the intensities of absorbance band at $\lambda=578$ nm ($R2=0.999$) for EC assembly of Compound 1DB M=Fe and at $\lambda=598$ nm ($R2=0.999$) for EC assembly of Compound 2DB M=Fe, respectively.

FIGS. 10A-10B illustrate the surface of an EC assembly made of Compound 1DB M=Fe as the EC material; and $PdCl_2$ as the linker, on an FTO/glass substrate, analyzed using optical microscopy, and atomic force microscopy (AFM). FIG. 10A is the surface as viewed by optical microscopy. FIG. 10B is the surface as observed by AFM.

FIGS. 11A-11C illustrate the surface and structure of an EC assembly made of Compound 1DB M=Fe as the EC material; and $PdCl_2$ as the linker, on an FTO/glass substrate; FIG. 11A is a SEM image of a cross section of the assembly, which was performed using focused ion beam (FIB), and reveals the different sections of the assembly; FIG. 11B is a scheme representing the different sections of the assembly; and FIG. 11C is a SEM image of the surface of the assembly.

(FIG. 15A) Cyclic voltammograms up to 1500 switching cycles. (FIG. 15B) Maximum current as in (FIG. 15A) versus the number of switching cycles.

FIG. 18A illustrates the contrast ratio at different switching times. Contrast ratio is defined as the difference in transmittance values of the oxidized and the reduced states of the film at a certain wavelength. FIG. 18B illustrates the contrast ratio versus switching time. Switching time is the time that is defined for the system to be held under a certain potential value. All the experiments were carried out at room temperature in 0.1 M $TBAPF_6$/ACN.

FIG. 20A illustrates the cyclic voltammograms taken at scan rates of 0.01-1.0 V/sec. FIG. 20B illustrates the exponential dependence of peak current on the scan rate (R2=0.99). FIG. 20C illustrates the linear dependence of peak current on the square root of the scan rate (R2=0.99).

FIG. 21A illustrates the cyclic voltammograms of assemblies constructed of 1, 3, 6, 9, 12, and 18 deposition cycles. FIG. 21B illustrates the dependence of maximum current on the number of deposition cycles.

FIG. 22A illustrates the contrast ratios of assemblies constructed of 1, 3, 6, 9, 12, and 18 deposition cycles ($R^2$=0.96). FIG. 22B illustrates the contrast ratio versus the number of deposition cycles ($R^2$=0.92).

(FIG. 23A) Difference in the charge of films constructed of 1, 3, 6, 9, 12 and 18 deposition cycles. ($R^2$=096). (FIG. 23B) Coloration efficiency versus number of deposition cycles ($R^2$=0.92). All experiments were carried out at room temperature, in 0.1 M TBAPF₆/ACN.

FIG. 26A illustrates the difference in the transmittance values between the oxidized and the reduced states of the film at λ=598 nm. FIG. 26B illustrates the stability of the contrast ratio as the assembly is cycled for 1000 switching cycles at a switching time of 2 seconds.

FIG. 27A illustrates the growth behavior of an assembly composed of equimolar mixture of Compound 1DB M=Fe and Compound 2DB M=Fe on FTO/glass. Meaning, each deposition cycle was performed using a solution comprising a 1:1 ratio of the two compounds. FIG. 27B illustrates the growth behavior of an assembly composed of block of Compound 1DB M=Fe followed by a block of Compound 2DB M=Fe (9 deposition cycles each) on FTO/glass. FIG. 27C illustrates the growth behavior of an assembly composed of a block of Compound 1DB M=Fe followed by a block of Compound 2DB M=Fe (13:5 deposition cycles, respectively) on FTO/glass. The baseline (black) is the absorbance of a bare FTO substrate. FIG. 27D illustrates the intensities of absorbance band at λ=585 nm ($R^2$=0.99) taken for the assembly presented in FIG. 27A. FIG. 27E illustrates the intensities of absorbance band at λ=581 nm ($R^2$=0.99) taken for the assembly presented in FIG. 27B. FIG. 27F illustrates the intensities of absorbance band at λ=584 nm ($R^2$=0.99) taken for the assembly presented in FIG. 27C.

FIG. 28A illustrates the optical absorbance spectra for an assembly composed of equimolar mixture of EC material made with Compound 1DB M=Fe and Compound 2DB M=Fe (18 deposition cycles) on FTO/glass. FIG. 28B illustrates the optical absorbance spectra of an assembly composed of a block of Compound 1DB M=Fe followed by a block of Compound 2DB M=Fe (each compound with 9 deposition cycles) on FTO/glass. FIG. 28C illustrates the optical absorbance of an assembly composed of a block of Compound 1DB M=Fe (13 deposition cycles) followed by a block of Compound 2DB M=Fe (five deposition cycles) on FTO/glass.

FIGS. 29A and 29D illustrate the cyclic voltammogram and SEC of an EC assembly composed of an equimolar mixture of Compound 1DB M=Fe and Compound 2DB M=Fe (18 deposition cycles) on FTO/glass. FIGS. 29B and 29E illustrate the cyclic voltammogram and SEC of an EC assembly composed of a block of Compound 1DB M=Fe (nine deposition cycles) followed by a block of Compound 2DB M=Fe (nine deposition cycles) on FTO/glass. FIGS. 29C and 29F illustrate the cyclic voltammogram and SEC of an EC assembly composed of a block of Compound 1DB M=Fe (13 deposition cycles) followed by a block of Compound 2DB M=Fe (five deposition cycles) on FTO/glass.

FIG. 30A is an EC material made with a block of Compound 1DB M=Fe (nine deposition cycles) followed by a block of Compound 2DB M=Fe (nine deposition cycles) on FTO/glass. FIG. 30B is an EC assembly composed of an equimolar mixture of Compound 1DB M=Fe and Compound 2DB M=Fe on FTO/glass. FIG. 30C is an EC assembly composed of Compound 2DB M=Fe (18 deposition cycles) on FTO/glass. FIG. 30D is an EC assembly composed of Compound 1DB M=Fe (18 deposition cycles) on FTO/glass.

FIG. 31A illustrates the optical absorbance spectra of the assembly taken every three deposition cycles. The black baseline is the absorbance of the ITO/PET substrate prior to deposition. FIG. 31B illustrates the absorbance intensities after every three deposition cycles at λ=578 nm ($R^2$=0.998).

FIG. 33A illustrates the cyclic voltammogram including up to 1500 switching cycles. FIG. 33B illustrates the maximum current versus the number of switching cycles where the CVs were recorded at a scan rate of 0.1 V/sec in 0.1 M TBAPF$_6$/ACN.

FIG. 36A illustrates the difference in the transmittance values between the oxidized and the reduced states of the device at λ=571 nm. FIG. 36B illustrates the contrast ratio as the device cycled for 100 switching cycles at a switching time of 4 seconds.

(FIG. 38A) 4 cm×4 cm device. (FIG. 38B) 6 cm×6 cm device.

FIG. 39A illustrates the optical absorbance spectra after every three deposition cycles, where the baseline (black) is the absorbance of a bare ITO/PET substrate; and FIG. 39B illustrates the absorbance band at λ=589 nm ($R^2$=0.99).

(FIG. 47A) Crystal structures of the isomers of complex 1DB M=Fe. Left: facial; Right: meridional. (FIG. 47B) Crystal structures of the enantiomers of complex 2DB M-Fe. Left: Λ; Right: Δ. The crystal structures are displayed in ORTEP views using thermal ellipsoids set at the 50% probability probability level. Hydrogen atoms are omitted for clarity, black, carbon; Blue, nitrogen; Yellow, iron.

(FIG. 49A) Color pallet constructed of assemblies of complexes 1DB-2DB, and combinations of complexes (1DB M=Fe and 2DB M=Fe); and (1DB M=Fe and 1DB M=Ru), with different number of deposition cycles. (FIG. 49B) Colors definition on the RGB color space of all the different assemblies.

(FIG. 50A) Optical absorption spectra corresponding to the consecutive oxidation and reduction of assemblies based on complex 1DB M=Fe, 2DB M=Fe, (1DB M=Fe and 2DB M=Fe), 1DB M=Ru, (1DB M=Fe and 1DB M=Ru) and 1DB M=Os (from top to bottom). Bare FTO substrates were used as baseline. Insets: Dependence of the contrast ratio on the switching time. (FIG. 50B) Top part: photographs of the colored and the bleached state of the assemblies. Bottom part: SEC at λ=573 nm, 598 nm, 589 nm, 495 nm, 573 nm (purple trace) and 495 nm (orange trace), and 510 nm (from top to bottom). The switching are performed under double-potential steps between 0.4-1.6 V, 0.4-1.8 V, 0.4-2.0 V, 0.7-1.7 V, 0.4-1.8 V and 0.2-1.4 V, (from top to bottom).

FIG. 54A) Mixed hierarchy. FIG. 54B) Blocks hierarchy when complex 1DB M=Fe is on top of complex 1DB M=Ru. FIG. 54C) Blocks hierarchy when complex 1DB M=Ru is on top of complex 1DB M=Fe.

FIG. 55A) Mixed hierarchy. FIG. 55B) Blocks hierarchy when complex 1DB M=Os is on top of complex 2DB M=Fe. FIG. 55C) Blocks hierarchy when complex 2DB M=Fe is on top of complex 1DB M=Os.

DETAILED DESCRIPTION

Figure 4:
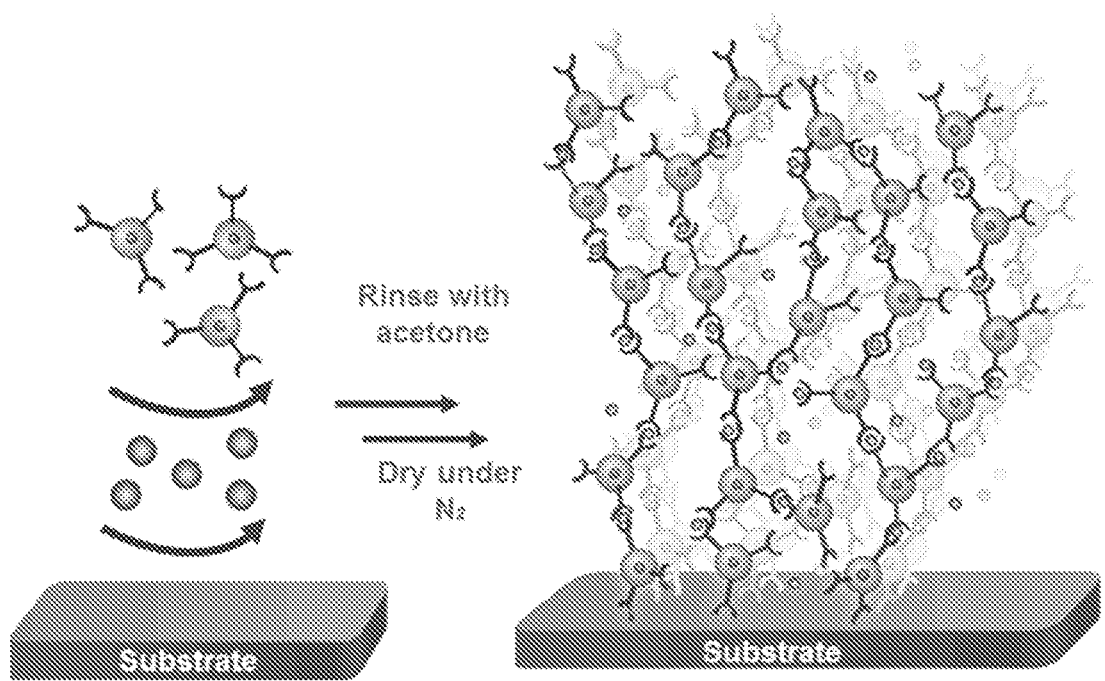
FIG. 4 shows schematic representation of one embodiment of film formation. The films are formed by alternating depositions of $PdCl_2$ linker and compound 1DB M=Fe or 2DB M=Fe, using spin-coating assisted layer-by-layer deposition.

The invention encompasses methods of depositing multiple layers of electrochromic materials onto a substrate thereby creating a multilayered EC assembly. The invention also encompasses multilayered EC materials composed of mixtures of at least two metal polypyridyl complexes. Not to be limited by theory, it is believed that the metal linker complexes to a polypyridyl compound thereby forming a layer where the metal linker is able to complex to a second polypyridyl compound thereby creating a multilayered EC assembly. The combination of Layer by Layer principles with spin coating layering techniques achieves well-designed nanostructures. For example, it was shown that in one case, the different layers constructed of Fe-polypyridyl-complex and Pd metal linker form a 3D coordination network with particular advantageous properties. FIG. 4 is a schematic representation of film formation by alternating depositions of a metal linker and a polypyridyl complex.

The method of the invention produces EC material that is thermally and electrochemically robust in air with very high contrast ratios (ON/OFF ratios). The EC material may operate under low voltage and have practical switching times. Thus, an EC material that has very high ON/OFF ratios, homogenous coating, low-voltage operations, high electrochemical stability and durability (such as light and thermal durability), color versatility, and low switching times, is useful in a variety of applications. The multilayered EC material has unique electrical properties suitable in applications such as smart windows, electrochromic windows, smart mirrors, optical filters, frequency doubling devices, spatial light modulators, pulse shapers, displays, signs, plastic electronics, lenses, sensors, to name a few. The method of the invention may be used for the formation of electrochromic coatings such as films.

As used herein, unless otherwise defined, the term "high electrochemical stability" refers to the capability of the EC material to retain high values of %ΔT, i.e., >90%, >95%, or >97%, after at least 1000, but preferably more than 3,000, 5,000, or 10,000 electrochemical switching cycles as immersed in an electrolyte solution/exposed to electrolyte gel, and exposed to air and to visible/UV light over a period of a few hours to a few days. In one embodiment, high electrochemical stability refers to the capability of the EC material to retain high values of %ΔT, i.e., >80%, >90%, >95%, or >97% or >99%, after at least 1000, but preferably more than 3,000, 5,000, 10,000 or 100,000 electrochemical switching cycles when immersed in an electrolyte solution or being in contact with electrolyte gel or solid electrolyte and exposed to air, to extreme atmosphere temperatures and to visible/UV light over a period of a few hours to a few years.

In one embodiment, the EC materials of this invention retained >90% of the original value of their contrast ratio after >1000 switching cycles.

The layer-by-layer (LBL) film-construction approach is an approach, based on the use of different kinds of interlayers interactions such as electrostatic interactions and hydrogen bonding for the purpose of adhering layers of different materials to each other to form a film. See, Ariga et al., Phys. Chem. Chem. Phys. 2007, 9 (19), 2319, hereby incorporated by reference. The LBL approach relates to cases where films are formed by depositing alternating layers of materials that are known to have a certain type of interactions between them.

It was found by the inventors of this invention that coordination interactions can be used as the interactions between different layers that are deposited according to the LBL approach. Coordination interactions were never before used for LBL assembly of material layers. All previous methods were based on electrostatic interactions or hydrogen bonding as discussed herein above. In one embodiment, solely coordination interactions are used to attach the different layers in films of this invention.

EC materials can be applied onto substrates using a variety of deposition approaches and techniques. This invention encompasses a novel method of making EC materials by applying a linking metal and polypyridyl compound using Layer by layer (LBL) deposition.

The novel LBL process of the present invention can be used with any of the known deposition techniques. For example, LBL film formation using coordination-bonds is coupled with roll-to-roll, dip coating, spin coating, spray coating, PVD, CVD or a combination thereof in various embodiments of this invention.

In one embodiment, LBL processes of this invention are coupled with the spin coating technique. LBL is used to create a film of two or more components. Accordingly, depositing EC material onto a substrate is performed using a combination of LBL and spin coating technique.

The inventors found that when LBL deposition of films comprising coordination interactions between the layers was combined with the spin coating technique, very uniform films of a relatively wide range of thicknesses were quickly and easily fabricated. The combination of LBL with spin coating is particularly applicable to well-designed nanostructures.

In one embodiment, the invention encompasses a method of making EC materials by applying to a substrate a metal linker and polypyridyl compound or complex using a Layer by Layer (LBL) deposition coupled with a spin coating technique. In particular, the method comprises making a multilayered EC material of different layers comprising at least one metal linker layer and at least one polypyridyl complex layer by LBL and spin coating to form a 3D coordination network. The method encompasses providing a substrate, applying by spin coating at least one metal linker, applying by spin coating at least one polypyridyl complex to form a layer, washing the layer with a solvent, drying the layer, and repeating the applying steps to obtain an EC material of a desired thickness.

The application steps should be performed for a sufficient amount of time to ensure application of the metal linker solution or pyridyl compound/complex.

Typically, the method of making an EC material encompasses providing a substrate, applying at least one metal linker to the substrate by spin coating, applying at least one polypyridyl compound or complex to the metal linker by spin coating to yield a coated substrate, washing the coated substrate, drying the washed coated substrate, and repeating the applying sequence to obtain an EC material of a desired thickness.

Typically, the step of applying the metal linker by spin coating requires applying either a metal, metal salt, metal complex, or a combination thereof to the substrate, optionally, these materials are in solution. Subsequently, the substrate may be spun at a first suitable rate and for a first suitable time to obtain an even coating. In other embodiments, the substrate may be spun first, and only while spinning, the metal linker or other materials are applied to it.

If necessary, the substrate is spun at a second suitable rate and a second suitable time. Typically, the first spinning rate is about 100 to about 2000 rpm, preferably the rate is about 400 rpm to about at 1600 rpm, and more preferably the first spinning rate is about 500 rpm to 800 rpm. Typically, the first spinning time is about 0.3 sec to about 60 sec, preferably the spinning time is about 5 sec to about 40 sec, and more preferably the first spinning time is about 10 sec to about 20 sec. Typically, the second spinning rate is about 200 to about 3000 rpm, preferably the rate is about 400 rpm to about at 2000 rpm, and more preferably the second spinning rate is about 600 rpm to about 1500 rpm. Typically, the second spinning time is about 1 second to about 120 seconds, preferably the spinning time is about 15 seconds to about 90 seconds, and more preferably the second spinning time is about 30 seconds to about 60 seconds.

Without being bound to any theory, it is believed that programming the spin coating process in two steps allows differentiation between two subsequent processes that are occurring during the spinning: the first process is the spreading of the material and the attachment of it to the substrate. This step requires relatively longer time, and therefore performs at slower rates. The subsequent step involves disposal of unattached molecules. This step requires higher speeds, as one has to overcome physical adsorption in order to dispose unattached material.

Typically, the step of applying the polypyridyl compound or complex by spin coating requires applying either a polypyridyl compound or a polypyridyl metal complex to the substrate coated with the metal linker, optionally, these materials may be in solution. Suitable solvents for the solution include, but are not limited to, tetrahydrofuran, ethyl ether, dichloromethane, methanol, acetonitrile others. Similar solvents may be used to dissolve/disperse the metal linkers; for example, $PdCl_2$ linker is soluble in THF. However, depending on the metal linker and the metal complex, other solvents may be used as long as the metal-linker or metal complex are dissolved or dispersed in such solvent.

Subsequently, the substrate may be spun at a first suitable rate and for a first suitable time to obtain an even coating. If necessary, the substrate is spun at a second suitable rate and a second suitable time. Typically, the first spinning rate is about 200 to about 800 rpm, preferably the rate is about 400 rpm to about at 600 rpm, and more preferably the first spinning rate is about 500 rpm. Typically, the first spinning time is about 1 sec to about 30 sec, preferably the spinning time is about 5 sec to about 20 sec, and more preferably the first spinning time is about 10 sec. Typically, the second spinning rate is about 700 to about 1300 rpm, preferably the rate is about 900 rpm to about at 1100 rpm, and more preferably the second spinning rate is about 1000 rpm. Typically, the second spinning time is about 10 seconds to about 60 seconds, preferably the spinning time is about 15 seconds to about 45 seconds, and more preferably the second spinning time is about 30 seconds.

Typically, the substrate includes, but is not limited to, a material selected from glass, doped glass, ITO-coated glass, FTO-coated glass, silica, silicon, doped silicon, Si(100), Si(111), $SiO_2$, SiH, silicon carbide mirror, quartz, a metal, metal oxide, a mixture of metal and metal oxide, group IV elements, polydimethylsiloxane (PDMS) and related organic/inorganic polymers, mica, organic polymer, plastic, zeolite, clay, wood, fabric, a membrane, optical fiber, ceramic, metalized ceramic, alumina, electricallyconductive material, semiconductor, steel, or stainless steel. The organic polymer includes, but is not limited to, polyacrylamide, polystyrene, and polyethylene terephthalate. The substrate may be in the form of beads, microparticles, nanoparticles, quantum dots, nanotubes, films, flat flexible surfaces, or flat rigid surfaces. The substrate may also be optically transparent to ultraviolet (UV), infrared (IR), near-IR (NIR), and/or other visible and non-visible spectral ranges. Preferably, the substrate is a rigid support comprising ITO or FTO coated glass or a flexible support of ITO coated PET. More preferably, the substrate is selected from the group consisting of ITO or FTO coated polyethylene terephthalate, ITO coated glass or quartz, and FTO coated glass or quartz. Optionally, the substrate may comprise a template or coupling layer.

Preferably, the substrate is transparent and has conducting properties. The substrate can be an n-type semiconductor with high carrier concentration, which leads to low electrical resistivity. High transmission in the visible and near-IR regions of the electromagnetic spectrum due to a wide band gap is also a desirable property of the substrate.

Metals used in the invention include those that can work as a metal linker between the substrate and the pyridyl compound or complex material or between two pyridyl compounds or complex materials. In the latter case, the pyridyl complex may be the same or different. Typical metals include, but are not limited to, transition metals, lanthanides, actinides, or main group elements. Transition metals include Zn, Os, Ru, Fe, Pt, Pd, Ni, Ir, Rh, Co, Cu, Re, Tc, Mn, V, Nb, Ta, Hf, Zr, Cr, Mo, W, Ti, Sc, Ag, Au, and Y. Lanthanides include La, Ce, Pr, Nd, Pm, Sm, Eu, Gd, Tb, Dy, Ho, Er, Tm, Yb, or Lu. Actinides include Ac, Th, Pa, U, Np, Pu, Am, Cm, Bk, Cf, Es, Fm, Md, No, or Lr. Main group elements include Zn, Ga, Ge, Al, Cd, In, Sn, Sb, Hg, Tl, or Pb. Preferably, the metal is Pd. The metal may be applied as a coordinate metal in either neutral or in an oxidation state. For instance, Pd can be applied as Pd or a Pd(II)-based complex. An example of Pd(II)-based complex is $PdCl_2(PhCN)_2$. Further, the metals or metal complexes are applied from solution. Suitable solutions include, but are not limited to, ethers such as tetrahydrofuran and ethyl ether. Suitable metals and metal complexes, as well as methods of making the complexes, can be found in PCT publication WO 2014/061018, hereby incorporated by reference. Metals in the metal-coordinated organic complexes of the invention can be any of the metals described herein above.

As used herein, unless otherwise defined, the term "pyridyl complex" refers to a metal having one or more e.g., two, three, or four pyridyl compounds coordinated therewith.

The bipyridyl complexes used in the invention are generally tris-bipyridyl complexes of the general formula (I):

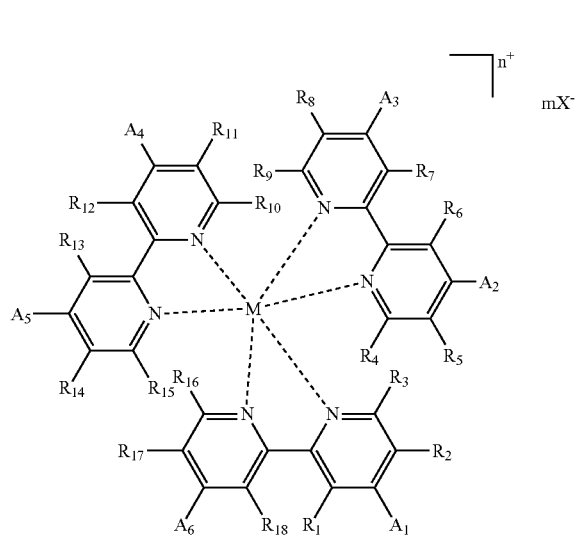

wherein

M is a transition metal selected from Mn, Fe, Co, Ni, Cu, Zn, Ti, C, Cr, Rh, or Ir;

n is the formal oxidation state of the transition metal, wherein n is 0-6;

X is a counter ion;

m is a number ranging from 0 to 6;

$R_1$ to $R_{18}$ each independently is selected from H, halogen, —OH, —$N_3$, —$NO_2$, —CN, —N($R_{20}$)$_2$, —CON($R_{20}$)$_2$, —COOR$_{20}$, —SR$_{20}$, —SO$_3$H, —CH=CH-pyridyl, —($C_1$-$C_{10}$)alkyl, —($C_2$-$C_{10}$)alkenyl, —($C_2$-$C_{10}$)alkynyl, —($C_1$-$C_{10}$)alkoxy, cycloalkyl, heterocycloalkyl, aryl, heteroaryl, protected carboxyl, or protected amino, wherein the ($C_1$-$C_{10}$)alkyl, ($C_2$-$C_{10}$)alkenyl, ($C_2$-$C_{10}$)alkynyl, cycloalkyl, heterocycloalkyl, aryl, or heteroaryl may optionally be substituted with halogen, —OR$_{20}$, —COR$_{20}$, —COOR$_{20}$, —OCOOR$_{20}$, —OCON($R_{20}$)$_2$, —($C_1$-$C_8$)alkylene-COOR$_{20}$, —CN, —N($R_{20}$)$_2$, —NO$_2$, —SR$_{20}$, —($C_1$-$C_8$) alkyl, —O—($C_1$-$C_8$)alkyl, —CON($R_{20}$)$_2$, or —SO$_3$H;

$A_1$ to $A_6$ each independently is a group of Formula III, i.e., a pyridine or pyridine derivative moiety, or of Formula IV, i.e., pyrimidine or pyrimidine derivative moiety, linked to the ring structure of the complex of general Formula I via $R_{19}$

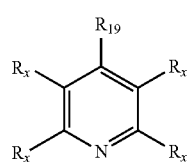
III

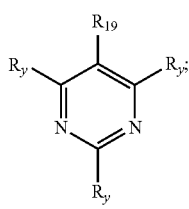
IV $R_{19}$ each independently is selected from a covalent bond, C—C, C=C, C≡C, N=N, C=N, N=C, C—N, N—C, —COO—, —CONH—, —CON(OH)—, —NR$_{20}$—, —Si($R_{20}$)$_2$—, an alkylene optionally interrupted by one or more heteroatoms selected from O, S, or N, phenylene, biphenylene, a peptide moiety consisting of 3 to 5 amino acid residues,

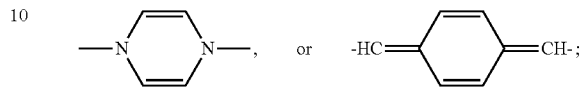

$R_x$ and $R_y$ each independently is selected from H, halogen, —OH, —$N_3$, —$NO_2$, —CN, —N($R_{20}$)$_2$, —CON($R_{20}$)$_2$, —COOR$_{20}$, —SR$_{20}$, —SO$_3$H, —CH=CH-pyridyl, —($C_1$-$C_{10}$)alkyl, —($C_2$-$C_{10}$)alkenyl, —($C_2$-$C_{10}$)alkynyl, —($C_1$-$C_{10}$)alkoxy, cycloalkyl, heterocycloalkyl, aryl, heteroaryl, protected carboxyl, or protected amino, wherein the ($C_1$-$C_{10}$)alkyl, ($C_2$-$C_{10}$)alkenyl, ($C_2$-$C_{10}$)alkynyl, cycloalkyl, heterocycloalkyl, aryl, or heteroaryl may optionally be substituted with halogen, —OR$_{20}$, —COR$_{20}$, —COOR$_{20}$, —OCOOR$_{20}$, —OCON($R_{20}$)$_2$, —($C_1$-$C_8$)alkylene-COOR$_{20}$, —CN, —N($R_{20}$)$_2$, —NO$_2$, —SR$_{20}$, —($C_1$-$C_8$) alkyl, —O—($C_1$-$C_8$)alkyl, —CON($R_{20}$)$_2$, or —SO$_3$H; and $R_{20}$ each independently is H, ($C_1$-$C_{10}$)alkyl, or aryl.

Another pyridyl complex used in the invention is an iron-based tris-pipyridyl complex of the general Formula II:

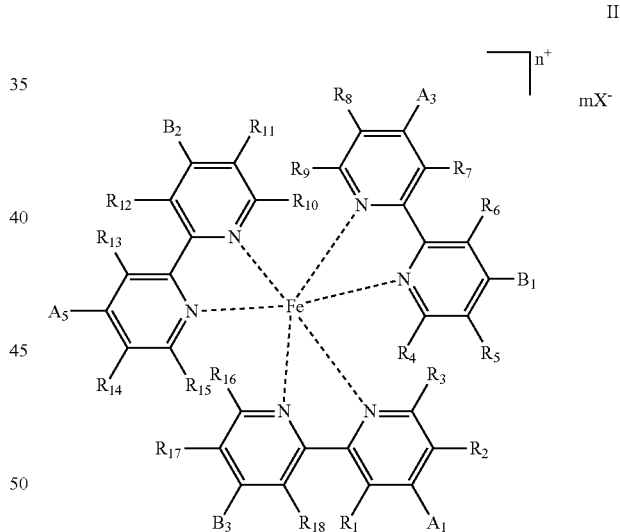

wherein n is the formal oxidation state of Fe, wherein n is 0-6;

X is a counter ion;

m is a number ranging from 0 to 6;

$R_1$ to $R_{18}$ each independently is selected from H, halogen, —OH, —$N_3$, —$NO_2$, —CN, —N($R_{20}$)$_2$, —CON($R_{20}$)$_2$, —COOR$_{20}$, —SR$_{20}$, —SO$_3$H, —CH=CH-pyridyl, —($C_1$-$C_{10}$)alkyl, —($C_2$-$C_{10}$)alkenyl, —($C_2$-$C_{10}$)alkynyl, —($C_1$-$C_{10}$)alkoxy, cycloalkyl, heterocycloalkyl, aryl, heteroaryl, protected carboxyl, or protected amino, wherein the ($C_1$-$C_{10}$)alkyl, ($C_2$-$C_{10}$)alkenyl, ($C_2$-$C_{10}$)alkynyl, cycloalkyl, heterocycloalkyl, aryl, or heteroaryl may optionally be substituted with halogen, —OR$_{20}$, —COR$_{20}$, —COOR$_{20}$, —OCOOR$_{20}$, —OCON($R_{20}$)$_2$, —($C_1$-$C_8$)alkylene- COOR$_{20}$, —CN, —N(R$_{20}$)$_2$, —NO$_2$, —SR$_{20}$, —(C$_1$-C$_8$)alkyl, —O—(C$_1$-C$_8$)alkyl, —CON(R$_{20}$)$_2$, or —SO$_3$H;

A$_1$, A$_3$, and A$_5$ each independently is a group of Formula III, i.e., a pyridine or pyridine derivative moiety, or of Formula IV, i.e., pyrimidine or pyrimidine derivative moiety, linked to the ring structure of the complex of general Formula II via R$_{19}$

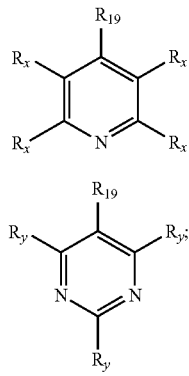

R$_{19}$ each independently is selected from a covalent bond, C—C, cis/tran C═C, C≡C, N═N, C—N, N═C, C—N, N—C, —COO—, —CONH—, —CON(OH)—, —NR$_{20}$—, —Si(R$_{20}$)$_2$—, an alkylene optionally interrupted by one or more heteroatoms selected from O, S, or N, phenylene, biphenylene, a peptide moiety consisting of 3 to 5 amino acid residues,

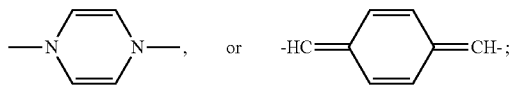

R$_x$ and R$_y$ each independently is selected from H, halogen, —OH, —N$_3$, —NO$_2$, —CN, —N(R$_{20}$)$_2$, —CON(R$_{20}$)$_2$, —COOR$_{20}$, —SR$_{20}$, —SO$_3$H, —CH═CH-pyridyl, —(C$_1$-C$_{10}$)alkyl, —(C$_2$-C$_{10}$)alkenyl, —(C$_2$-C$_{10}$)alkynyl, —(C$_1$-C$_{10}$)alkoxy, cycloalkyl, heterocycloalkyl, aryl, heteroaryl, protected carboxyl, or protected amino, wherein the (C$_1$-C$_{10}$)alkyl, (C$_2$-C$_{10}$)alkenyl, (C$_2$-C$_{10}$)alkynyl, cycloalkyl, heterocycloalkyl, aryl, or heteroaryl may optionally be substituted with halogen, —OR$_{20}$, —COR$_{20}$, —COOR$_{20}$, —OCOOR$_{20}$, —OCON(R$_{20}$)$_2$, —(C$_1$-C$_8$)alkylene-COOR$_{20}$, —CN, —N(R$_{20}$)$_2$, —NO$_2$, —SR$_{20}$, —(C$_1$-C$_8$)alkyl, —O—(C$_1$-C$_8$)alkyl, —CON(R$_{20}$)$_2$, or —SO$_3$H;

B$_1$ to B$_3$ each independently is selected from H, halogen, —OH, —N$_3$, —NO$_2$, —CN, —N(R$_{20}$)$_2$, —CON(R$_{20}$)$_2$, —COOR$_{20}$, —SR$_{20}$, —SO$_3$H, —CH═CH-pyridyl, —(C$_1$-C$_{10}$)alkyl, —(C$_2$-C$_{10}$)alkenyl, —(C$_2$-C$_{10}$)alkynyl, —(C$_1$-C$_{10}$)alkoxy, cycloalkyl, heterocycloalkyl, aryl, heteroaryl, protected carboxyl, or protected amino, wherein the (C$_1$-C$_{10}$)alkyl, (C$_2$-C$_{10}$)alkenyl, (C$_2$-C$_{10}$)alkynyl, cycloalkyl, heterocycloalkyl, aryl, or heteroaryl may optionally be substituted with halogen, —OR$_{20}$, —COR$_{20}$, —COOR$_{20}$, —OCOOR$_{20}$, —OCON(R$_{20}$)$_2$, —(C$_1$-C$_8$)alkylene-COOR$_{20}$, —CN, —N(R$_{20}$)$_2$, —NO$_2$, —SR$_{20}$, —(C$_1$-C$_8$)alkyl, —O—(C$_1$-C$_8$)alkyl, —CON(R$_{20}$)$_2$, or —SO$_3$H; and R$_{20}$ each independently is H, (C$_1$-C$_6$)alkyl, or aryl.

X is a counterion and may be any suitable anion having a negative charge, e.g., −1 or −2. Counterions include, but are not limited to, Br$^-$, Cl$^-$, F$^-$, I$^-$, PF$_6^-$, BF$_4^-$, BH$_4^-$, BPh$_4^-$, OH$^-$, ClO$_4^-$, NO$_3^-$, SO$_3^{2-}$, SO$_4^{2-}$, CF$_3$OO$^-$, CN$^-$, alkyl-COO$^-$, arylCOO$^-$, alkylSO$_3^-$, arylSO$_3^-$, or a combination thereof. The value of "m" represents the ratio between the oxidation state of the metal and the valence of the anion. Values of "m" include, but are not limited to, 0.5, 1, 1.5, 2, 2.5, 3, 4, 5, or 6.

In certain specific compounds, the tris-bipyridyl complex is a complex of the general Formula I, wherein M is Fe; n and m each is 2 or 3; X is PF$_6^-$; R$_1$ to R$_{18}$ each is H, A$_1$ to A$_6$ each independently is a group of the Formula III, wherein R$_x$ is H; and (i) R$_{19}$ each is C—C, i.e., [tris[4,4'-bis(2-(4-pyridyl)ethyl)-2,2'-bipyridine]iron(II)]bis(hexafluorophosphate), or [tris[4,4'-bis(2-(4-pyridyl)ethyl)-2,2'-bipyridine]iron(III)] tris(hexafluorophosphate); (ii) R$_{19}$ each is C═C, i.e., [tris[4,4'-bis(2-(4-pyridyl)ethenyl)-2,2'-bipyridine]iron(II)] bis(hexafluorophosphate), or [tris[4,4'-bis(2-(4-pyridyl)ethenyl)-2,2'-bipyridine]iron(III)] tris(hexafluorophosphate); or R$_{19}$ each is C≡C [tris[4,4'-bis(2-(4-pyridyl)ethynyl)-2,2'-bipyridine]iron(II)] bis(hexafluorophosphate), or [tris[4,4'-bis(2-(4-pyridyl)ethynyl)-2,2'-bipyridine]iron(III)] tris(hexafluorophosphate).

Other compounds include the tris-bipyridyl complex of general Formula I, wherein M is Fe; n and m each is 2 or 3; X is PF$_6^-$; R$_1$ to R$_{18}$ each is H, A$_1$ to A$_6$ each independently is a group of the Formula IV, wherein R$_y$ is H; and (i) R$_{19}$ each is C—C, i.e., [tris[4,4'-bis(2-(4-pyrimidinyl)ethyl)-2,2'-bipyridine]iron(II)] bis(hexafluorophosphate), or [tris[4,4'-bis(2-(4-pyrimidinyl)ethyl)-2,2'-bipyridine]iron(III)] tris(hexafluorophosphate); (ii) R$_{19}$ each is C═C, i.e., [tris[4,4'-bis(2-(4-pyrimidinyl)ethenyl)-2,2'-bipyridine]iron(II)] bis(hexafluorophosphate), or [tris[4,4-bis(2-(4-pyrimidinyl)ethenyl)-2,2'-bipyridine]iron(III)] tris(hexafluorophosphate); or R$_{19}$ each is C≡C [tris[4,4'-bis(2-(4-pyrimidinyl)ethynyl)-2,2'-bipyridine]iron(II)] bis(hexafluorophosphate), or [tris[4,4'-bis(2-(4-pyrimidinyl)ethynyl)-2,2'-bipyridine]iron(III)] tris(hexafluorophosphate).

In certain specific compounds, the iron based tris-bipyridyl complex is a complex of the general Formula II, wherein n and m each is 2 or 3; X is PF$_6^-$; R$_1$ to R$_{18}$ each is H, A$_1$, A$_3$, and A$_5$ each independently is a group of the Formula III, wherein R$_x$ is H; B$_1$ to B$_3$ each is methyl; and (i) R$_{19}$ each is C—C, i.e., [tris[4'-methyl-4-(2-(4-pyridyl)ethyl)-2,2'-bipyridine]iron(II)] bis(hexfluorophosphate), or [tris[4'-methyl-4-(2-(4-pyridyl)ethyl)-2,2'-bipyridine]iron(III)] tris(hexafluorophosphate); (ii) R$_{19}$ each is C═C, i.e., [tris[4'-methyl-4-(2-(4-pyridyl)ethenyl)-2,2'-bipyridine]iron(II)] bis(hexafluorophosphate), or [tris[4'-methyl-4-(2-(4-pyridyl)ethenyl)-2,2'-bipyridine]iron(III)] tris(hexafluorophosphate); or R$_{19}$ each is C≡C [tris[4'-methyl-4-(2-(4-pyridyl)ethynyl)-2,2'-bipyridine]iron(II)] bis(hexafluorophosphate), or [tris[4'-methyl-4-(2-(4-pyridyl)ethynyl)-2,2'-bipyridine]iron(III)] tris(hexafluorophosphate).

Other compounds include the iron based tris-bipyridyl complex of general Formula II, wherein n and m each is 2 or 3; X is PF$_6^-$; R$_1$ to R$_{13}$ each is H, A$_1$, A$_3$, and A$_5$ each independently is a group of the Formula IV, wherein R$_y$ is H; B$_1$ to B$_3$ each is methyl; and (i) R$_{19}$ each is C—C, i.e., [tris[4'-methyl-4-(2-(5-pyrimidinyl)ethyl)-2,2'-bipyridine]iron(II)] bis(hexafluorophosphate), or [tris[4'-methyl-4-(2-(5-pyrimidinyl)ethyl)-2,2'-bipyridine]iron(III)] tris(hexafluorophosphate); (ii) R$_{19}$ each is C═C, i.e., [tris[4'-methyl-4-(2-(5-pyrimidinyl)ethenyl)-2,2'-bipyridine]iron(II)] bis(hexafluorophosphate), or [tris[4'-methyl-4-(2-(5-pyrimidinyl)ethenyl)-2,2'-bipyridine]iron(Ill)] tris(hexafluorophosphate); or R$_{19}$ each is C≡C [tris[4'-methyl- 4-(2-(5-pyrimidinyl)ethynyl)-2,2'-bipyridine]iron(II)] bis(hexafluorophosphate), or [tris[4'-methyl-4-(2-(5-pyrimidinyl)ethynyl)-2,2'-bipyridine]iron(III)] tris(hexafluorophosphate).

Pyridyl compounds and complexes and methods of making them are found in PCT publication WO 2015/075714 and WO 2014/061018, hereby incorporated by reference.

Pyridyl moieties preferred in the invention include those represented by the following formulas:

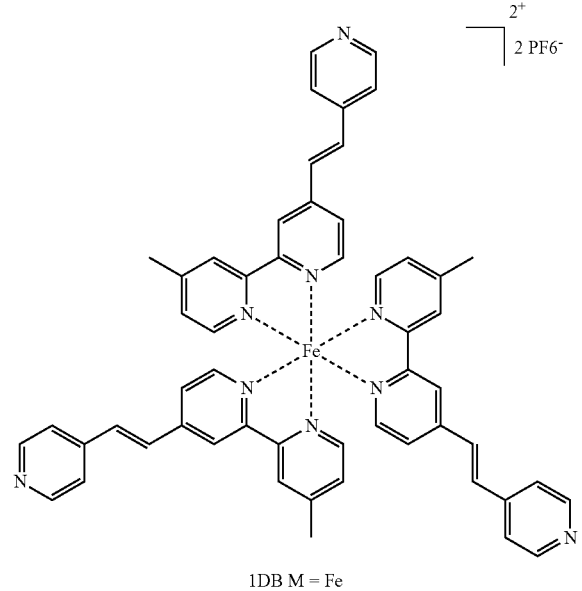

1DB M = Fe

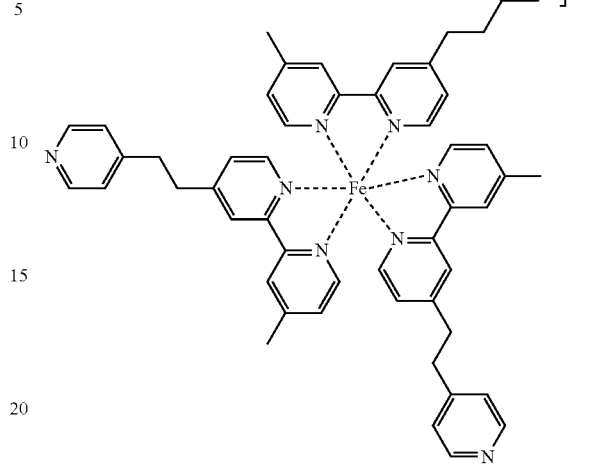

1SB M = Fe

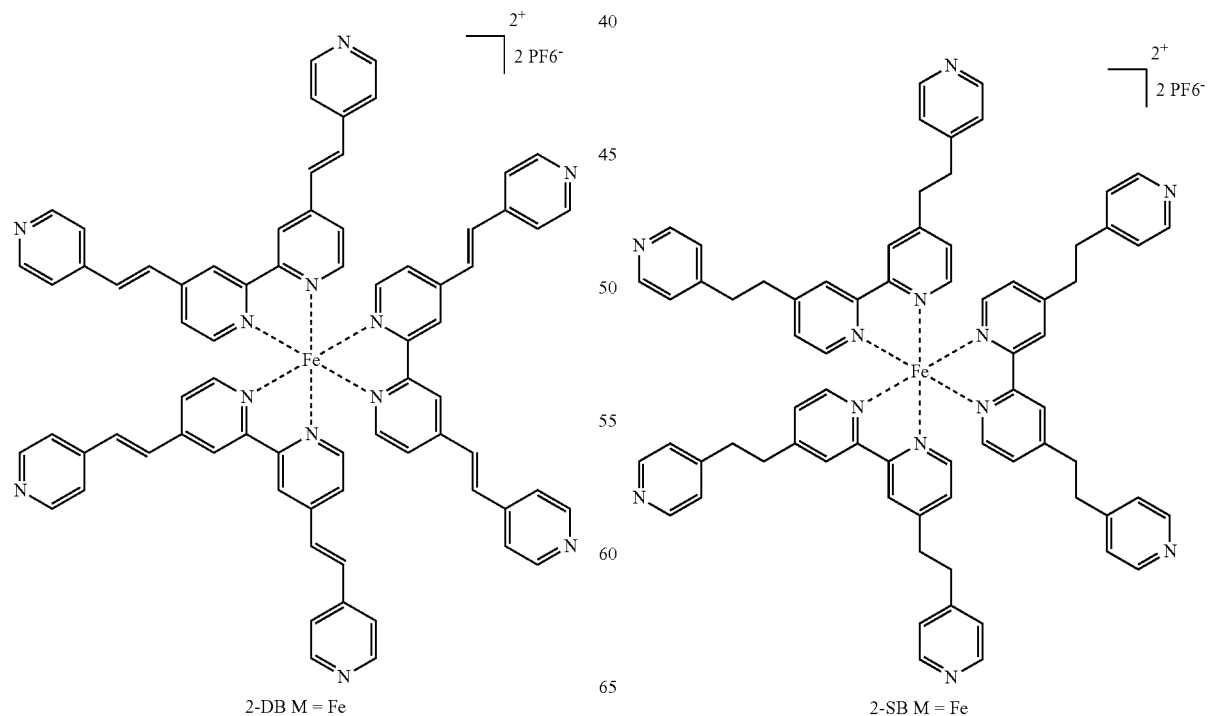

2-DB M = Fe

2-SB M = Fe

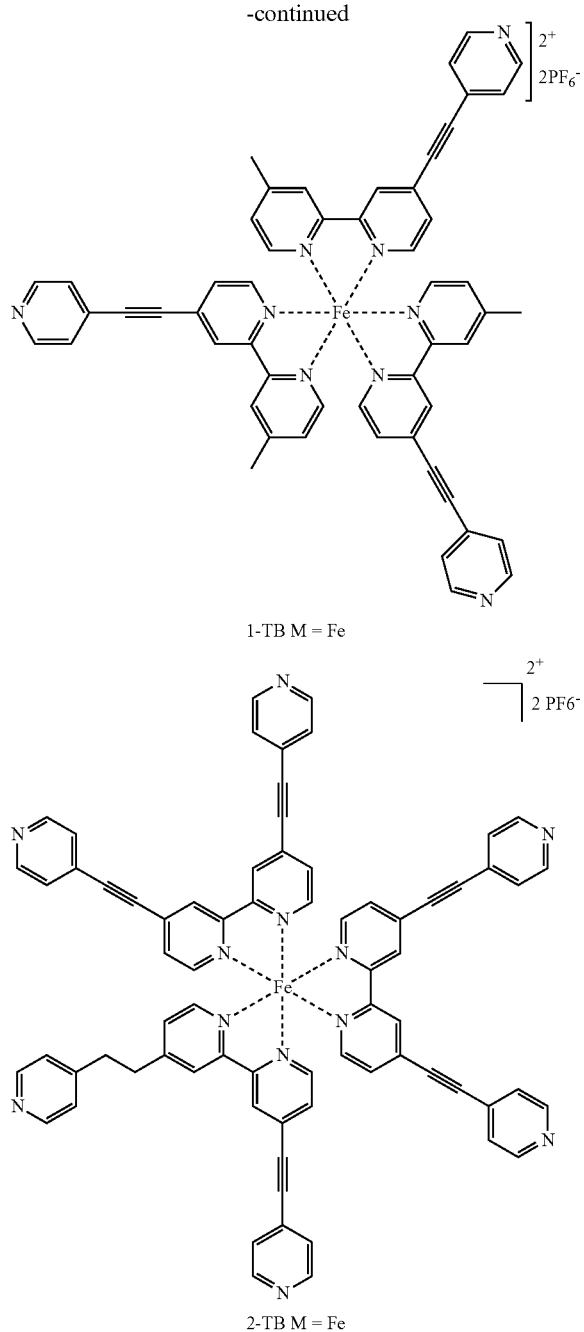

1-TB M = Fe

2-TB M = Fe

One method of the invention creates EC materials, such as thin films, based on compounds 1DB M=Fe or 2DB M=Fe made by a method comprising providing a substrate, applying in a stepwise manner palladium dichloride and the pyridyl complexes (Compound 1DB M=Fe or 2DB M=Fe or a mixture) using spin coating with LBL to form a layer, washing and drying the layer, and repeating the applying steps until the EC material has the desired number of layers or thickness. The combination of spin coating and LBL is referred to as a single deposition cycle. The invention encompasses methods where the deposition cycle is repeated to obtain an EC material with 2 to 40 layers, preferably 5 to 30 layers, and more preferably 10 to 20 layers. In one particular case, such as a film, the method includes 18 deposition cycles, where after every deposition cycle, the modified substrates were washed using acetone, and dried under $N_2$ stream. The fabrication process of the films occurs at ambient conditions.

In one particular embodiment, the method of the invention comprises providing a substrate, applying a metal-linker complex solution by spin coating to form a metal-linker layer, applying a pyridyl compound or complex by spin coating to form a pyridyl layer, washing the pyridyl layer, drying the washed pyridyl layer, and repeating the applying steps to obtain an EC material with 2 to 80 layers.

The metal-linker solution and pyridyl compound or complex are described above. Typically, the rinsing step is performed with at least one volatile organic solvent. Such volatile organic solvents include those capable of evaporating at room temperature. Typical volatile organic solvents include, but are not limited to, $CH_2Cl_2$, acetone, methanol, ethanol, THF, acetonitrile, among others.

Gasses suitable for use in the invention for the drying step, include, but are not limited to, nitrogen, argon, helium, neon, xenon, and radon. Preferably, the gas is nitrogen. Alternatively, the drying step can be air drying.

One embodiment of the invention encompasses a method for making an EC material comprising providing a substrate, applying at least one metal linker, applying at least one metal-coordinated organic complex to form a layer, washing the layer, drying the layer, and repeating the applying steps to obtain a multiple layer EC material.

In one embodiment, the metal-organic complex comprises at least one functional group, said functional group capable of binding to said metal linker. In one embodiment, the binding comprises a coordination bond between said functional group and said metal linker. In one embodiment, the metal complex is a polypyridyl complex.

In one embodiment, the applying steps comprise deposition techniques such as roll-to-roll, spin coating, dip coating, spray coating, physical vapor deposition (PVD), chemical vapor deposition (CVD) or combinations thereof. In one embodiment, the metal-coordinated organic complex comprises one or more isomers of the same compound. In one embodiment, the metal-coordinated organic complex comprises any mixture of isomers of the same compound. In one embodiment, the isomers are enantiomers. In one embodiment, the metal-coordinated organic complex comprises one or two enantiomers of the same compound. In one embodiment, the metal-coordinated organic complex comprises a mixture of said one or two enantiomers. In one embodiment, the enantiomer mixture is a racemic mixture. In one embodiment, the applying step(s) comprise spin coating.

In one embodiment, no template or coupling layer is used or is present between the substrate and the metal linker layer in EC materials of this invention. In one embodiment, the layer-application steps are performed manually. In one embodiment, the layer-application steps are performed in a partially automated manner or in a fully automated manner. Automation of the layer application technique results in fast fabrication of the EC materials in one embodiment.

Embodiments that are described herein for polypyridyl complexes are suitable for other metal-coordinated organic complexes as well. Embodiments that are described herein for Pd metal linkers are suitable for other metal linkers as well. Counter ions in metal-coordinated organic complexes of this invention can be any counter ion as known to the skilled artisan. In one embodiment, the growth of the layers in assemblies of this invention is such that the thickness of each layer is the same or is similar to the thickness of other layers in the assembly. In other embodiments, various layer thicknesses can be obtained for different layers in an EC material of this invention.

Definitions:

As defined herein, in metal-coordinated organic complexes, a metal ion is coordinately bonded to at least one organic molecule (a ligand). In some embodiments, the metal-coordinated organic complex is referred to in short as "metal-complex".

EXAMPLES

Example 1

Films Fabrication and Characterization 1.1 Substrates

Among the wide variety of transparent conductors that is available and is in use in the electrochromic (EC) field, transparent conducting oxides (TCO) are the most common ones. However, alternatives to TCO can also be found. For example, thin metal sheets (e.g. silver of gold); graphene and carbon nanotubes.

The two most common TCO which are in use both for research and industrial purposes, are indium tin oxide (ITO) and fluorine doped tin oxide (FTO). Usually these TCO are deposited on glass, but in the plastic electronics industry, ITO can also be deposited on flexible substrates, such as polyethylene terephthalate (PET).

Figure 1:
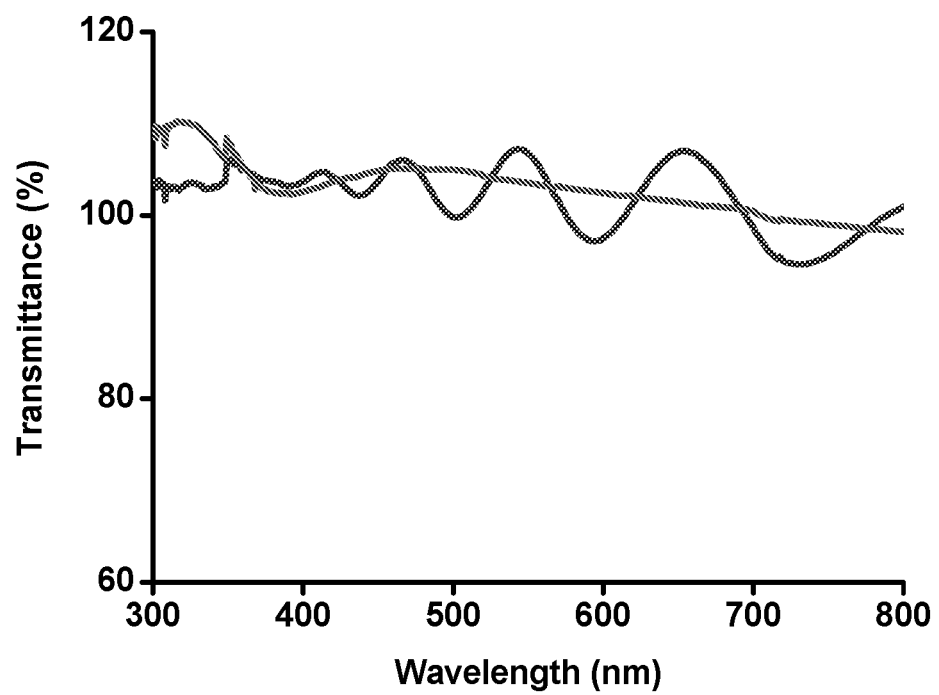
FIG. 1 is a transmittance spectra of bare ITO/glass (green) and bare FTO/glass (blue) substrates.

ITO substrates are widely used due to the fact that it combines unique transparent and conducting properties. It is an n-type semiconductor with high carrier concentration, which leads to low electrical resistivity. Moreover, ITO shows high transmission in the visible and near-IR regions of the electromagnetic spectrum due to its wide band gap (FIG. 1).

Figures 2A, 2B:
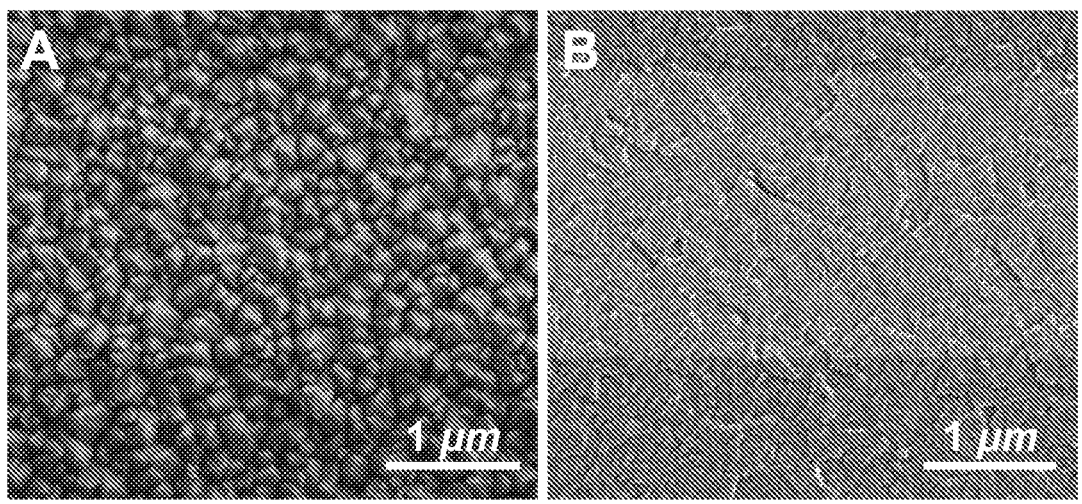
FIGS. 2A-2B are SEM images of (FIG. 2A) bare FTO/glass and (FIG. 2B) bare ITO/glass substrates.

FTO substrates are also used widely, mainly for energy-efficient windows in architectural applications. FTO is also an n-type semiconductor, with large band gap, which allows it to be transparent in the visible range (FIG. 1). Among the many advantages of FTO, the following two play a crucial role when considering it as an alternative to ITO: (1) increasing scarcity of indium leads to higher costs of ITO. (2) FTO has rougher surface with respect to ITO, which results in higher surface area (FIG. 2). AFM measurements reveal roughness values of 0.8 nm for FTO and 0.2 nm for ITO.

In the examples below, the following substrates were in use: FTO and ITO coated glass substrates, ITO coated polyethylene terephthalate (PET) substrates. For each substrate, a suitable cleaning procedure was developed. The clean substrates were kept in a sealed and dark container, until further use. It is to be noted that other transparent conducting substrates may be used to support the EC materials of the invention. Other cleaning procedures may be used to prepare the substrates of the invention for use as known to the skilled artisan.

1.2 Deposition Approaches and Techniques

EC materials can be applied on any of the substrates that were described above in various deposition approaches and techniques. Among the different approaches, the following two are the most common: one step approach—mainly common in fabrication of polymers-based films; and Layer by layer (LBL) approach—mainly common when the film is constructed of two or more components. There is a large variety of techniques that can be combined with each of the two described deposition approaches. As examples roll-to-roll, spin coating, dip coating and spray coating can be considered, as well as PVD and CVD techniques.

LBL deposition is a well-studied approach, utilizing various types of inter-layers interactions such as electrostatic interactions and hydrogen bonding. It was discovered by the inventors that when combined with spin coating technique, very uniform films of a relatively wide range of thicknesses can be fabricated quickly and easily.

Figure 3:
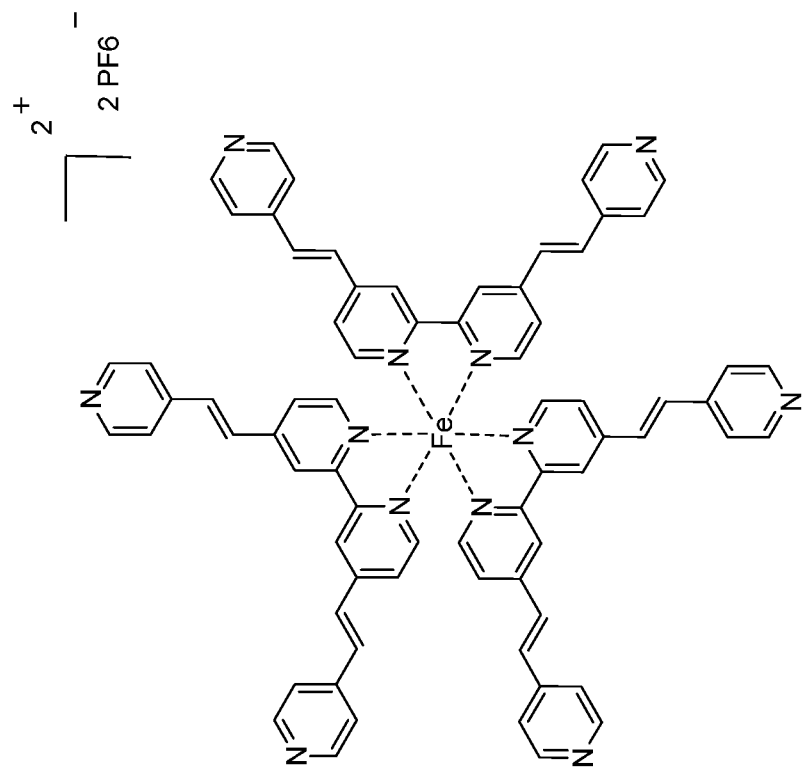
FIG. 3 shows molecular structures of polypyridyl complexes (1DB M=Fe) and (2DB M=Fe).
Figure 3:
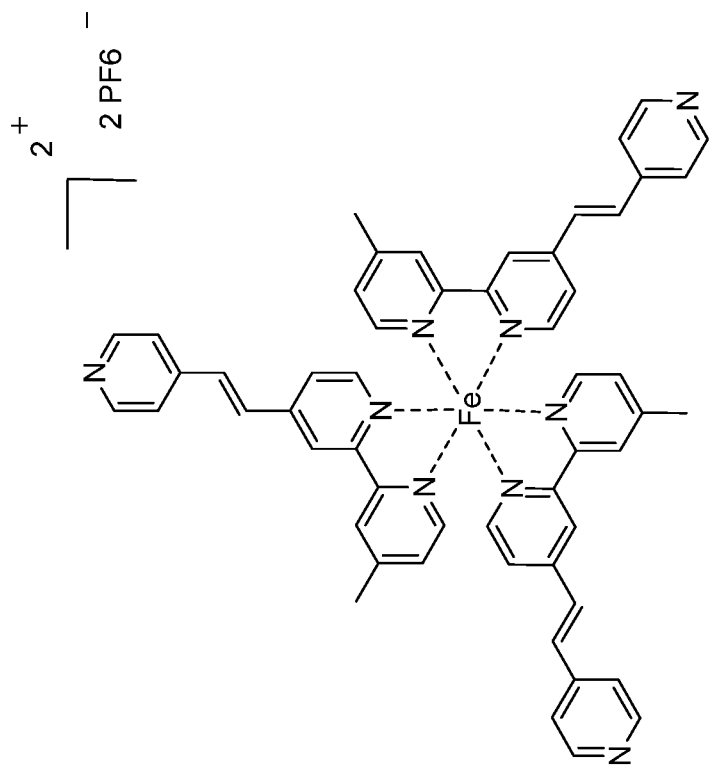

In this example, this combination of LBL approach and spin coating as a fabrication technique is utilized in order to achieve well-designed nanostructures. The different layers are constructed of Fe-complex (compounds 1DB M=Fe or 1DB M=Fe, see FIG. 3) and a Pd linker, forming a 3D coordination network. In this embodiment, the benzonitrile ligands of the $PdCl_2(PhCN)_2$ linker complex are relatively weakly coordinated to the Pd metal center and therefore are readily replaced by the pyridine-binding sites of the polypyridyl complexes. Thin films based on compounds 1DB or 2DB, were fabricated, in a stepwise manner mediated by palladium dichloride, which coordinates to the pyridyl moieties of the different building blocks. The fabrication process includes alternating depositions of solutions of $PdCl_2(PhCN)_2$ and polypyridyl complexes (1DB or 2DB), using spin coating LBL approach. These two subsequent steps are referred to as a single deposition cycle. The films are consisted of 18 deposition cycles, where after every deposition cycle, the modified substrates were washed using acetone, and were dried under $N_2$ stream. The fabrication process of the films occurs at ambient conditions. However, other temperature/pressure conditions may be used for the fabrication process. In some embodiments the films are labeled in the following manner: (Pyridyl complex type|Number of deposition cycles|Substrate type). For example, (Compound 1DB M=Fe|18|FTO/glass).

In this embodiment, as the procedure above describes, the first deposition step is of palladium dichloride linker. The interaction between the Pd linker to the substrate was studied, in order to define whether this is simply physical absorption, or there are coordination interactions between the Pd and the substrate. Previous works describe the affinity of Pd(II)-based complexes to oxide substrates, such as silica and alumina, by coordination of Pd to the hydroxyl groups which are on the surface. However, no literature is found on the absorption of Pd(II)-based complexes on ITO or FTO. In a previous study, a coupling and template layer were used in order to attach the Pd linker to the substrate. However, this linking layer has electrically isolating nature, and therefore it affected the electrochemical characteristics of the films.

Control experiments were designed, in order to evaluate if coupling and template layers between the substrate and the metal linker are needed in the case of spin coating fabrication process or can Pd be directly attached to the substrates using this technique. Further experiments were designed in order to evaluate if Pd is indeed needed for the pyridyl-complex layer growth process. In the first two control experiments, the substrates were modified with coupling and template layer (according to a known procedure), and the film was built with and without Pd as the linker. In two additional control experiments, the substrates were not modified, and again the film was built with and without Pd. The results of those experiments were that only in the experiments where Pd was used, an effective growth was evident. From this it was concluded that the film growth is not based on physical absorption but on Pd mediated coordination between the layers. Moreover, since there was no difference in the growth of the films on modified substrates with respect to non-modified ones, it was concluded that Pd can be attached directly to the substrates.

It is noted that other metal-coordinated organic compounds can be used as the metal-coordinated organic complex, and other metal linkers or other metal linker complexes can be used as the metal linker. The metal-coordinated organic complexes may comprise other polypyridyl compounds, other complexes comprising functional groups other than pyridines, compounds comprising both pyridine and non-pyridine functional groups, linkers comprising metals other than Pd, linkers comprising other ligands etc.

In order to strengthen the above, and also to test whether Pd is present after further deposition steps, XPS measurements were performed, where the ratio between Pd and Fe was tested. The measurements were performed on films with different number of deposition cycles deposited on FTO on glass substrates in order to show that the growth is homogenous. The results are presented in table 1:

TABLE 1

Pd/Fe ratio in films constructed of different number of deposition cycles deposited on FTO/glass substrates, as was extracted from XPS measurements. The expected value for a fully formed network is 1.5.

| | Pd/Fe | |
|---|---|---|
| Deposition cycle | $\Theta = 0°$* | $\Theta = 45°$ |
| 1 | 2.5 | 2.9 |
| 5 | 2.6 | 2.7 |
| 10 | 2.6 | 2.8 |
| 15 | 3.1 | 3.2 |
| 18 | 2.9 | 2.8 |

*average between two points

In a fully coordinated network, the ratio between Pd and the metal center, Fe, is calculated to be 1.5 atoms of Pd per each Fe atom (each complex coordinates three Pd atoms each is shared between two complexes). However, the results above show an average Pd/Fe ratio of 2.8±0.3, meaning excess of Pd. This indicates a porous film structure with embedded Pd atoms in between the layers. Moreover, the homogeneity of the film can be seen from the results, as the ratio stays constant as the number of deposition cycles increases. Without being bound to any theory, it is believed that the embedded atoms are those which are not coordinated to the metal complex in the assembly. These atoms are in excess of the atoms needed to connect between the complexes/layers through coordination bonds. As noted above, the results indicate that the film is homogeneous, as the ratio remains constant as the number of deposition cycles increases.

The films were characterized by UV/vis spectroscopy, X-ray photoelectron spectroscopy (XPS), cyclic voltammetry (CV), chronoamperometry (CA) and spectroelectrochemistry (SEC). The surface of the films was characterized by scanning electron microscopy (SEM), atomic force microscopy (AFM) and optical microscopy.

1.3 Films on Rigid Support—Fabrication and Characterization 1.3.1 ITO/Glass

As was described above, ITO substrates have unique transparent and conducting properties. These are substrates with low electrical resistivity, and high transmission in the visible and near-IR regions of the electromagnetic spectrum.

Figure 5A:
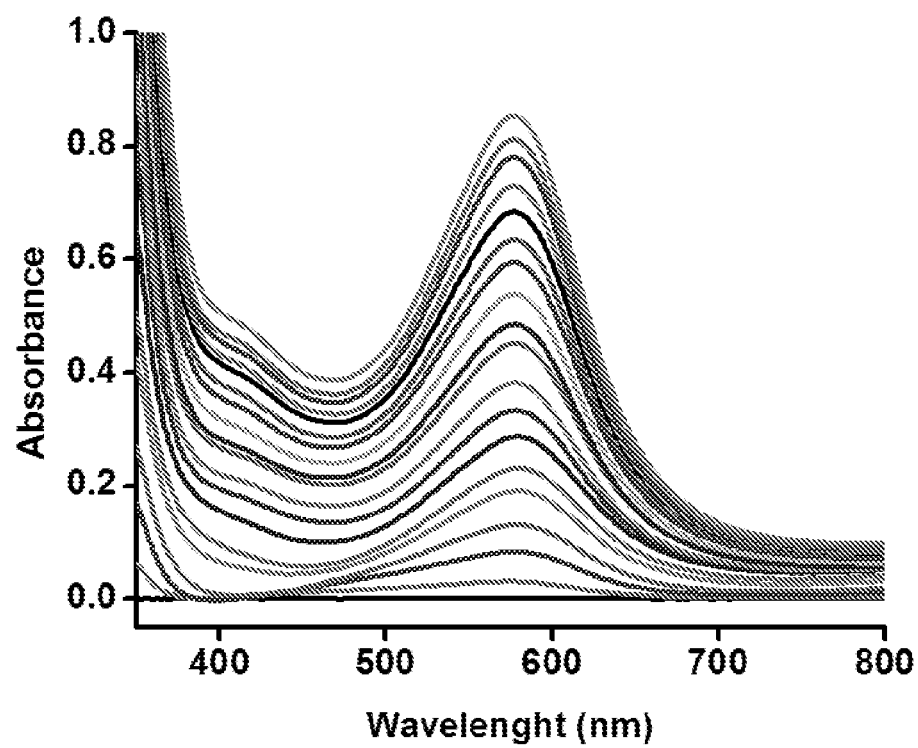
FIGS. 5A-5B illustrate the film growth on an ITO/glass substrate.
Figure 5B:
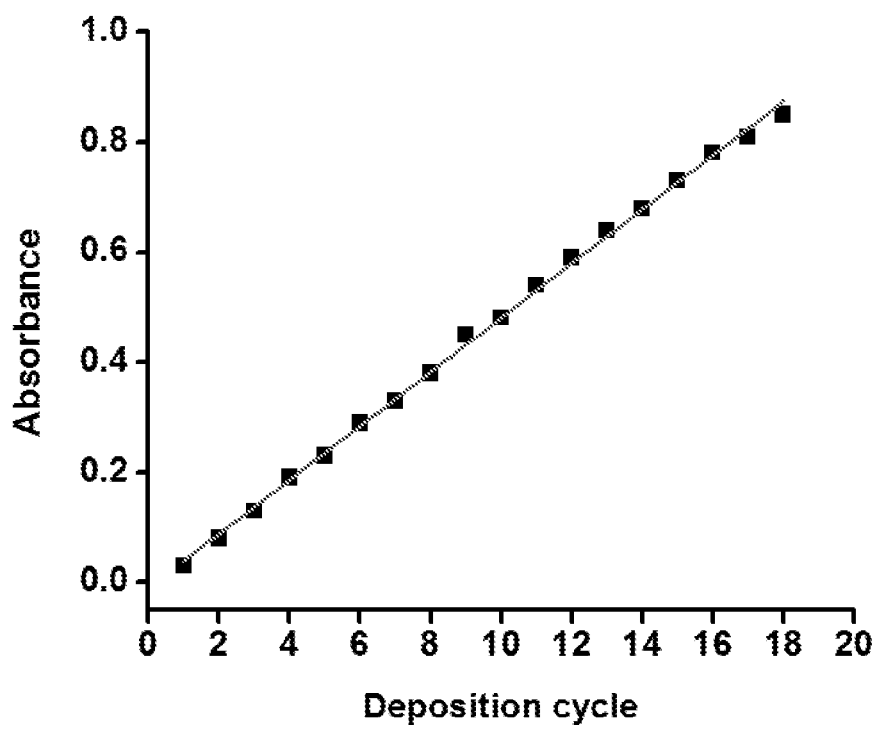

Compound 1DB M=Fe was deposited on ITO substrate, according to the described film fabrication method. Compound 1DB M=Fe has a characteristic metal to ligand charge transfer (MLCT) band at $\lambda=578$ nm that is increasing linearly as the number of deposition cycles increases (FIGS. 5A-5B). This trend of growth indicates that the same amount of material is being deposited in each of the deposition cycles.

Figure 6:
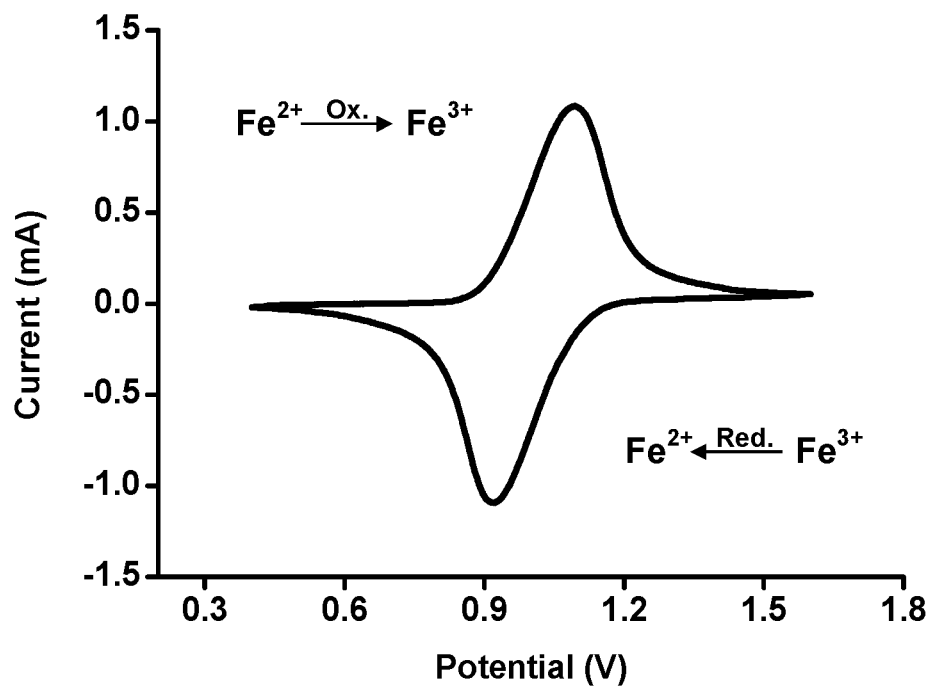
FIG. 6 illustrates the cyclic voltammetry measurements of an EC assembly made of Compound 1DB M=Fe as the EC material; and $PdCl_2$ as the linker, on an ITO/glass substrate. The material was cycled for 2000 redox cycles with a minor decrease in current of <2%. The CV was recorded at a scan rate of 0.1 V/sec, in 0.1 M $TBAPF_6$/ACN.
Figure 7:
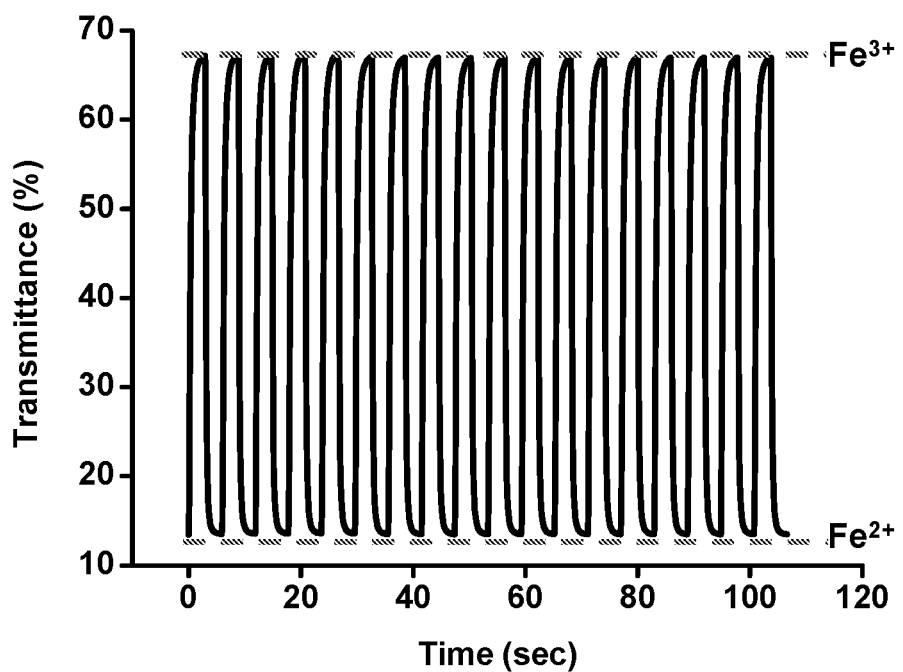
FIG. 7 illustrates the spectroelectrochemical behavior of an EC assembly made of Compound 1DB M=Fe as the EC material; and $PdCl_2$ as the linker, on an ITO/glass substrate, and the difference in transmittance values between the oxidized and the reduced states of the assembly at $\lambda=578$ nm.

The electrochemical and spectroelectrochemical properties of the film were evaluated in solution using three-electrode cell configuration consisting of the modified ITO substrate as working electrode, Pt wire as counter electrode and Ag/Ag$^+$ as reference electrode. CV measurements of the film reveal reversible redox processes of Fe$^{-2}$/Fe$^{+3}$ pair (FIG. 6).

The oxidation and reduction processes that occur in the film are detectable using optical spectroscopy: when the film is oxidized, the intensity of the MLCT band is significantly reduced, resulting in bleaching, while when it is reduced, the film exhibits a purple color. SEC experiments were done by applying double potential steps as a function of time, and recording the optical response at $\lambda=578$ nm as the percentage of transmittance (% T) over time. Double potential step chronoamperometry is a technique where the potential of the working electrode is stepped forward for a specified period of time, then stepped back for a specified period of time. Current is monitored and plotted as a function of time. The results reveal a very high transmittance difference between the oxidized and the reduced states (i.e. contrast ratio) of 54%. Moreover the film is able to retain 95% of its maximum contrast ratio even after 160 switching cycles.

1.3.2 FTO/Glass

Figures 8A, 8B:
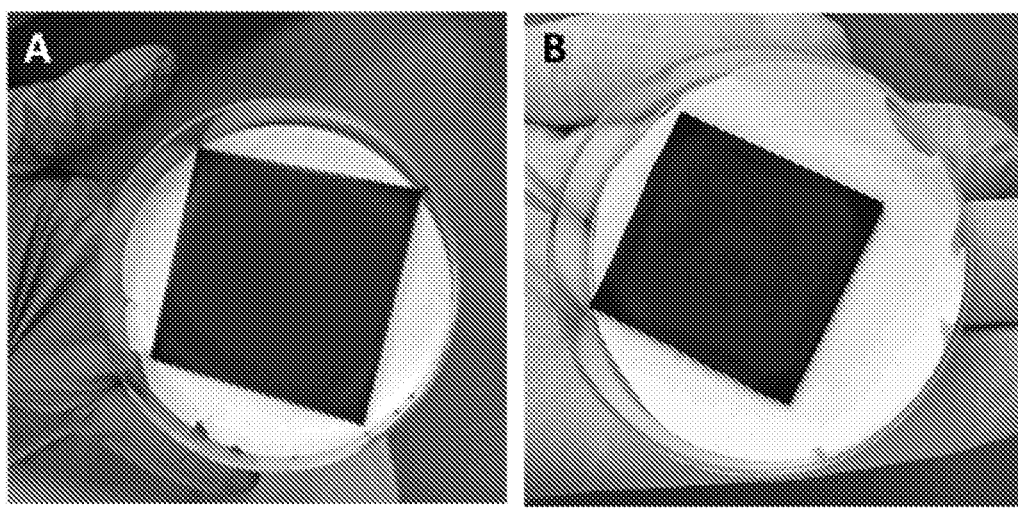
FIGS. 8A-8B illustrate the different colors of EC assemblies made of Compound 1DB M=Fe or 2DB M=Fe as the EC material; and $PdCl_2$ as the linker, on an FTO/glass substrate (18 deposition steps).
Figure 9A:
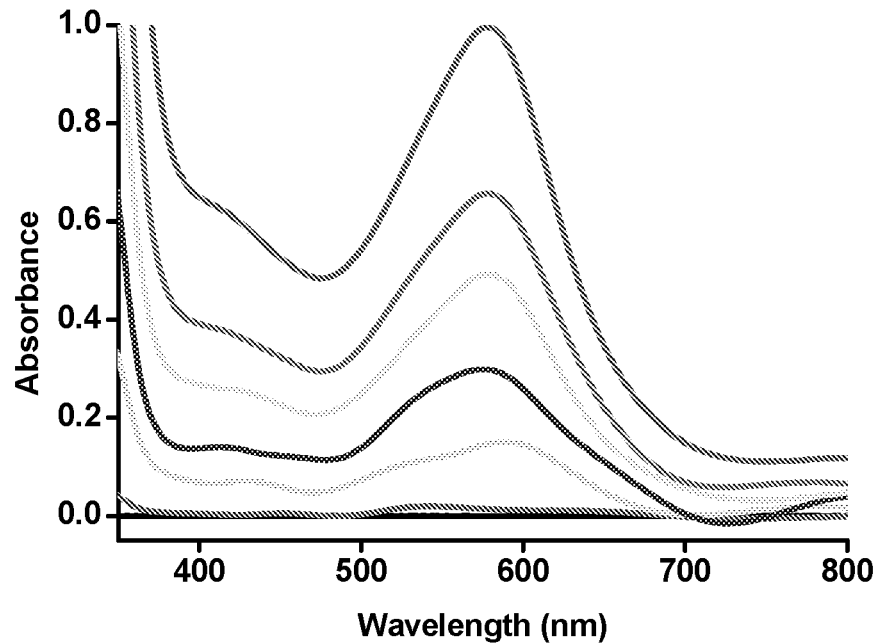
FIGS. 9A-9D illustrate film growth on an FTO/glass substrates.
Figure 9B:
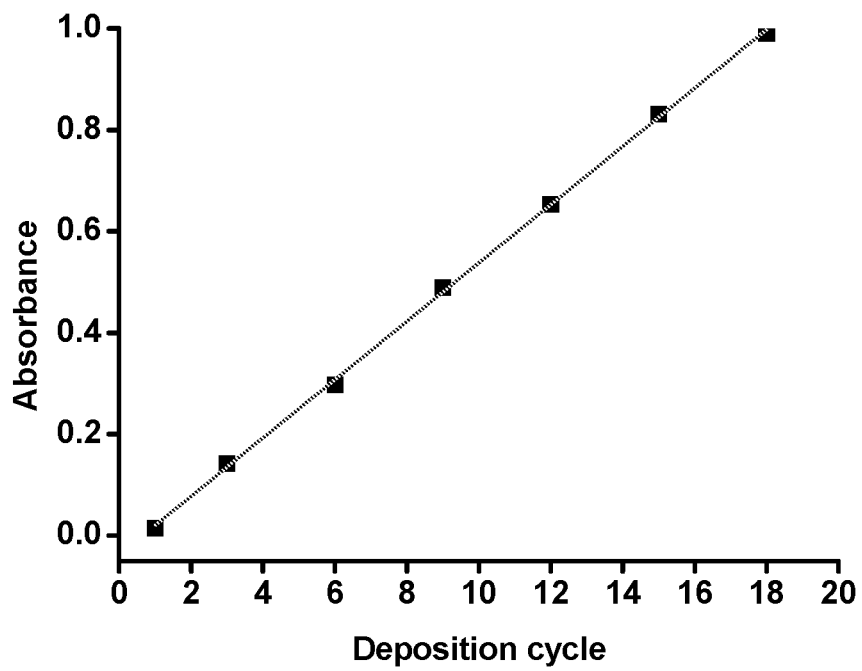
Figure 9C:
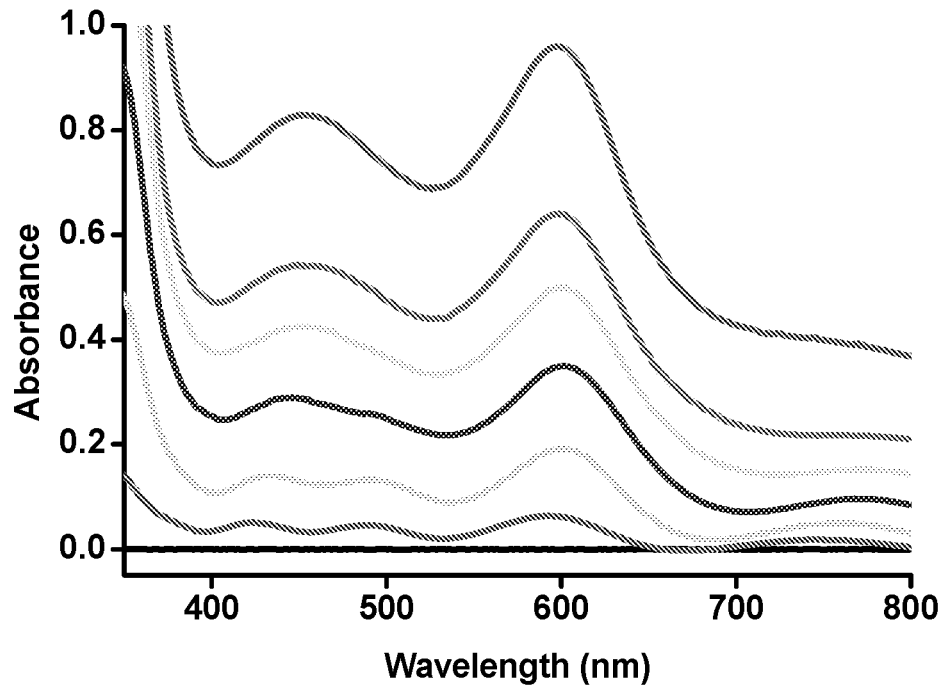
Figure 9D:
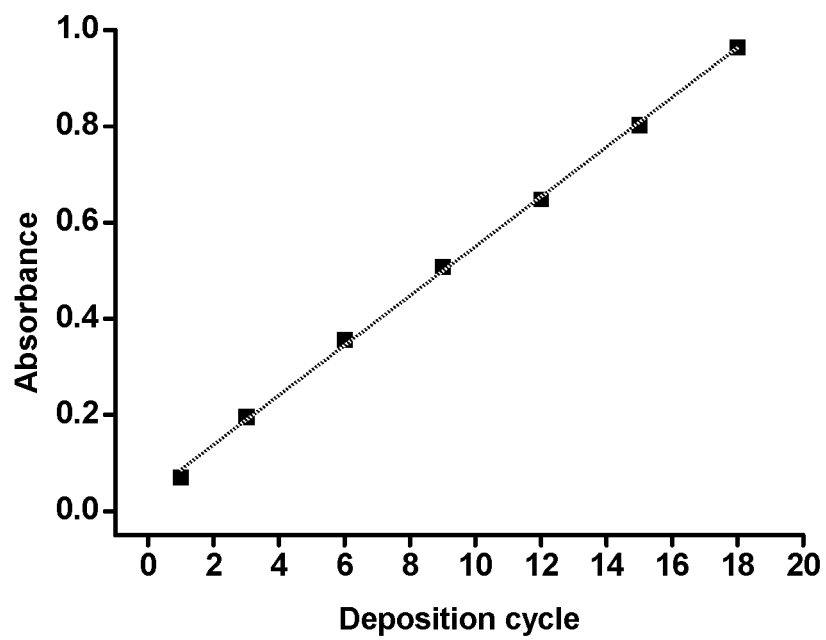

Films with both Fe-complexed compounds 1DB and 2DB were fabricated on FTO/glass substrates, according to the described film fabrication method. Both of the films exhibit linear growth versus the number of deposition cycles. Compound 1DB M=Fe has a characteristic MLCT band at $\lambda=578$ nm, which results in a purple color, while Compound 2DB M=Fe has two distinct MLCT bands at $\lambda=452$ nm and $\lambda=598$ nm. The combination of these two bands gives rise to blackish color of a Compound 2DB M=Fe-based film (FIGS. 8A-8B).

As the number of deposition cycles increase, the MLCT bands increase linearly, for both of the compounds (FIGS. 9A-9D). This finding contradicts previous results regarding these compounds, where an exponential growth was observed for a Compound 1DB M=Fe-based film grown using dip-coating. The differences are that in this example, the films are deposited on bare substrates, while previously it was deposited on modified substrates. Further, the deposition method is different (spin coating vs. dip coating), which affects drastically the growth trends. In the previous work, EC assemblies were deposited using dip coating deposition method, on substrates that were modified with a template layer. Using this approach, Pd atoms were found to be temporarily stored and later released, what caused an increase in the growth rate, and therefore exponential dependence of the absorbance on the number of deposition cycles. In contrast, the EC assemblies that are deposited using the method of invention are deposited on unmodified substrates. Moreover, there is no evidence of delayed release of Pd atoms, and therefore there is no increase in the growth rate, which leads to a linear dependence of the absorbance on the number of deposition cycles. Such linear growth of the layers is important in view of applications that require controlled deposition and uniform thickness of layers. Such linear growth enables simple design of layered materials wherein the thickness of each layer can be controlled and can be made identical, equivalent or with constant thickness ratio with respect to the thickness of other layers in the structure.

The surface and structure of Compound 1DB MB=Fe based film were characterized using electron microscopy. The surface area of the film was sampled using optical microscopy and AFM. Both of methods reveal grain-like, homogenous surface (FIGS. 10A-10B). The roughness of the film was found to be up to 40 nm (approximately one tenth of the film thickness). Moreover, cross section of the film was obtained by milling into it using a focused ion beam (FIB). The cross section was later characterized using SEM, revealing the different areas of the film: glass support, FTO layer, compound 1DB M=Fe-based film, and Pt thin layer to prevent damage to the film as the milling was going on (FIGS. 11A-11B). The thickness of the film was found to be 400-500 nm. The surface of the film was also characterized by SEM, and is correlated with the findings described above. (FIG. 11C).

Figure 12:
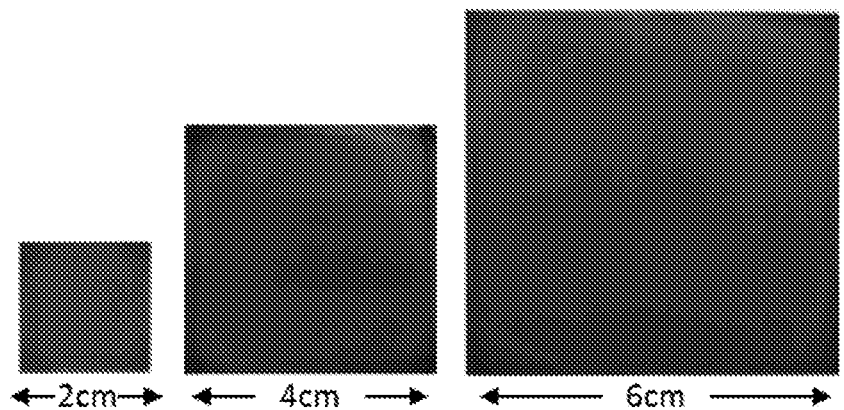
FIG. 12 shows photographs of different sized films of [Compound 1DB M=Fe, 18 deposition steps, substrate is FTO/glass].

Films of different sizes were fabricated, using the same fabrication method (FIG. 12). Homogenous films with identical optical and electrochemical characteristics were obtained.

Figure 13:
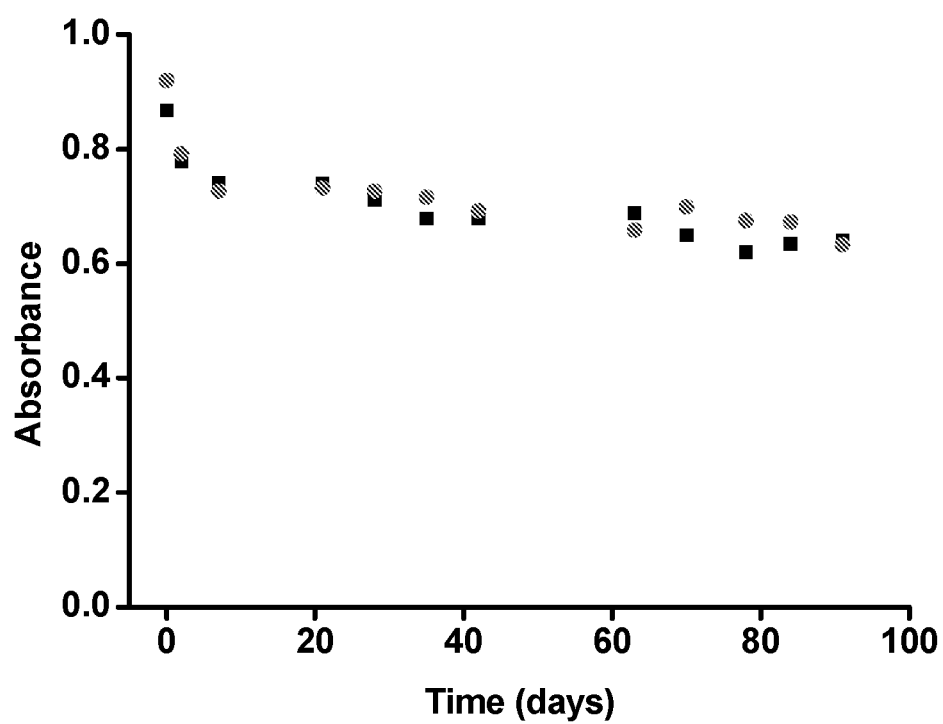
FIG. 13 illustrates the thermal and light stability of an EC assembly made of Compound 1DB M=Fe as the EC material; and $PdCl_2$ as the linker, on an FTO/glass substrate, which observed a slight initial decrease in the absorbance of both of the samples that later stabilized over time.

Stability to light and high temperature is one of the features that an EC material should own. Two samples of films comprising Compound 1DB M=Fe were tested: one was kept exposed to day light, and the other was kept at 100° C. Both of the experiments last for more than 120 days, and are still running. The results were obtained by UV/vis absorbance. FIG. 13 shows initially slight decrease in the absorbance of the both of the samples, which is later followed by stabilization.

1.3.2.1 Electrochemical Characteristics of Compound 1DB M=Fe

Figure 14:
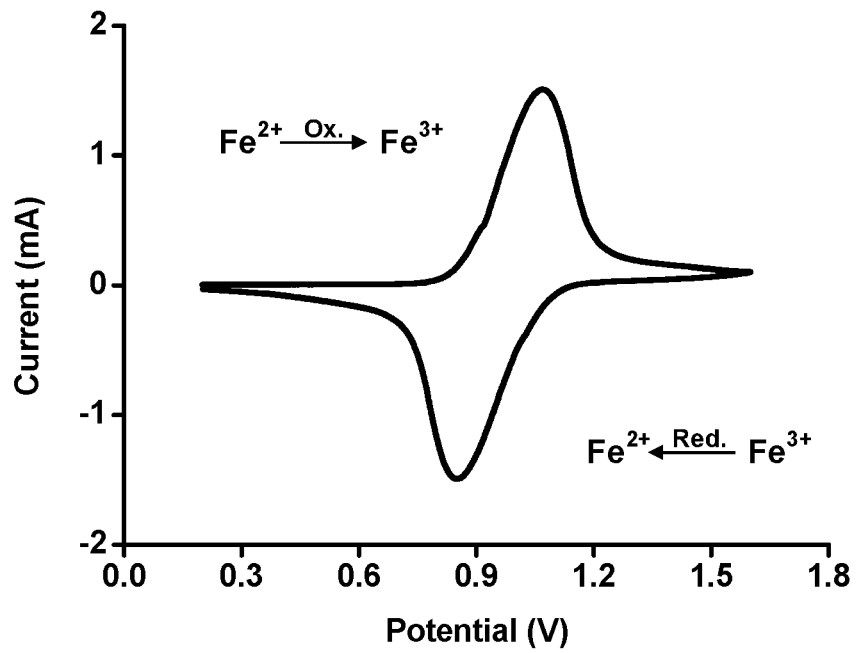
FIG. 14 shows cyclic voltammogram of [Compound 1DB M=Fe, 18 deposition steps, substrate is FTO/glass]. The CV was recorded at a scan rate of 0.1 V/sec, in 0.1 M $TBAPF_6$/ACN.
Figure 15A:
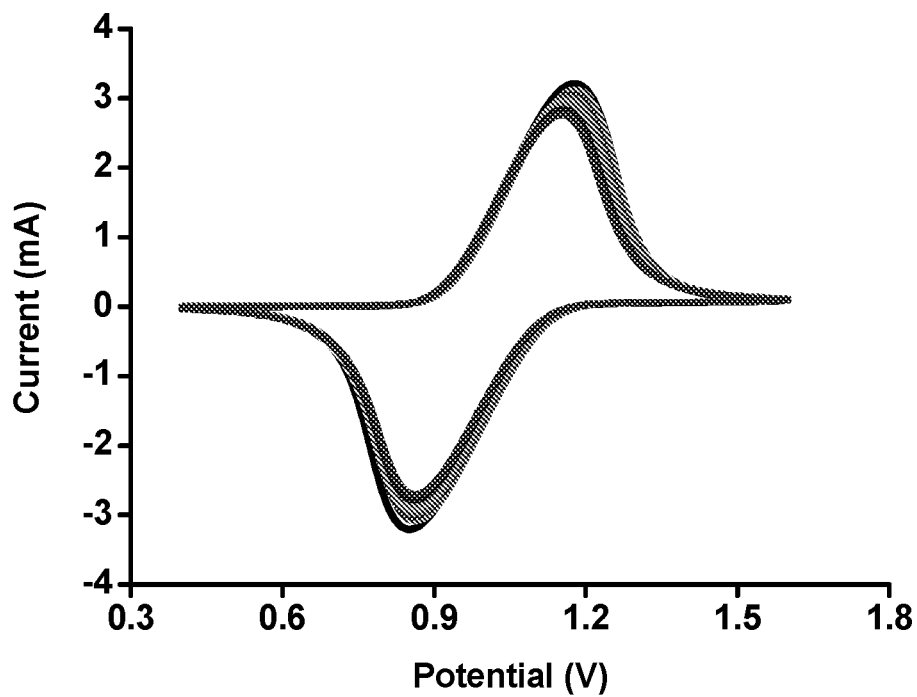
FIGS. 15A-15B illustrate electrochemical stability of [Compound 1DB M=Fe, 18 deposition steps, substrate is FTO/glass].
Figure 15B:
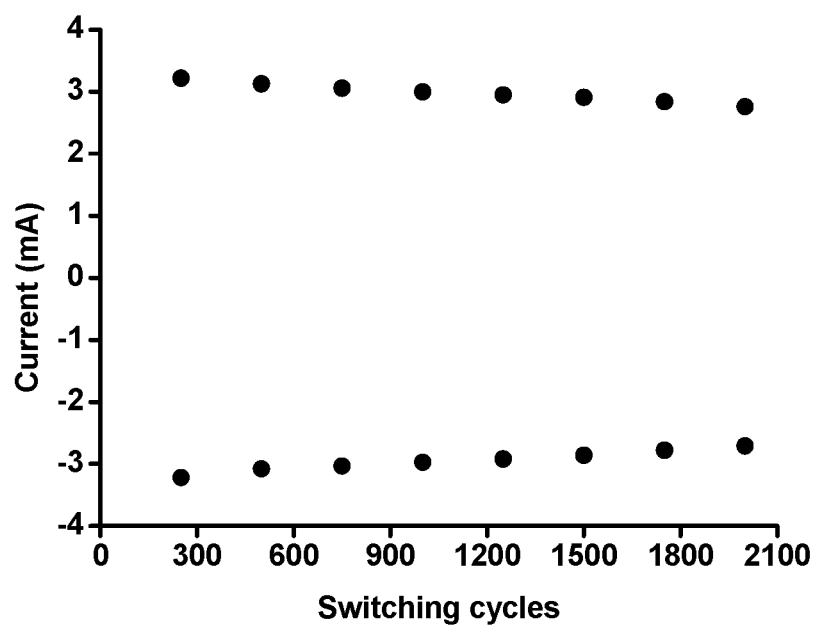

The electrochemical and spectroelectrochemical properties of a film comprising Compound 1DB M=Fe were evaluated using three-electrode cell configuration consisting of the modified FTO substrate, Pt wire and Ag/Ag$^+$ wire as working, counter, and reference electrodes, respectively. CV measurements of the film reveal reversible redox processes of $Fe^{+2}/Fe^{+3}$ pair (FIG. 14). Moreover, the film was cycled for 2000 redox cycles, with a minor decrease in the current (<2%). (FIGS. 15A-15B).

The oxidation and reduction processes that occur in the film are detectable using optical spectroscopy: when the film is oxidized, the intensity of the MLCT band is significantly reduced, resulting in bleaching, while when it is reduced, it has a purple color (FIG. 8A-8B).

Figure 17:
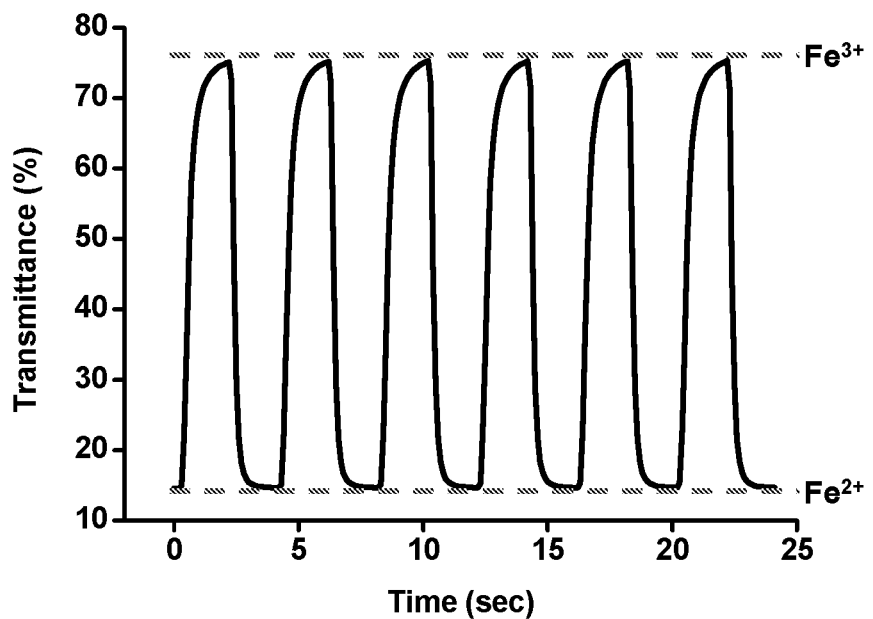
FIG. 17 illustrates spectroelectrochemical behavior illustrates the difference in transmittance values at $\lambda=578$ nm between the oxidized and reduced states of an EC assembly made of Compound 1DB M=Fe as the EC material; and $PdCl_2$ as the linker, on an FTO/glass substrate (18 deposition cycles)

SEC experiments were done by applying double potential steps as a function of time, and recording the optical response at $\lambda$=578 nm as the percentage of transmittance (% T) over time (FIG. 17). The results reveal a very high contrast ratio of 61%. Moreover the film is able to retain 95% of its maximum contrast ratio even after 800 redox cycles.

Figure 18A:
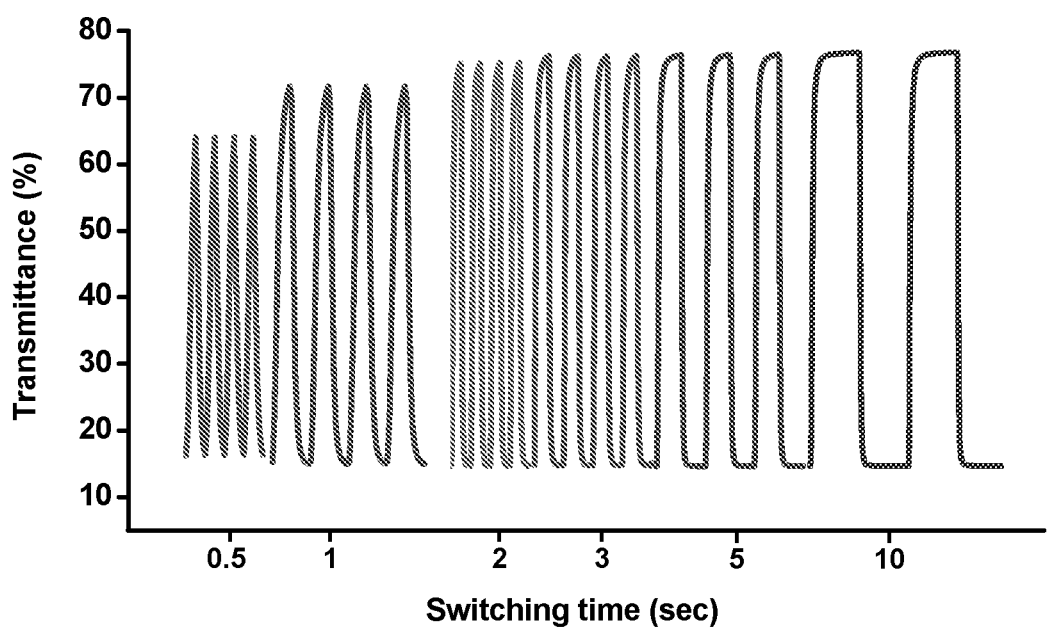
FIGS. 18A-18B illustrate the difference in transmittance of an EC assembly made of Compound 1DB M=Fe as the EC material; and $PdCl_2$ as the linker, on an FTO/glass substrate.
Figure 18B:
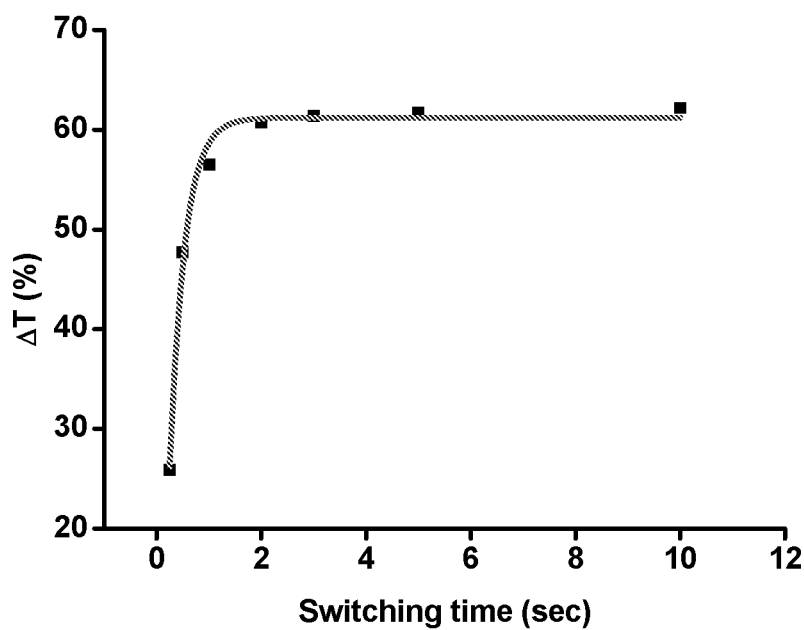

The contrast ratio can be changed as a function of the switching time: as the switching time is shorter, the contrast ratio is lower. However, even for switching time in the sub-second regime, the contrast ratio is still relatively high, when compared to equivalent systems (FIGS. 18A-18B).

Figure 19:
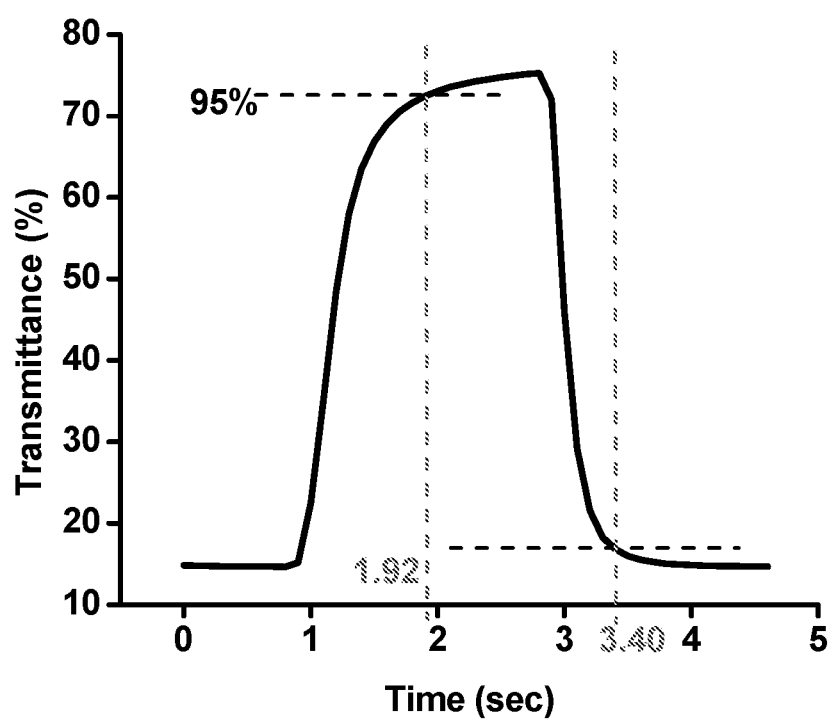
FIG. 19 illustrates the switching efficiency of an EC assembly made of Compound 1DB M=Fe as the EC material; and PdCb as the linker, on a 2×2 cm² FTO/glass substrate. Switching efficiency is defined as the time it takes to the system to achieve 95% of its final optical change. In the discussed system, 95% of the optical change is achieved after 1.92 s in the case of oxidation, while in the case of reduction, 1.48 s are required for 95% of the change to happen.

Switching efficiency is defined as the time it takes for 95% of the maximum contrast ratio to be obtained. It teaches about the time it takes for the system to react to an applied electrical potential. A film based on Compound 1DB M=Fe exhibits switching time of 1.92 seconds for oxidation and 1.48 seconds for reduction (FIG. 19).

Figure 20A:
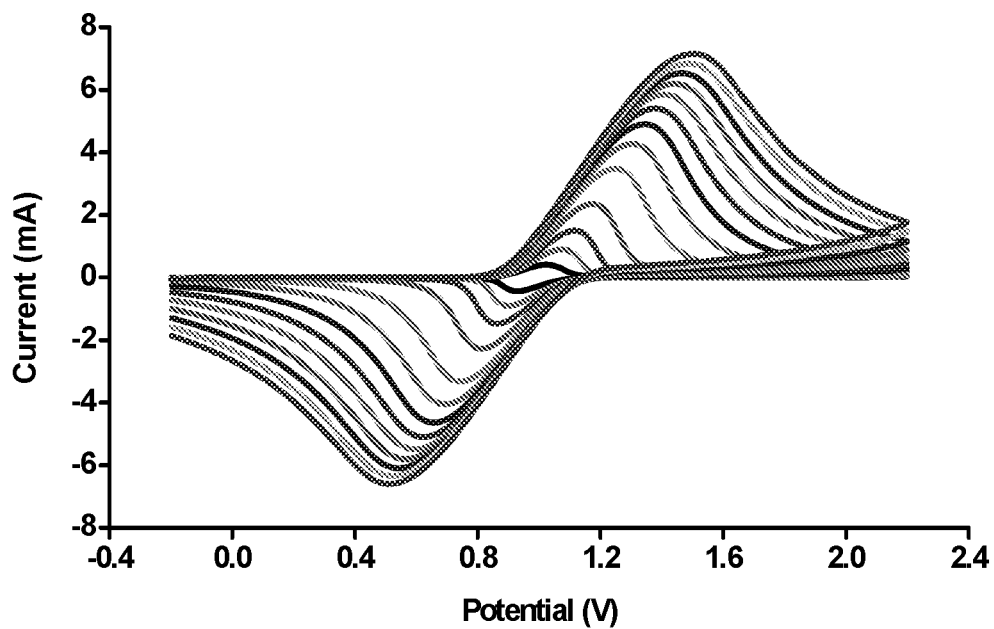
FIGS. 20A-20C illustrate the electrochemical switching at different scan rates of an EC assembly made of Compound 1DB M=Fe as the EC material; and PdCl₂ as the linker, on an FTO/glass substrate. Electrochemical switching refers to the switching between the oxidized state and the reduced state of the material as a result of application of an external potential.
Figure 20B:
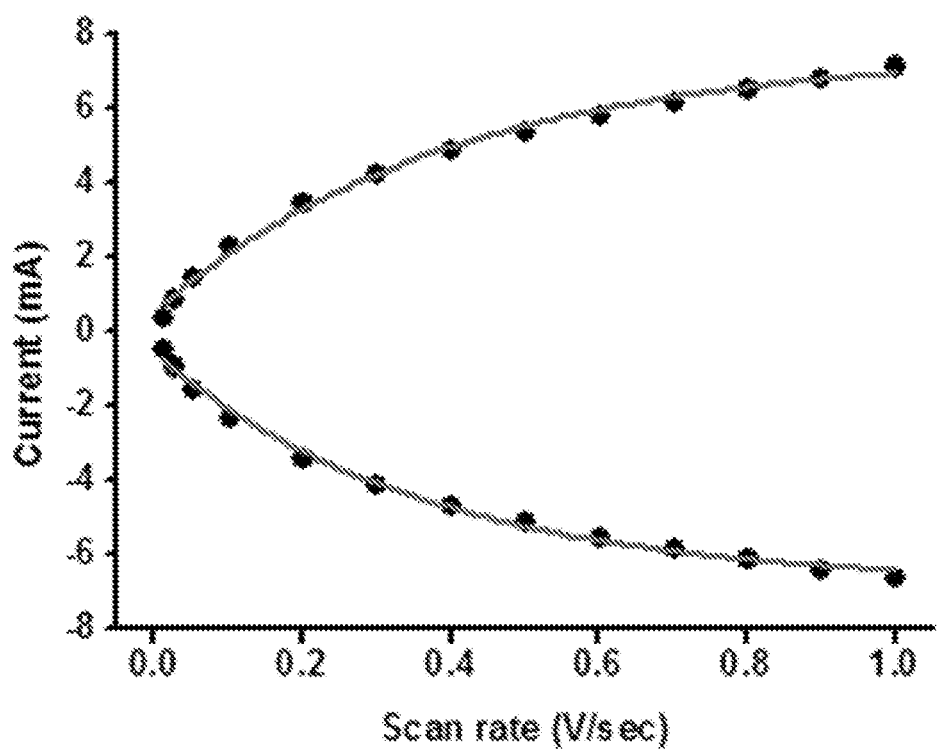
Figure 20C:
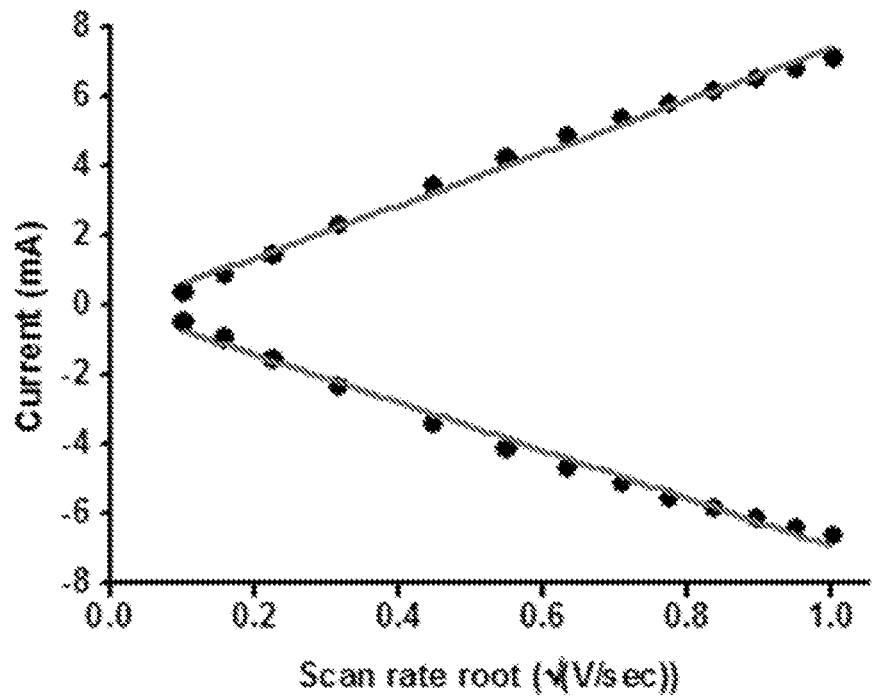

The electron transfer processes can be elucidated by studies of transient responses, such as cyclic voltammetry at different scan rates (FIGS. 20A-20C). CVs were recorded at different scan rates, and the obtained results are different than what is known for monolayer systems: The results reveal exponential dependence of the current on the scan rate, and a linear dependence of the current on the scan rate root. These trends, which indicate a diffusion controlled process, are different than what is known for monolayers systems, or for what was seen in a dip-coating systems that were previously investigated. However, these trends are in agreement with systems of polymer films with comparable thickness.

Figure 21A:
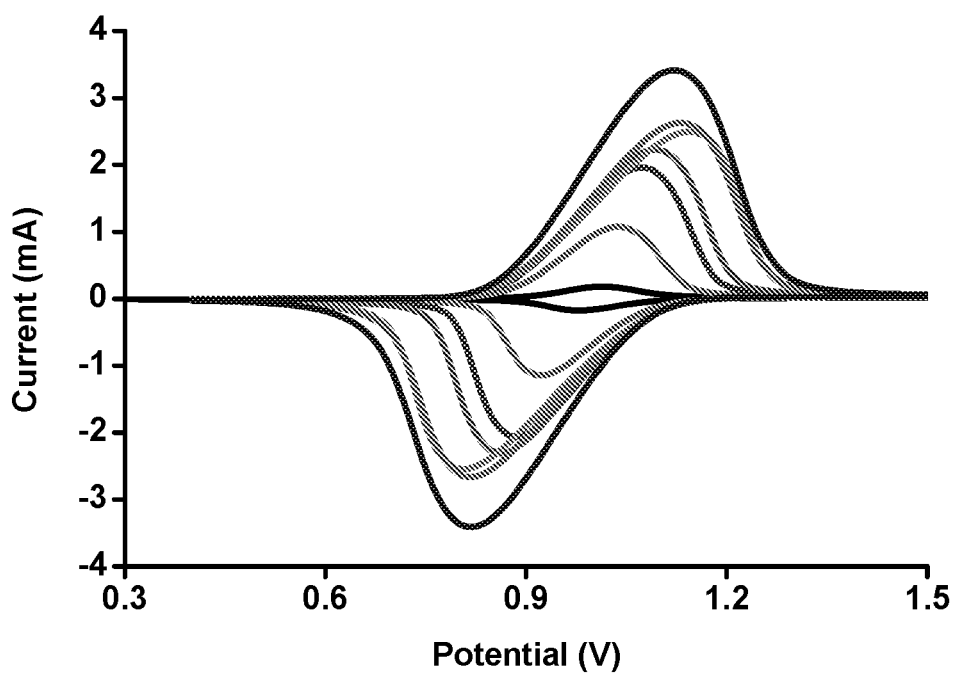
FIGS. 21A-21B illustrate the electrochemical dependence of EC assemblies made of Compound 1DB M=Fe as the EC material; and PdCl₂ as the linker, on a 2×2 cm² FTO/glass substrates.
Figure 21B:
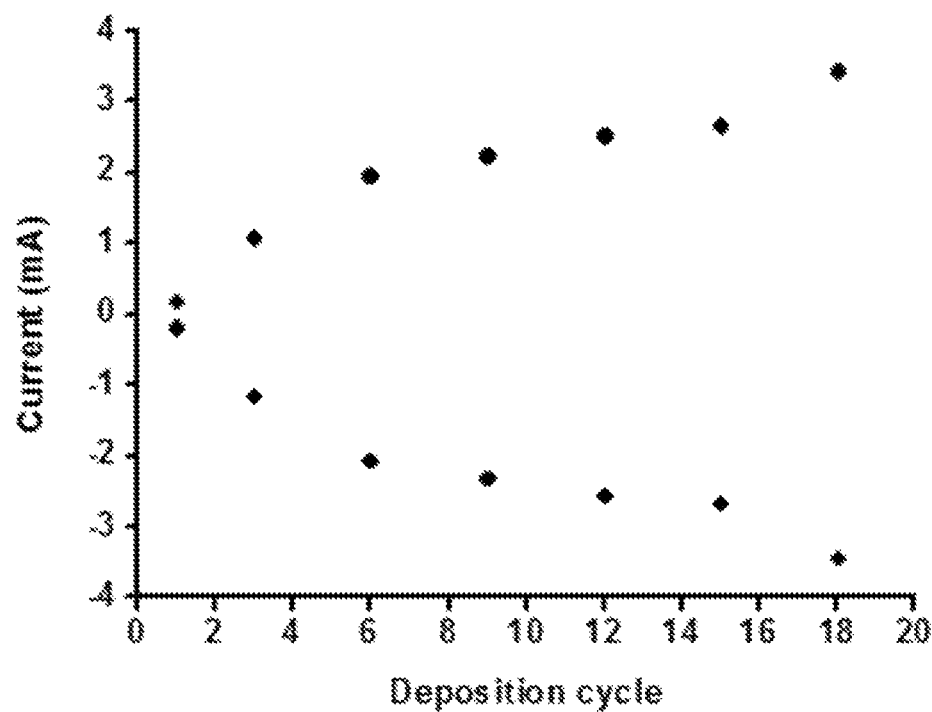
Figure 22A:
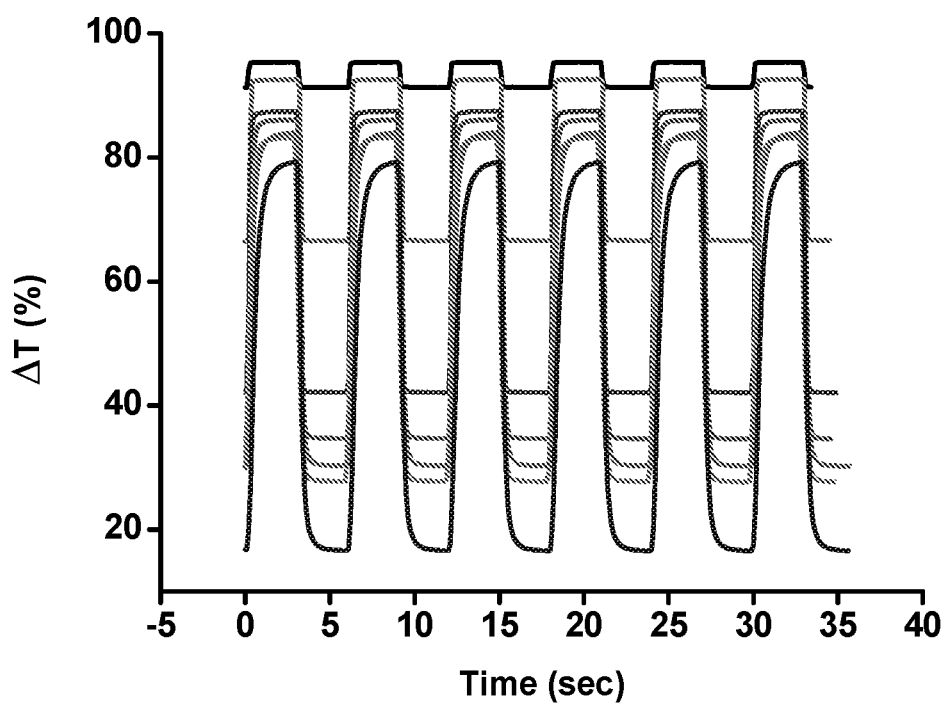
FIGS. 22A-22B illustrate the spectroelectrochemical behavior of EC assemblies made of Compound 1DB M=Fe as the EC material; and PdCl₂ as the linker, on a 2×2 cm² FTO/glass substrates.
Figure 22B:
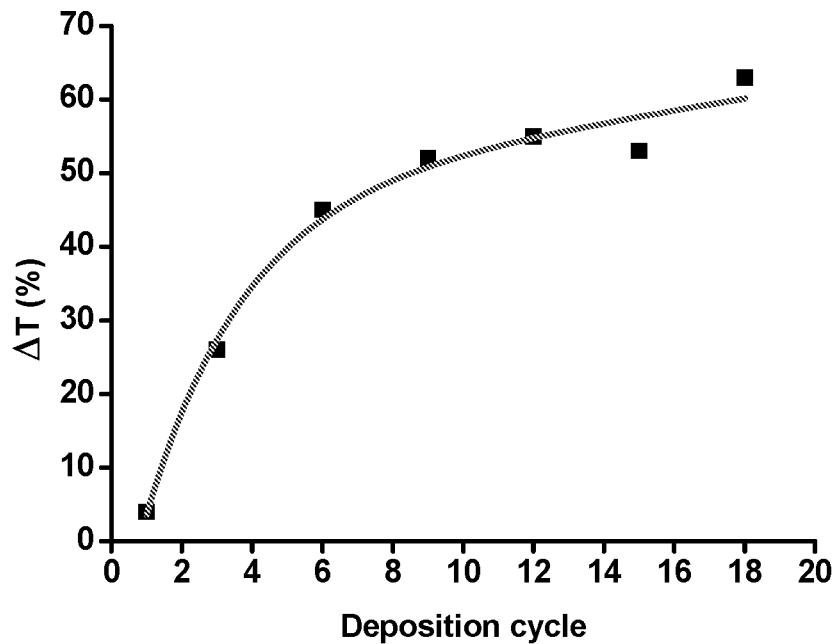
Figure 23A:
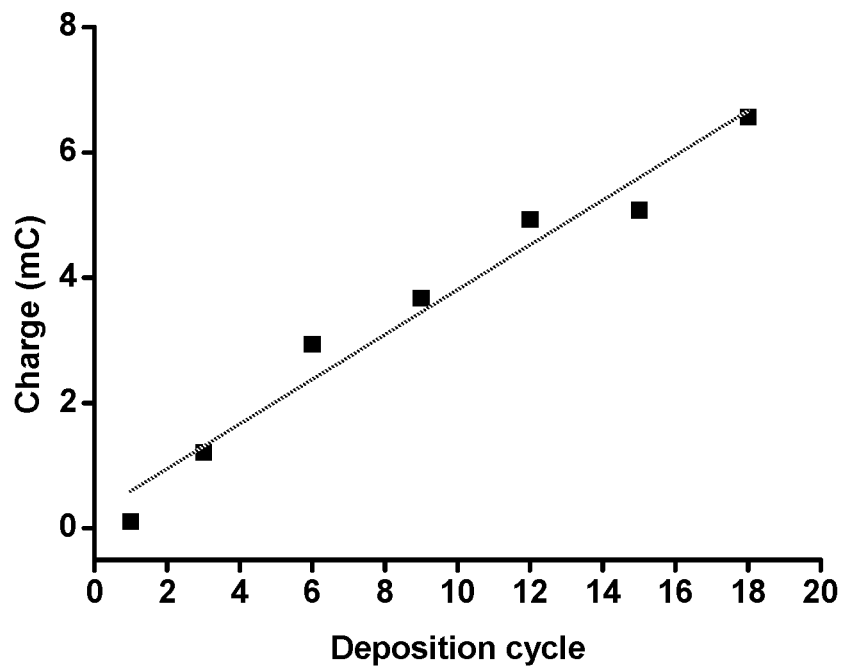
FIGS. 23A-23B illustrate spectroelectrochemical behavior of [Compound 1DB M=Fe|1-18 FTO/glass]. Film size: 2 cm×2 cm.
Figure 23B:
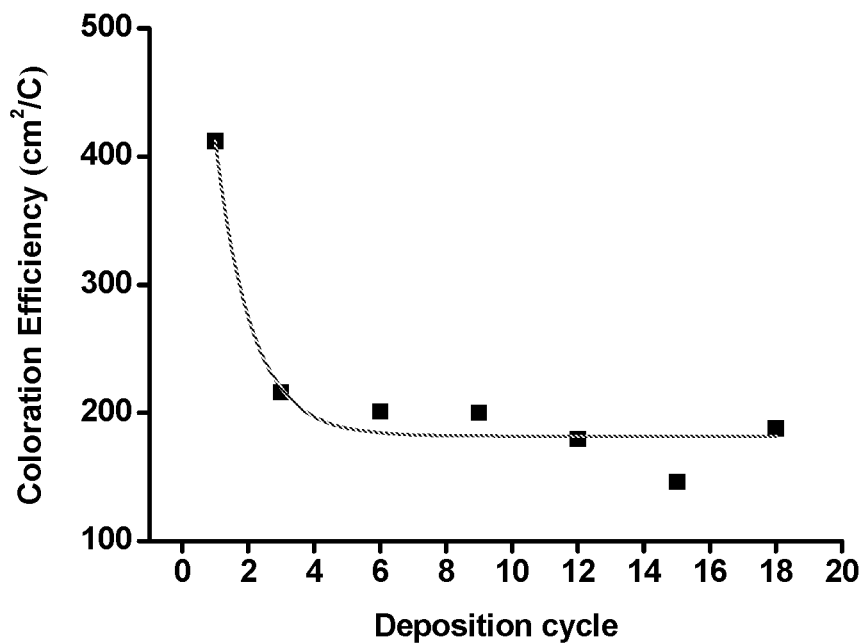

Measuring the electrochemical and spectroelectrochemical properties at different deposition cycles gives information about the structure and the internal organization of the film (FIGS. 21-23).

1:3.2.2 Electrochemical Characteristics of Compound 2DB M=Fe

Figure 24:
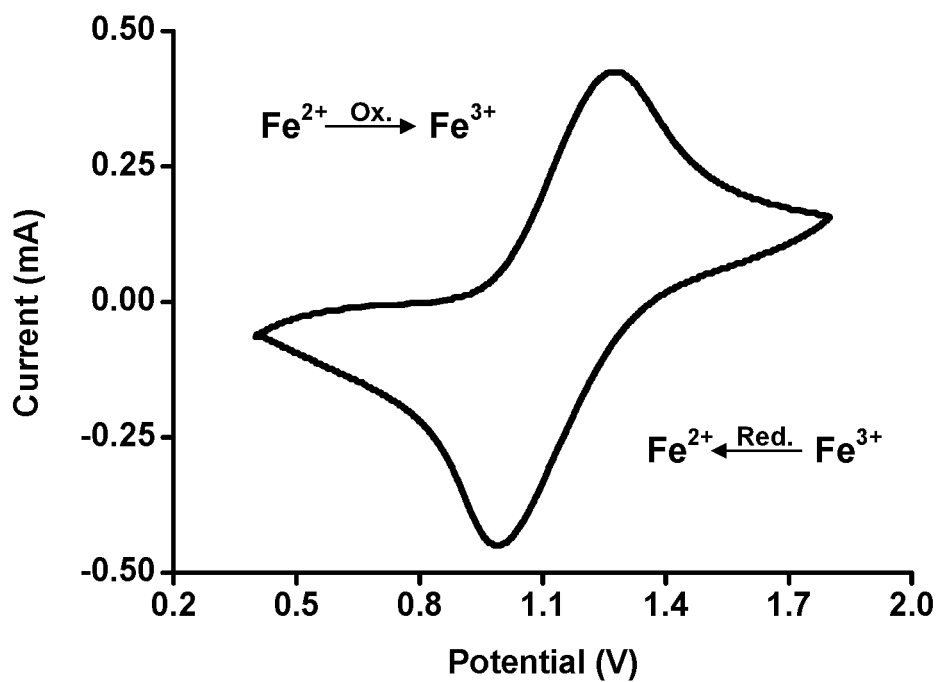
FIG. 24 shows cyclic voltammogram of [Compound 2DB M=Fe|18|FTO/glass]. The CV was recorded at a scan rate of 0.1 V/sec, in 0.1 M TRAPF₆/ACN.
Figure 25:
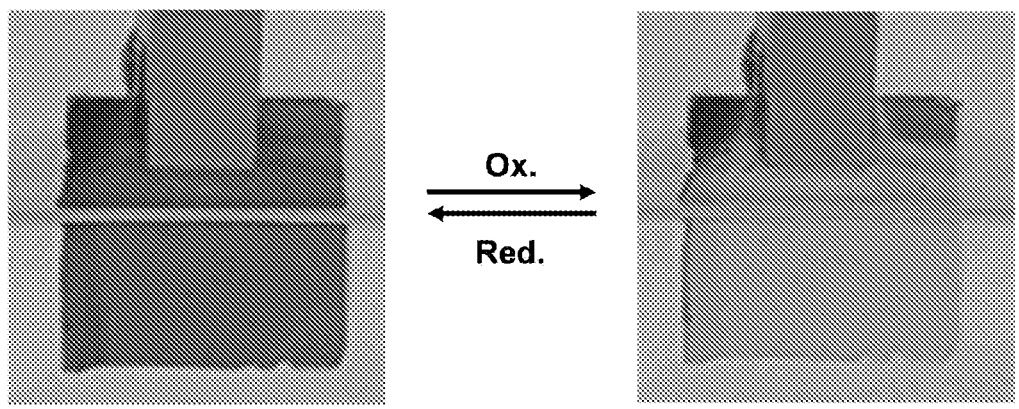
FIG. 25 illustrates photographs of the colored and bleached states of a 2×2 cm² EC assembly made of Compound 2DB M=Fe as the EC material; and PdCl₂ as the linker, on FTO/glass, where the electrochemical switching was performed by applying double potential steps at a potential window of 0.2-1.8V.

The electrochemical and spectroelectrochemical properties of a film comprising Compound 2DB M=Fe were evaluated using three-electrode cell configuration consisting of the modified FTO substrate; Pt wire and Ag/Ag$^+$ wire as working, counter, and reference electrodes, respectively. CV measurements of the film reveal reversible redox processes of $Fe^{+2}/Fe^{+3}$ pair (FIG. 24). The oxidation and reduction processes that occur in the film are detectable using optical spectroscopy: when the film is oxidized, the intensity of the MLCT band is significantly reduced, resulting in bleaching, while when it is reduced, it has a black color (FIG. 25).

Figure 26A:
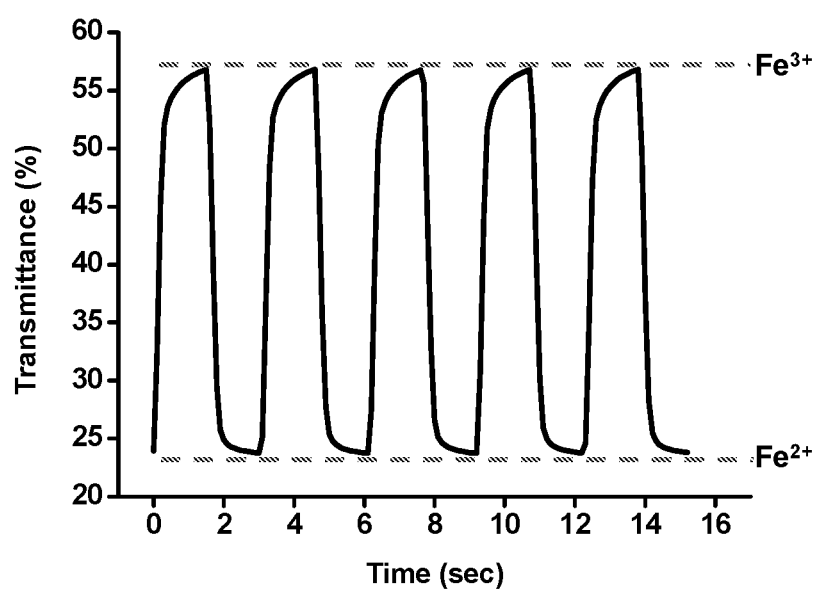
FIGS. 26A-26B illustrate the spectroelectrochemical behavior of an EC assembly made of Compound 2DB M=Fe as the EC material; and PdCl₂ as the linker, on an FTO/glass substrate.
Figure 26B:
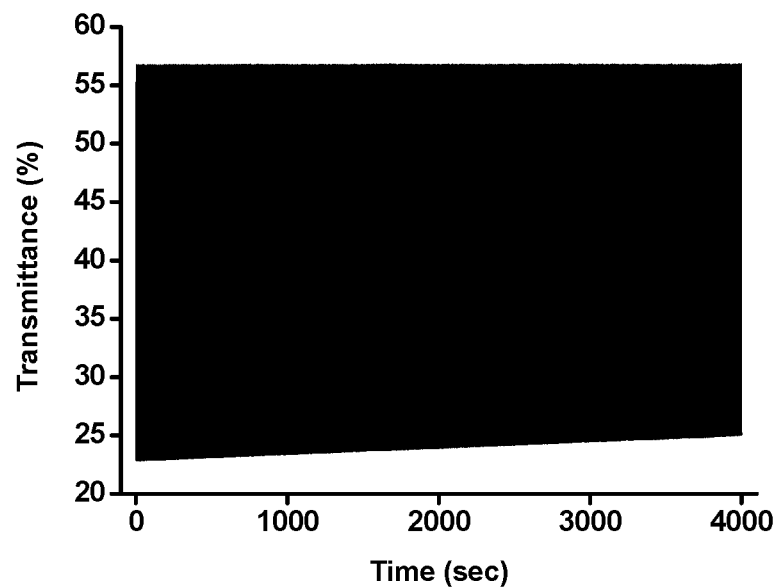
Figure 27A:
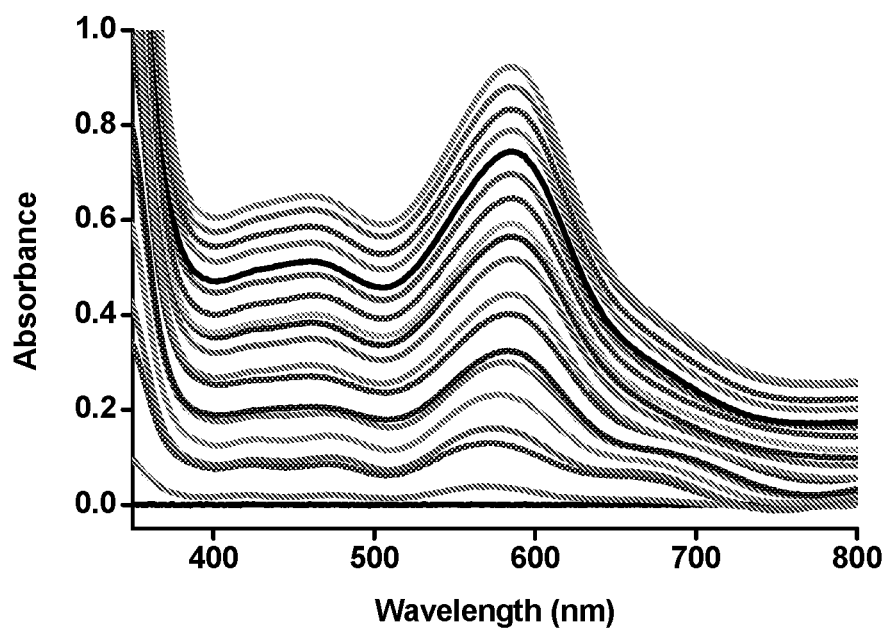
FIGS. 27A-27F illustrate the film growth of EC assemblies made of a mixture of Compounds 1DB M=Fe and 2DB M=Fe.
Figure 27B:
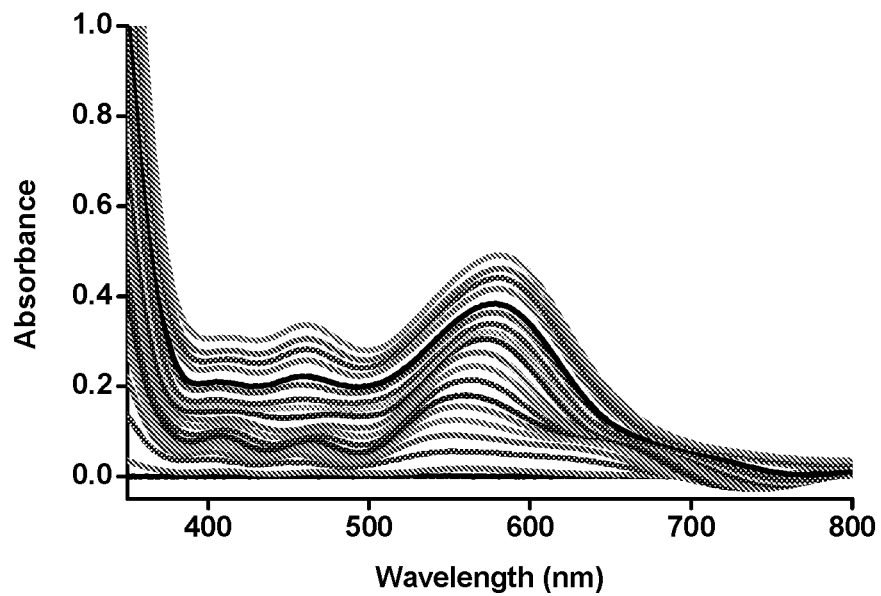
Figure 27C:
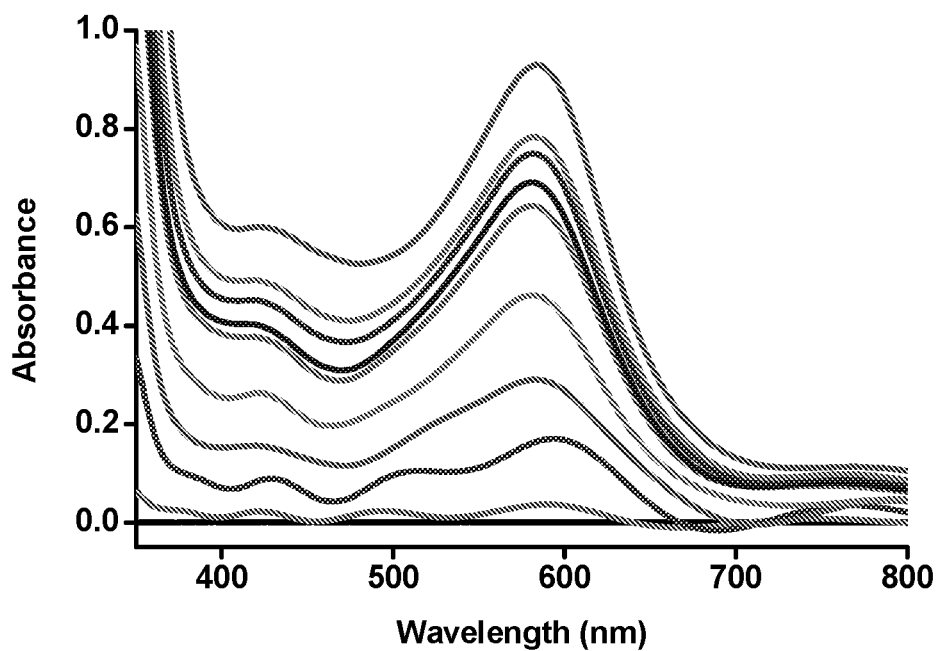
Figure 27D:
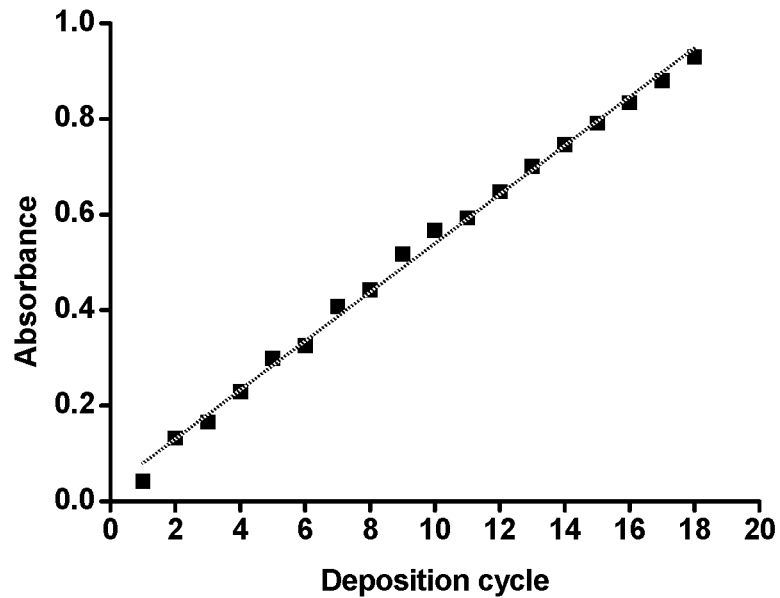
Figure 27E:
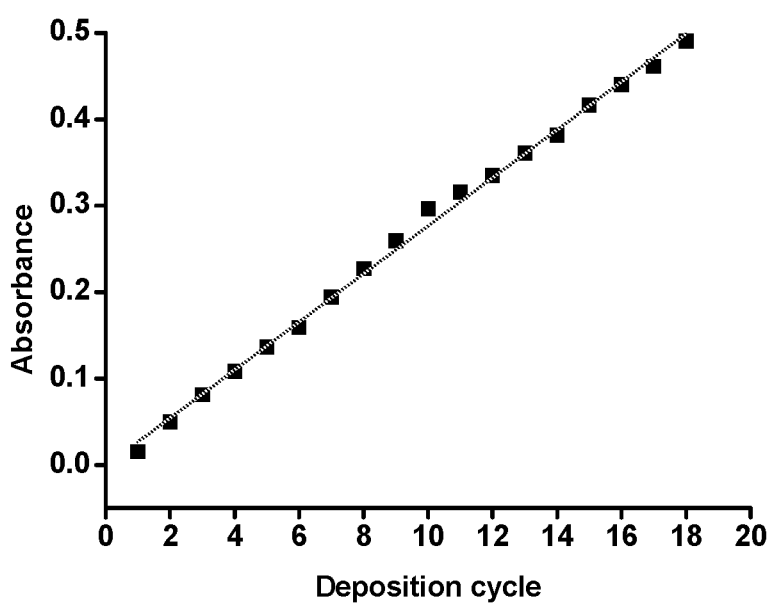
Figure 27F:
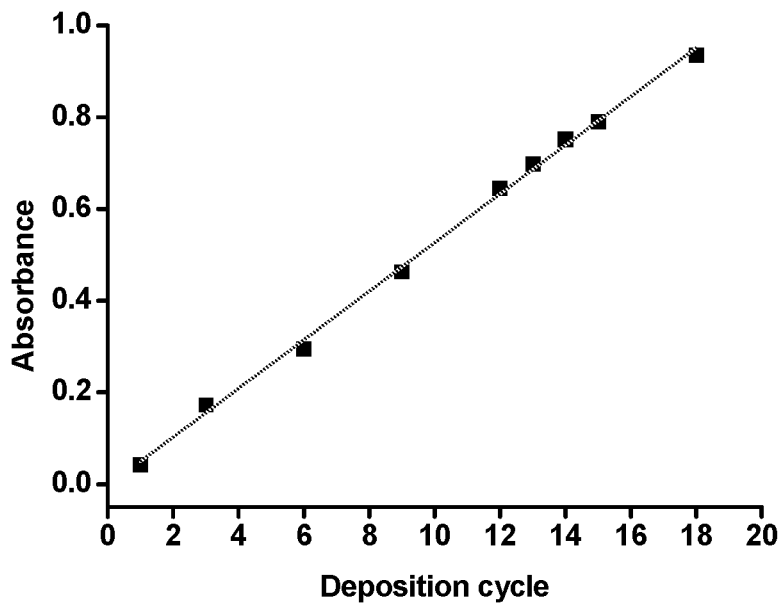
Figure 28A:
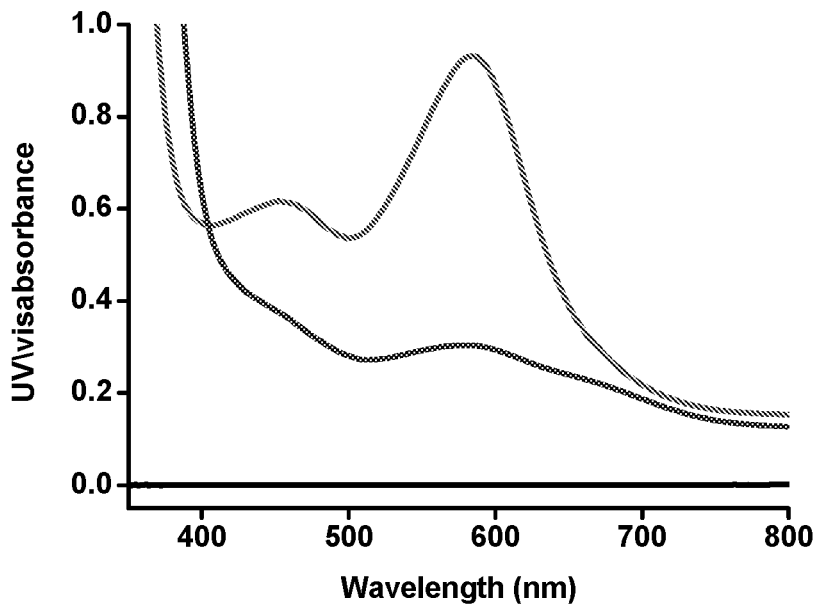
FIGS. 28A-28C illustrate the electrochemical switching of EC assemblies made of a mixture of Compounds 1DB M=Fe and 2DB M=Fe.
Figure 28B:
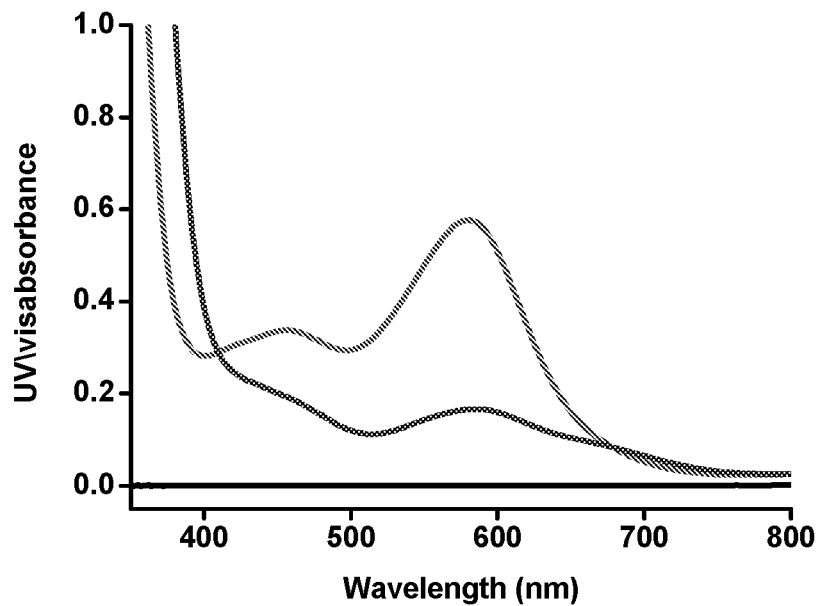
Figure 28C:
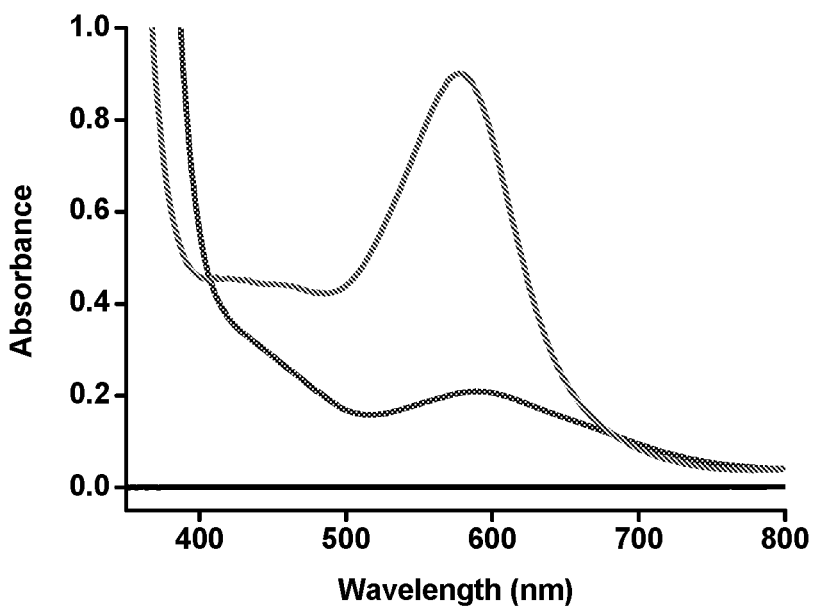
Figure 29A:
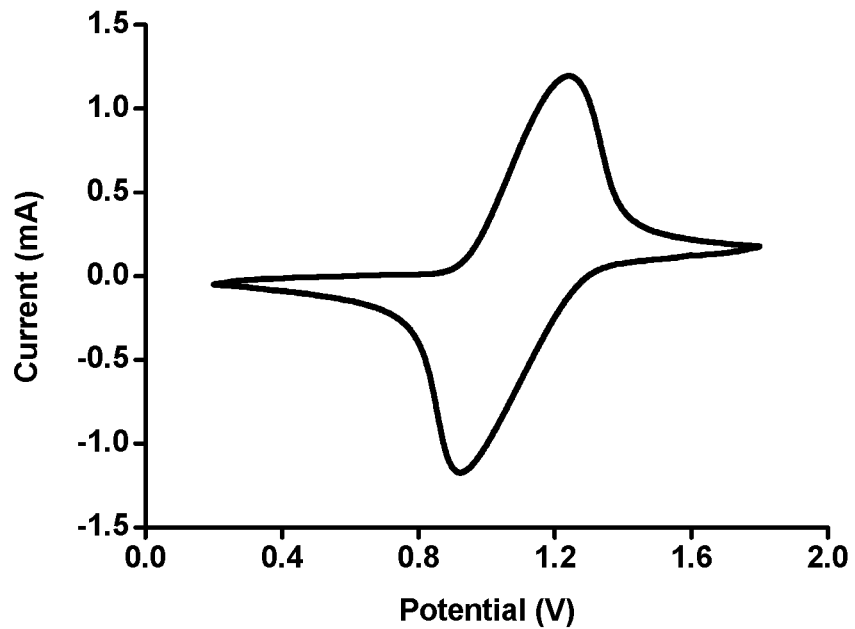
FIGS. 29A-29F illustrate the spectroelectrochemical behavior of EC assemblies m made of a mixture of Compounds 1DB M=Fe and 2DB M=Fe.
Figure 29B:
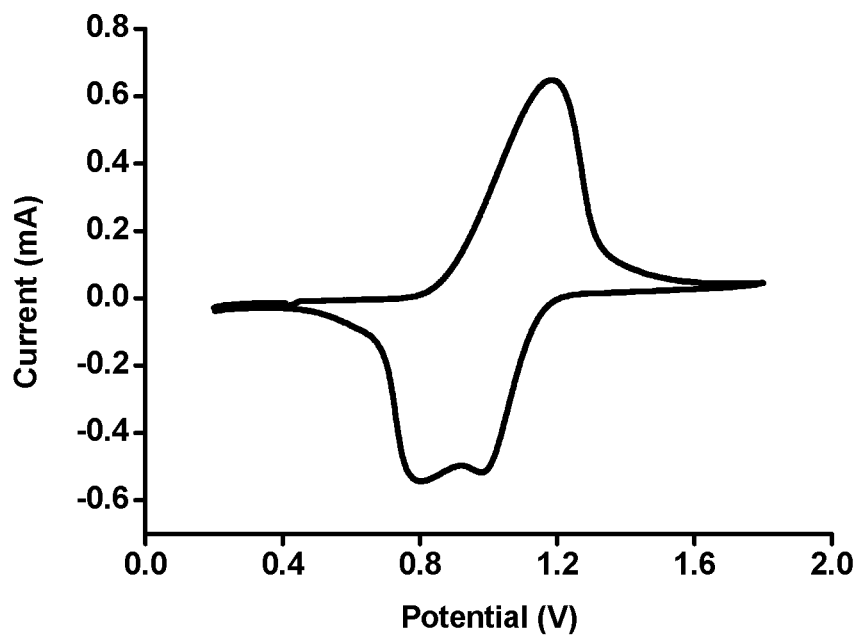
Figure 29C:
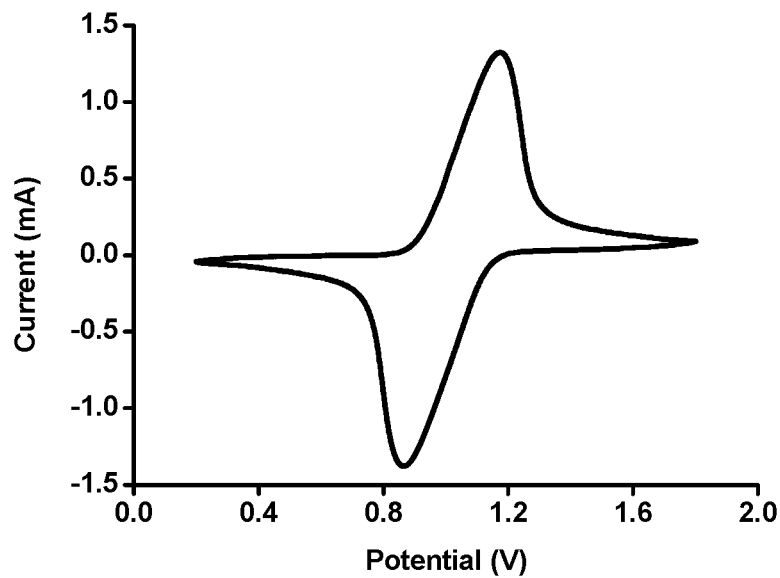
Figure 29D:
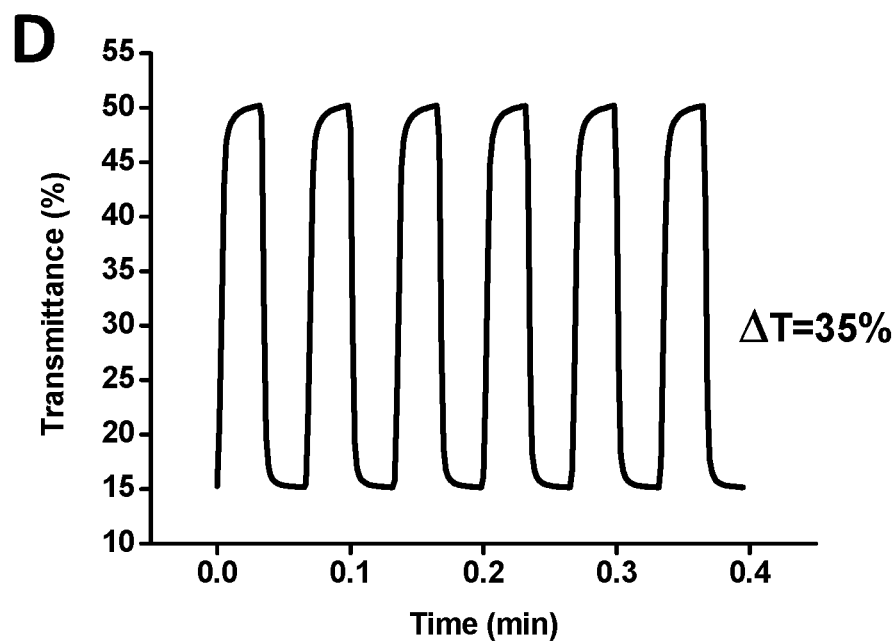
Figure 29E:
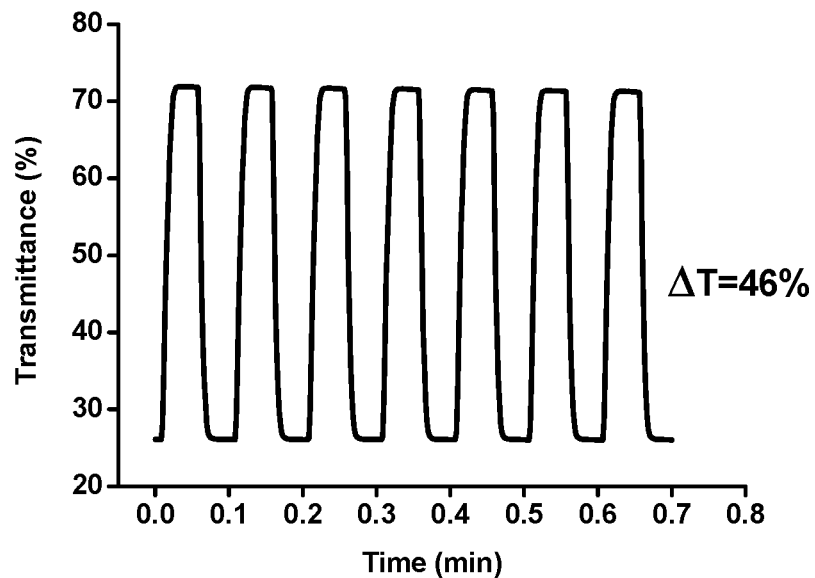
Figure 29F:
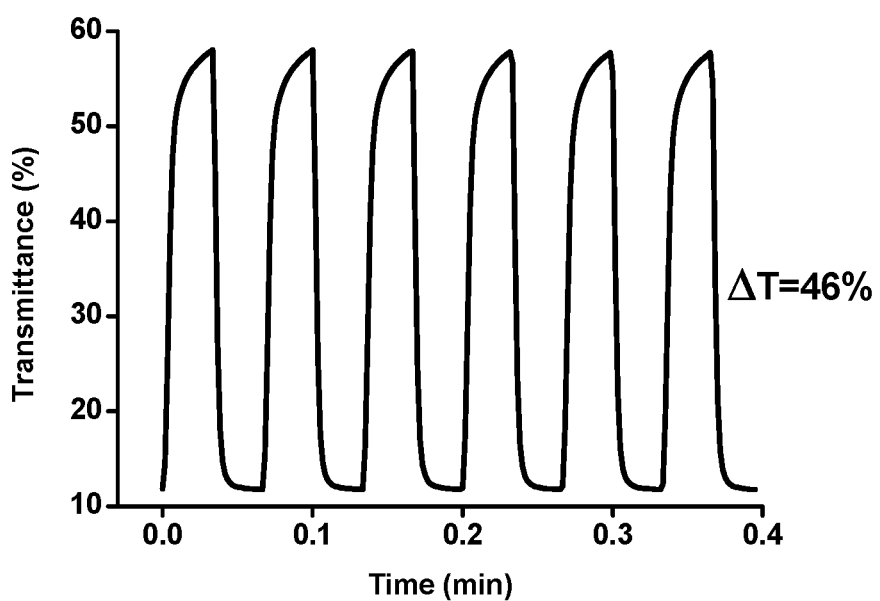
Figure 30A:
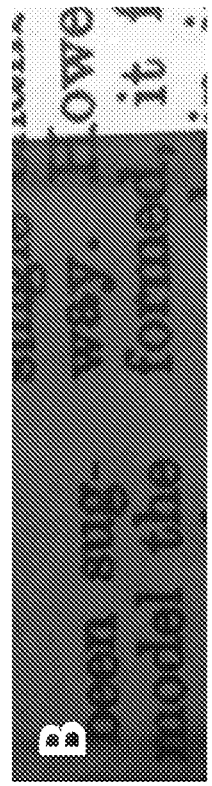
FIGS. 30A-30D illustrate the color of assemblies composed of combinations of Compounds 1DB M=Fe and 2DB M=Fe after 18 deposition cycles, using PdCl₂ as the linker.
Figure 30B:
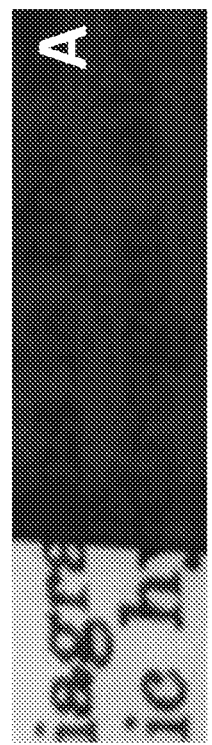
Figure 30C:
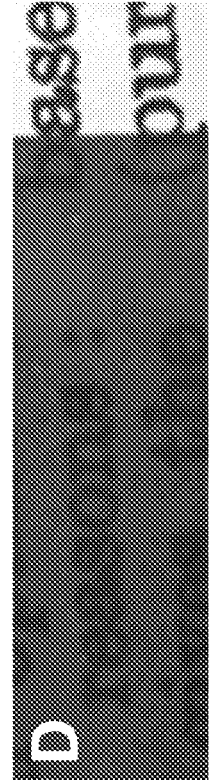
Figure 30D:
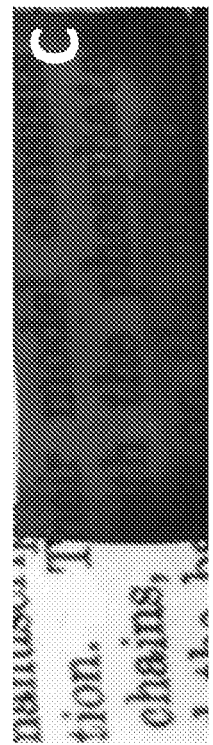

SEC experiments were done by applying double potential steps as a function of time, and recording the optical response at $\lambda$=598 nm as the percentage of transmittance (% T) over time. The results reveal contrast ratio of 33%. Moreover the film is able to retain 95% of its maximum contrast ratio even after 1000 redox cycles (FIG. 26B).

1.3.2.3 Electrochemical Characteristics of Mixed Systems

Figure 16:
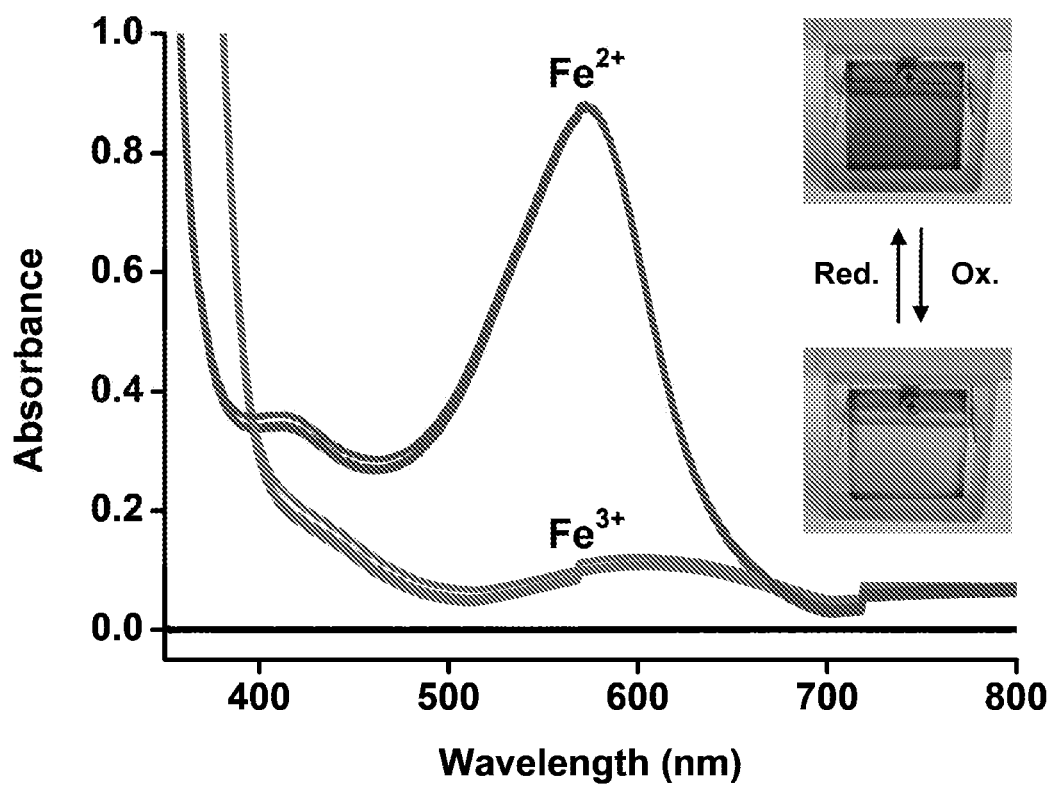
FIG. 16 illustrates electrochemical switching of an EC assembly made of Compound 1DB M=Fe as the EC material; and $PdCl_2$ as the linker, on an FTO/glass substrate (18 deposition cycles); Optical absorbance spectra corresponding to the oxidized (gray) and reduced (purple) states of the assembly. The electrochemical switching was performed by applying double potential steps at a potential window of 0.2-1.8 V. Inset: photographs of the colored and the bleached states of 4 cm×4 cm film.

The previous sub-chapter described films based on separate systems of either Compound 1DB M=Fe or Compound 2DB M=Fe. This chapter presents films based on mixed systems of the two compounds. The motivation behind mixing the two compounds arises from the fact that a system based on Compound 1DB M=Fe is more opaque (based on its contrast ratio, see FIGS. 16-17), while a system based on Compound 2DB M=Fe is more stable and has a black color, which is a color of interest in the EC industry. Thus, combination of the two compounds enhances the overall electro-chromic performance of the system in some embodiments.

Mixing of two components into one system can be obtained in various ways: alternating depositions of each compound, either by alternate deposition of one layer of each compound or deposition in block configuration: a block of one compound followed by a block of the other compound. In the latter manner, the sizes of blocks can be equal or can vary in favor of one compound over the other. The size of each block can be controlled by the number of deposition cycles for each block.

Another way of deposition is by using a mixed solution of the two compounds in equal or different concentrations. The latter two systems (block and mixed-solution) were fabricated using the herein disclosed fabrication method.

The fabrication process using mixed solutions included alternating depositions of solutions of $PdCl_2(PhCN)_2$ and a solution of Fe polypyridyl complexes mixture (compounds 1DB M=Fe and 2DB M=Fe in equal amount). The block deposition utilized separated solutions of each complex.

Both methods relied on the use of spin coating-LBL approach. In this example 18 deposition cycles were fabricated and according to UV/vis absorption, the growth trend was found to be linear, similar to the separated systems wherein only one complex has been used (FIGS. 27A-27F).

Electrochemical and SEC analysis show higher contrast ratio for the block systems, however when considering the obtained color, the mixed system seems the darkest (FIGS. 28A-28C, FIGS. 29A-29F, FIGS. 30A-30D).

1.4 Films on Flexible Support—Fabrication and Characterization

The need for flexible EC films arose in the past few years due to their potential applications in the electronic industry, e.g. flexible displays. This kind of films is also interesting as it may allow installation of EC films on existing structures, which will reduce production costs compared to newly formed structures.

In this example, ITO/PET substrates (10 ohm/cm$^2$) were purchased commercially. As was described above, ITO has unique transparent and conducting properties, which results in low electrical resistivity, and high transmission. When deposited on PET, a flexible transparent electrode is obtained.

Figure 31A:
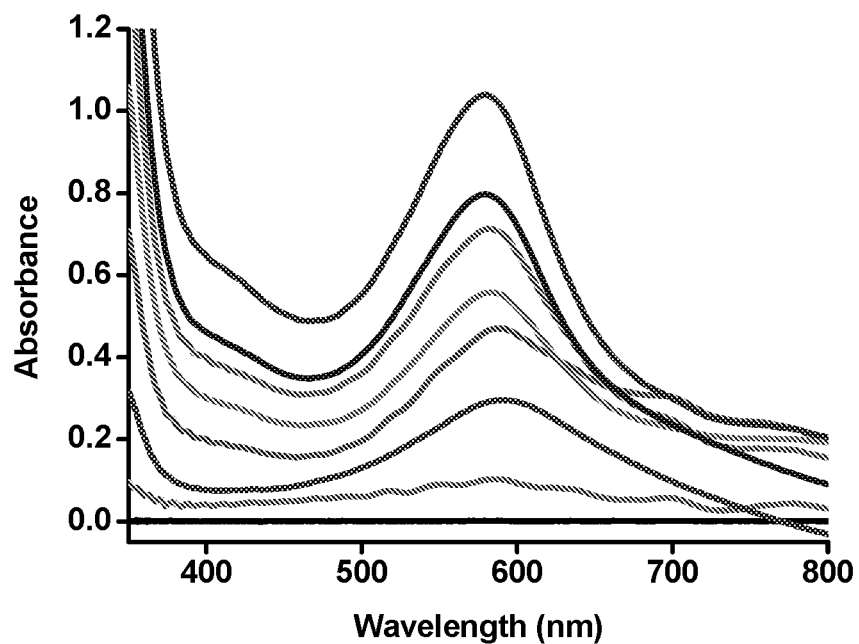
FIGS. 31A-31B illustrate the growth behavior of EC assembly composed of Compound 1DB M=Fe on ITO/PET.
Figure 31B:
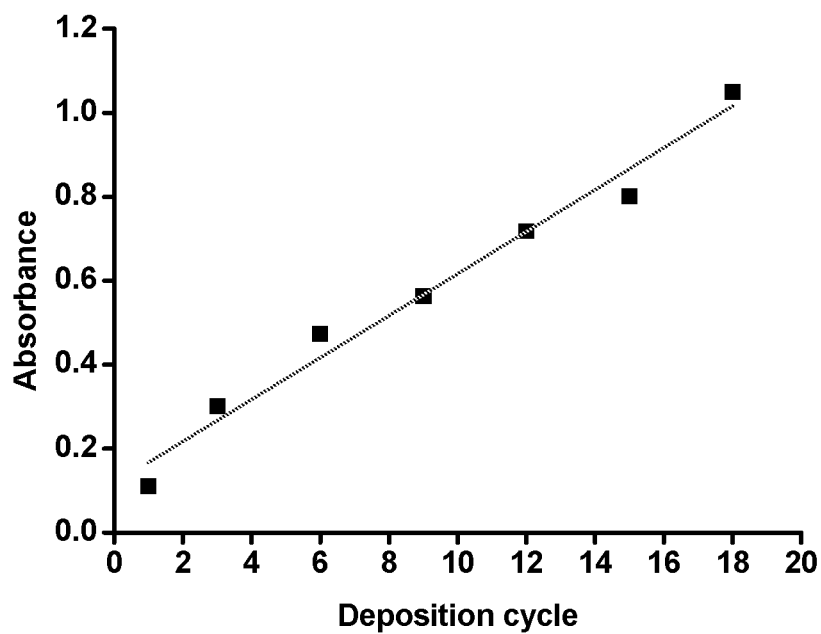

ITO/PET substrates were cleaned prior to further deposition steps. The cleaning procedure involved rinsing with ethanol, followed by immersion in acetone. The substrates were dried under air stream. Compound 1DB M=Fe was deposited according to the described film fabrication method. As disclosed herein. Compound 1DB M=Fe has a characteristic metal to ligand charge transfer (MLCT) band at λ=578 nm that is increasing linearly as the number of deposition cycles increases. (FIGS. 31A-31B).

Figure 32:
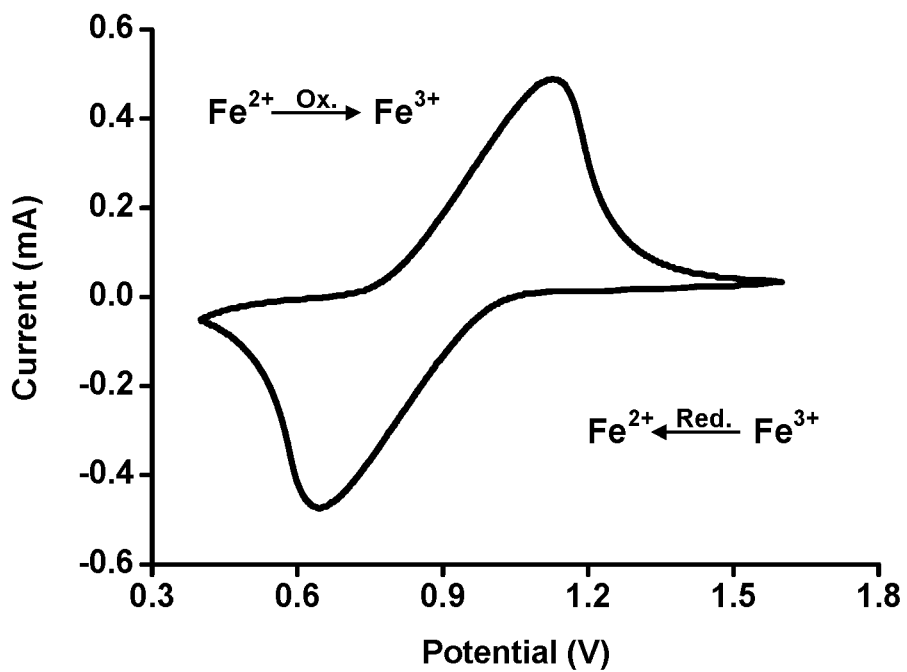
FIG. 32 illustrates the CV measurements of an EC assembly composed of Compound 1DB M=Fe on a flexible ITO/PET substrate recorded at a scan rate of 0.1 V/sec in 0.1 M TRAM₆/ACN.
Figure 33A:
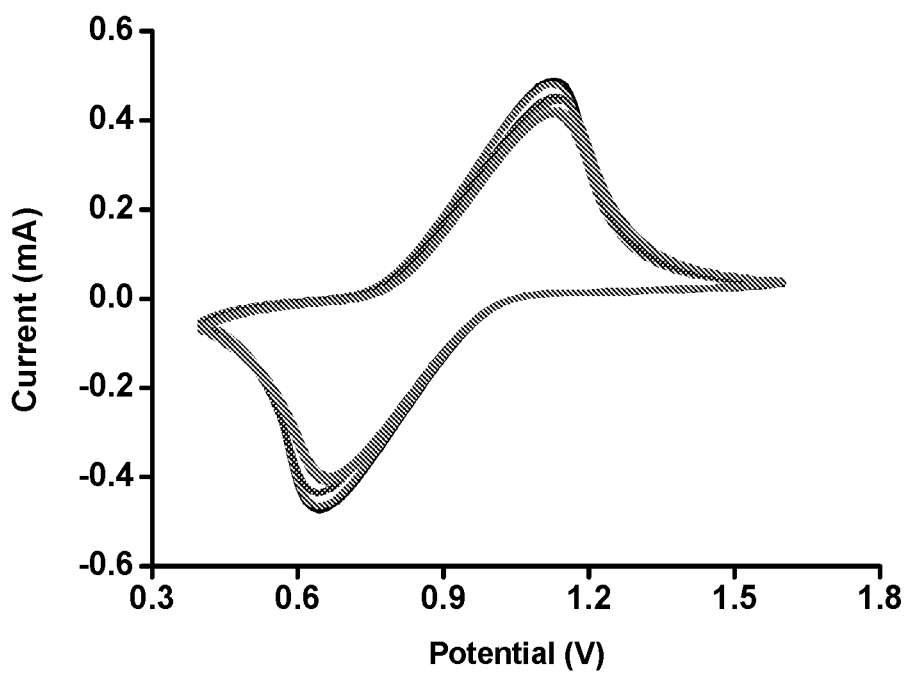
FIGS. 33A-33B illustrate the electrochemical stability of an EC assembly composed of Compound 1DB M=Fe on an ITO/PET substrate.
Figure 33B:
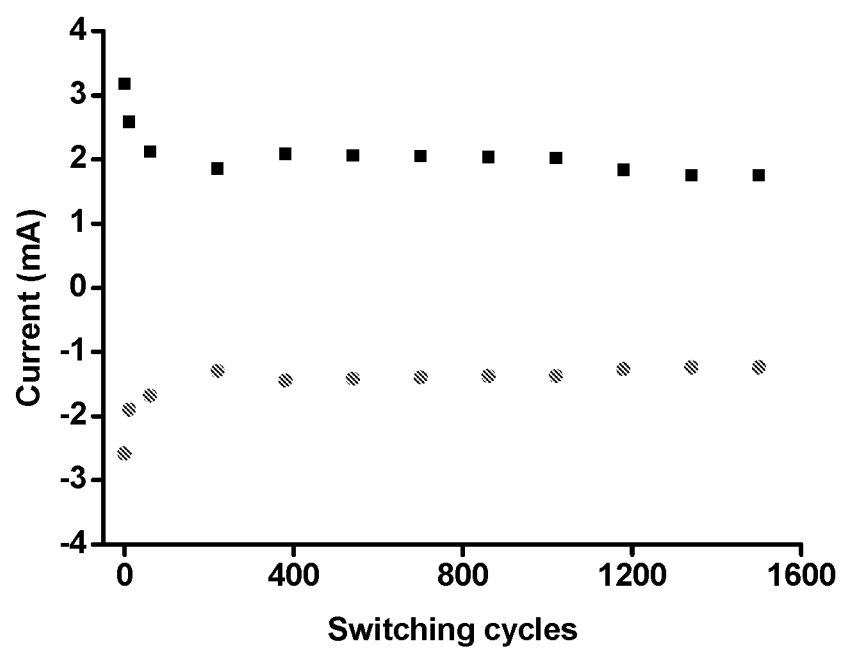
Figure 34:
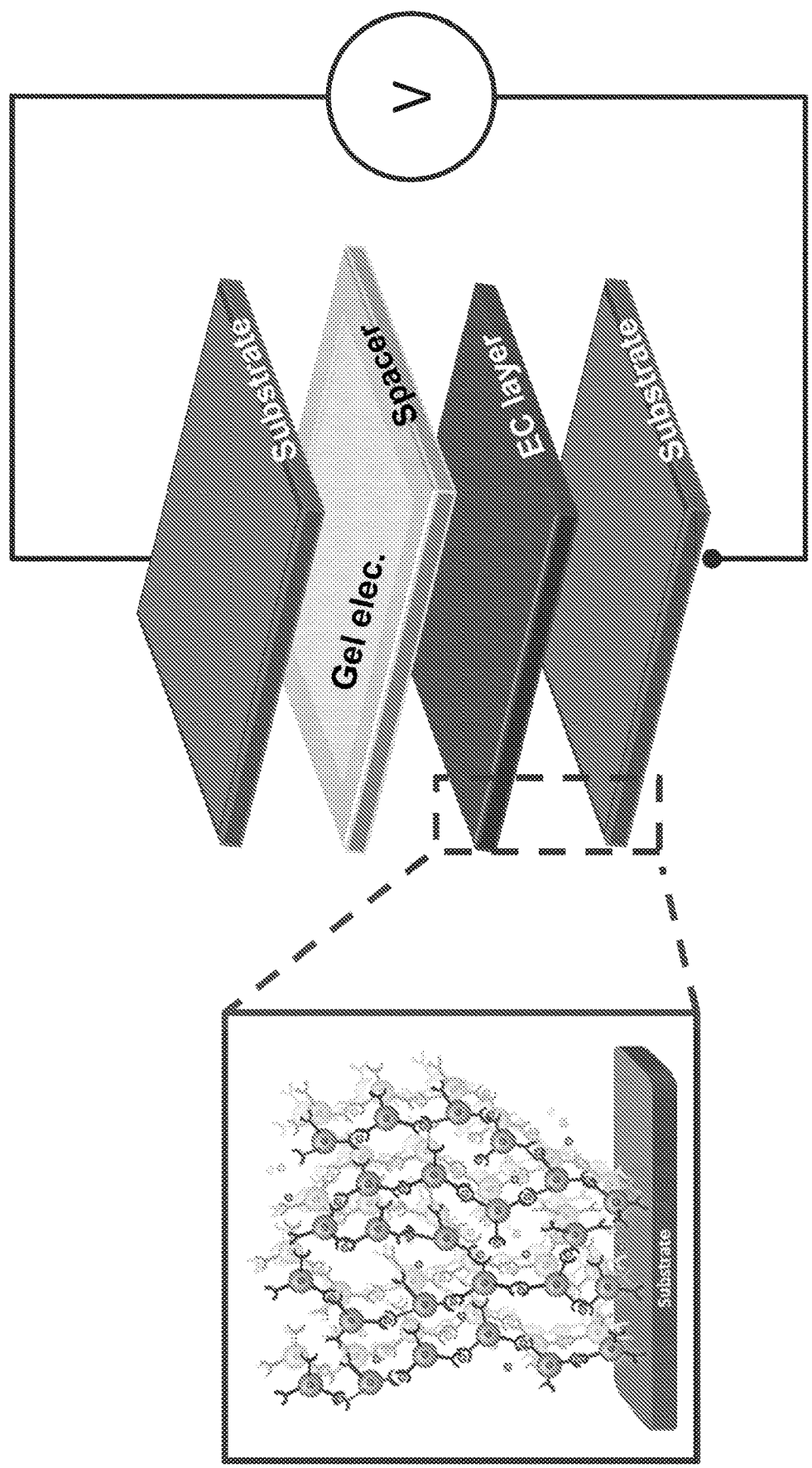
FIG. 34 is a schematic representation of an electrochromic device composed of materials of the invention where the substrates are transparent conducting electrodes and the spacer is 3M 9088 double sided tape.
Figure 35:
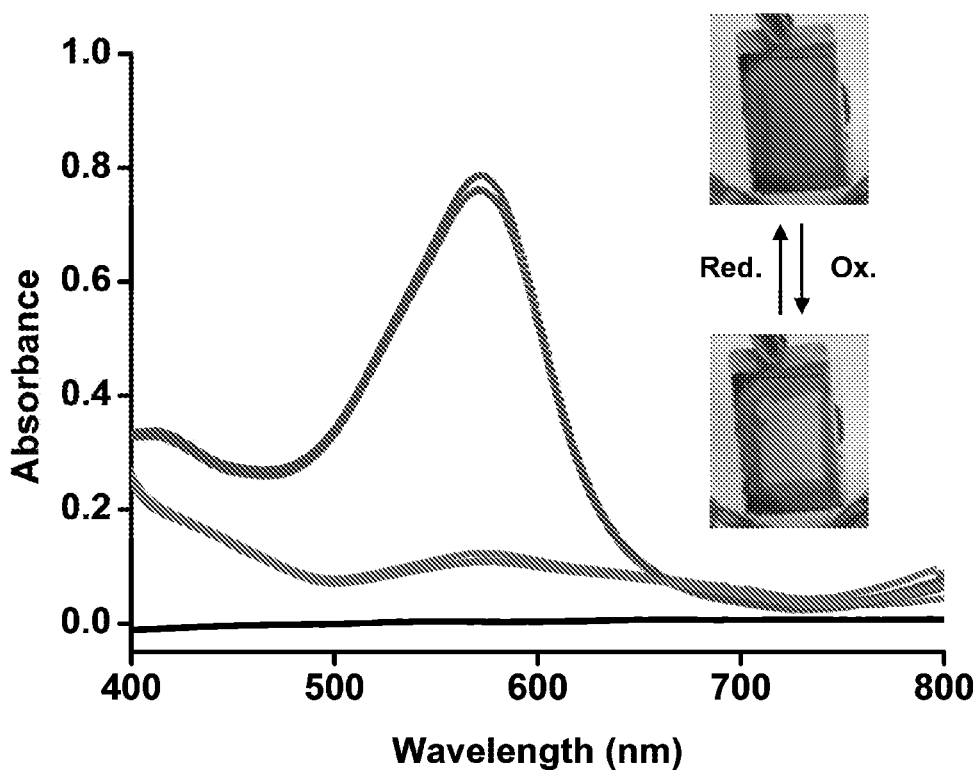
FIG. 35 illustrates the electrochemical switching of the electrochromic device, where the working electrode is an EC assembly composed of Compound 1DB M=Fe deposited on FTO/glass (18 deposition cycles) and the counter electrode is a bare FTO substrate. In the optical absorbance spectra the oxidized state, which is colorless is represented in gray and the reduced state, which is purple, is represented in purple.
Figure 36A:
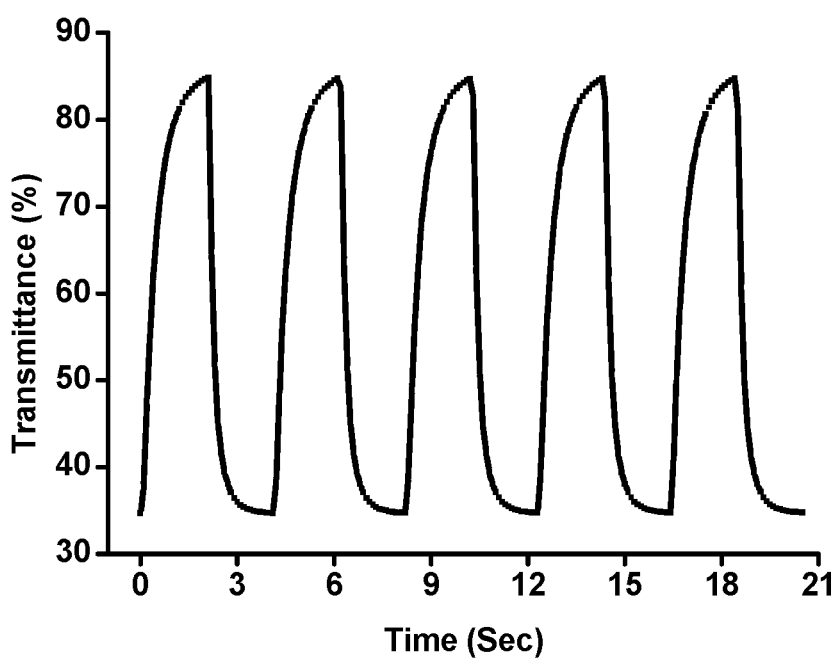
FIGS. 36A-36B illustrate the spectroelectrochemical behavior of 0.5 cm×1 cm electrochromic device of an EC assembly composed of Compound 1DB M=Fe deposited on FTO/glass and a bare FTO/glass as the counter electrode.
Figure 36B:
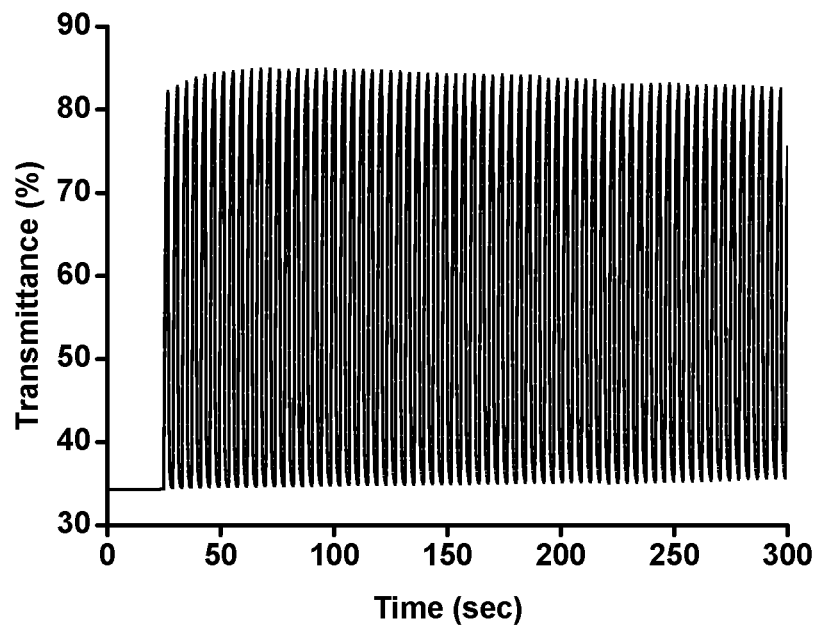

The electrochemical and spectroelectrochemical properties of the film were evaluated using three-electrode cell configuration consisting of the modified ITO/PET substrate, Pt wire and Ag/Ag$^+$ wire as working, counter, and reference electrodes, respectively. The film was held both in not-bent and in bent configurations. CV measurements of the non-bent film reveal reversible redox processes of the Fe$^{-2}$/Fe$^{+3}$ pair (FIG. 32). Moreover, the film was cycled for 1500 redox cycles, with a minor decrease in the current (<2%) (FIGS. 33A-33B).

1.5 Solid State/Laminated Electro Chromic Devices

In some embodiments, for real time applications, EC films should be incorporated in a solid configuration. The basic structure of an electro-chromic device (ECD) consists of two-EC layers separated by an electrolyte layer. ECDs can be divided into two main categories: All-solid state ECDs, where the electrolyte is a solid organic or inorganic layer (not liquid or gel); and laminated ECDs, where the electrolyte is a liquid gel. Laminated ECD's are also considered as 'solid state systems' in some embodiments. Many parameters can affect the performances of the device: conductivity of the electrodes, spacer type and dimensions, electrolyte type and composition and device packing and sealing. As a result of the many affecting parameters, long process of optimization is required in order to fabricate good performing device. Another main challenge is the life time of the device, as devices tend to degrade with increasing number of redox cycles.

In this example, ECDs were constructed by sandwiching [Compounds 1DB and 2DB|18|FTO/glass], and a bare FTO, with an electrolyte gel in between the two electrodes. The contacts were made of silver-paste or copper tape, and the spacing between the two electrodes was achieved by introducing 50 μm double-sided tape. The electrochemical behavior of the ECDs was analyzed using cyclic voltammetry and chronoamperometry.

The electrochemical and spectroelectrochemical properties of a device based on a film comprising Compound 1DB M=Fe were evaluated by applying double potential steps between (−2.5V) and (3V). The required potential window for such device operation is larger than the potential window required for a film in an electrolyte solution, due to the fact that in solid configuration, the viscosity of the (gel) electrolyte is higher, which results in higher resistance. SEC experiments were carried out by applying potential as a function of time, and recording the optical response at λ=571 nm (MLCT band peak) as the percentage of transmittance (% T) over time. The results reveal high contrast ratio of 50%. Moreover the film is able to retain 95% of its maximum contrast ratio even after 100 redox cycles.

Figure 37:
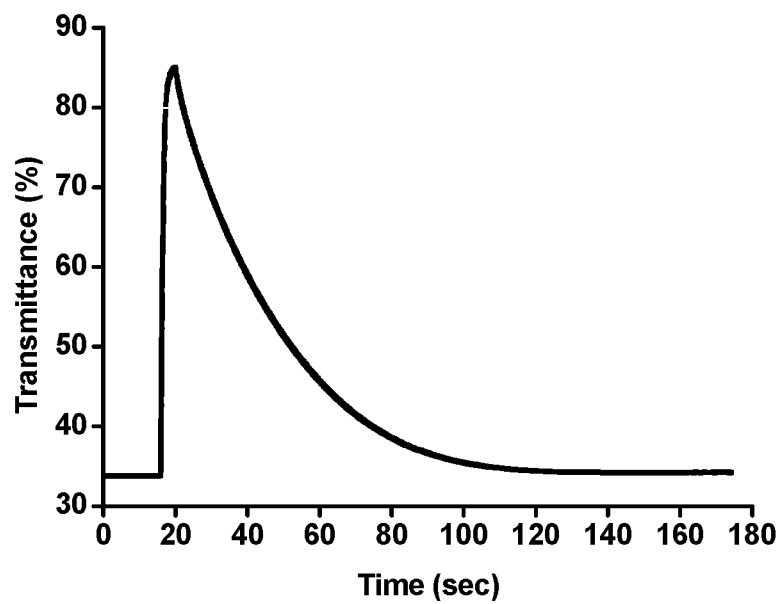
FIG. 37 illustrates the rate of decay of a rigid solid state EC device based of an EC assembly composed of Compound 1DB M=Fe. The kinetics of the redox process was tested by applying a suitable potential that resulted in bleaching of the device followed by shutting off the potential and opening the circuit, while monitoring the transmittance values of the device.
Figure 38A:
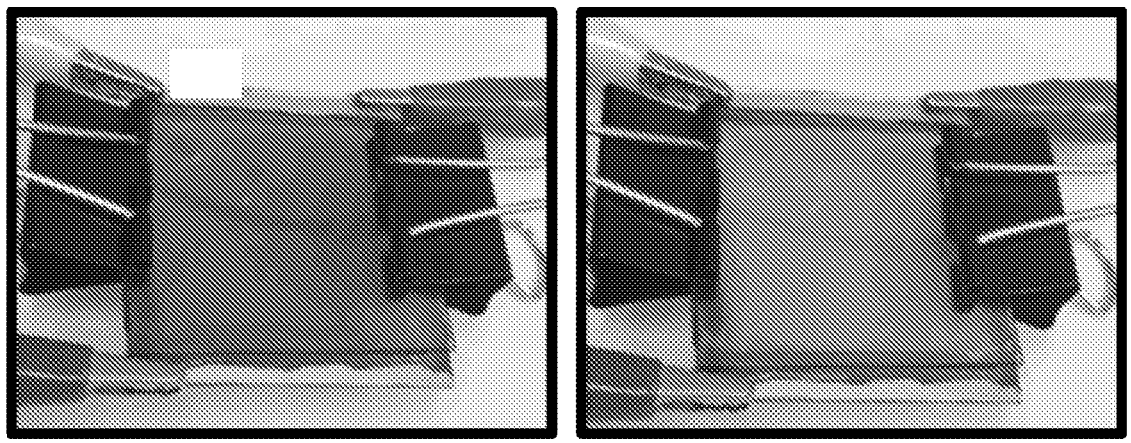
FIGS. 38A-38B Photographs of electrochromic devices, where the working electrode is [Compound 1DB M=Fe|18|FTO/glass] and the counter electrode is bare FTO substrate.
Figure 38B:
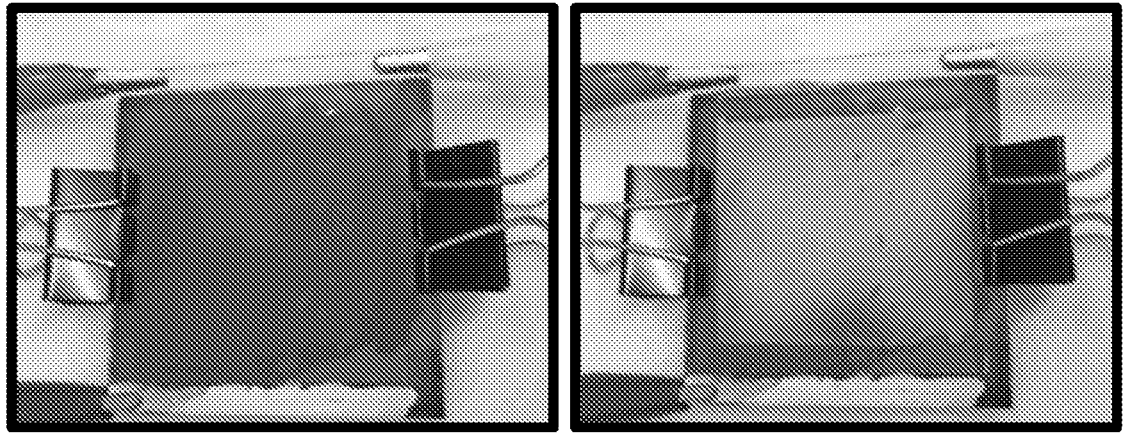

The kinetics of the redox process were tested in the following way: a suitable potential was applied (e.g. 3 V), which results in bleaching of the device. This was followed by shutting off the potential and opening the circuit. The device then started to return to its stable state, e.g. the colored, reduced state. From the exponential decay of the transmittance percentage (% T) with time, the rate of color change was calculated and found to be 0.032 sec$^{-1}$. (FIG. 37) Devices of different sizes were fabricated, using the same fabrication method. Larger switching times were required for full switching of larger devices. For example, FIGS. 38A-38B shows electrochromic devices of sizes (FIG. 38A) 4 cm×4 cm device; and (FIG. 38B) 6 cm×6 cm device, where the working electrode is [1DB M=Fe~18|FTO/glass], the counter electrode is bare FTO substrate and the electrolyte is a PMMA-based gel.

2. Materials and Methods

Solvents (AR grade) were purchased from Bio-Lab (Jerusalem), Frutarom (Haifa), or Mallinckrodt Baker (Phillipsburg, N.J.). Fluorine-doped-tin-oxide (FTO) coated glass substrates (6 cm×6 cm) and Indium-Tin Oxide (ITO) coated polyethylene terephthalate (PET) substrates were purchased from Xinyan Technology LTD (Hong-Kong, China). ITO coated glass substrate (6 cm×6 cm) were purchased from Delta Technologies (Loveland, Colo.). ITO and FTO substrates were cleaned by sonication in ethanol for 10 min, dried under N$_2$ stream and subsequently cleaned for 20 min with UV and ozone in a UVOCS cleaning system (Montgomery, Pa.). The slides were then rinsed with tetrahydrofuran (THF) and dried under N$_2$ stream, and 130° C. for 2 h. ITO coated PET substrates were cleaned by immersion in ethanol and acetone, followed by drying under N$_2$ stream. UV/vis spectra were recorded on a Cary 100 spectrophotometer (200-800 nm). The modified substrates were fixed in a Teflon holder and suitable clean substrates were used to compensate for the background absorption. All measurements were carried out at room temperature. Electrochemical measurements (cyclic voltammetry (CV), chronoamperometry (CA) and spectroelectrochemistry (SEC)) were carried out using a potentiostat (CHI660A or CHI1660E). The layer by layer deposition steps were performed using a Laurell spin-coater, model WS-400A-6NPP/LITE.

3. Multilayer Formation

A drop of 3.0 mM solution of PdCl$_2$(PhCN)$_2$ in THF was casted on FTO substrate, which was loaded on a spin coater stage. The substrate was spun at a speed of 500 rounds per minute (rpm) for 10 seconds, followed by spinning at a speed of 1000 rpm for 30 seconds. Subsequently, a drop of 0.6 mM solution of the EC compound (compounds 1DB M=Fe or 2DB M=Fe) in DCM/Methanol (1:1, v/v) was casted on the substrate, and was spun according to the same program. The substrate was immersed in acetone, for 1 min. and was dried under $N_2$ stream. An UV/vis absorbance spectrum was recorded after each deposition cycle.

4. Solid State Set Up (a) Preparation of the electrolyte gel: Polymethylmethacrylate (PMMA, 700 mg), trifluoromethylsulfonamide lithium salt (300 mg), dry acetonitrile (7.0 g, ~8.9 mL) and dry propylene carbonate (2.0 g, 1.7 mL), in 70:20:7:3 wt %, were added to a glass vessel in $N_2$-filled glovebox and stirred vigorously for 24 h, giving a homogeneous casting electrolyte solution. (b) Device fabrication: A frame of 50-100 μm double sided tape was cut and taped on the film slide, leaving an edge for silver paste or copper tape contacts. The edge of a bare FTO substrate was also covered with silver paste or copper tape. The bare substrate was placed on top of the film slide, in such a way that the two conducting faces of the substrates were facing each other. The sides of the device were sealed using epoxy glue or UV-curable glue. Finally, the electrolyte gel was injected using a syringe between the two substrates.

5. Electrochemistry in Solution

The electrochemical behavior of the film was tested in a solution of 0.1M tetrabutylammonium hexafluorophosphate ($TBAPF_6$) in ACN, by CV, CA and SEC. The measurements were performed in a three-electrode cell configuration consisting of (a) modified substrate (working electrode), (b) an Ag/Ag+ (reference electrode), and (c) a Pt wire (counter electrode).

6. Solid State Electrochemistry

The electrochemical behavior of the electrochromic device (ECD) was measured by CA and SEC, which were carried out by applying potential window between −2.5 V and 3 V, with a time gap of 4 seconds.

7. Additional Experiments on Mixed-Layer Deposition Systems

As discussed above, mixing of two components into one system can be obtained in various ways: alternating depositions of each compound, deposition in block configuration: a block of one compound followed by a block of the other compound. In block deposition, the sizes of blocks can be equal or can vary in favor of one compound over the other. Another deposition scheme comprises deposition of a mixed solution of the two compounds in equal or different concentrations. Such mixed-layer system was fabricated using the described fabrication method comprising LBL and spin-coating. The fabrication process includes alternating depositions of 3 mM solution of $PdCb(PhCN)_2$ in THF, and equimolar solution of the Fe-polypyridyl complexes 1DB M=Fe and 2DB M=Fe (0.3 mM each) in 1:1 DCM Methanol, using our spin coating LBL approach. These two subsequent steps (Pd linker and Fe-complexes) are referred to as a single deposition cycle. The films consisted of 18 deposition cycles, where after every deposition cycle, the modified substrates were washed using acetone, and were dried under $N_2$ stream. The fabrication process of the films was conducted at ambient conditions.

Figure 39A:
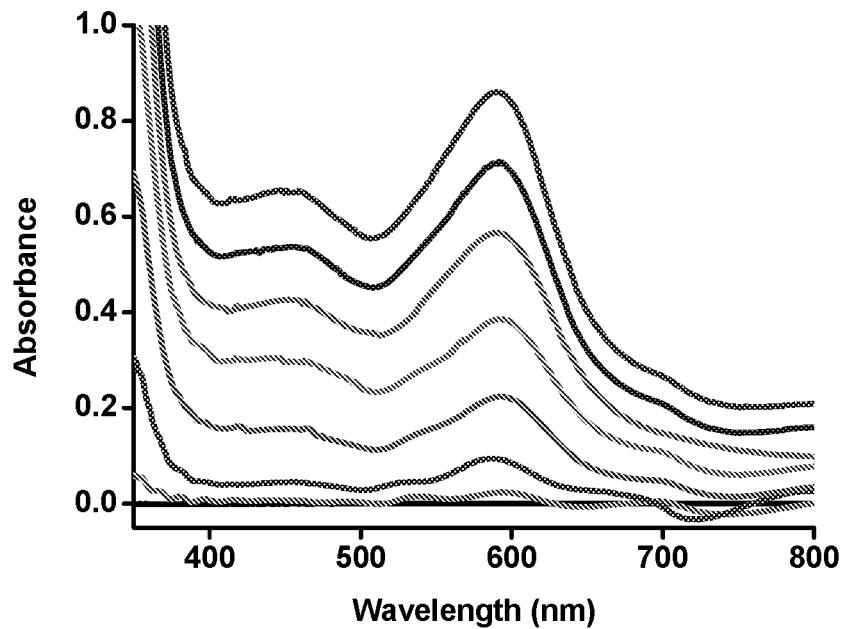
FIGS. 39A-39B illustrates the growth behavior of an assembly composed of equimolar mixture of Compound 1DB M=Fe and Compound 2DB M=Fe on ITO/PET.
Figure 39B:
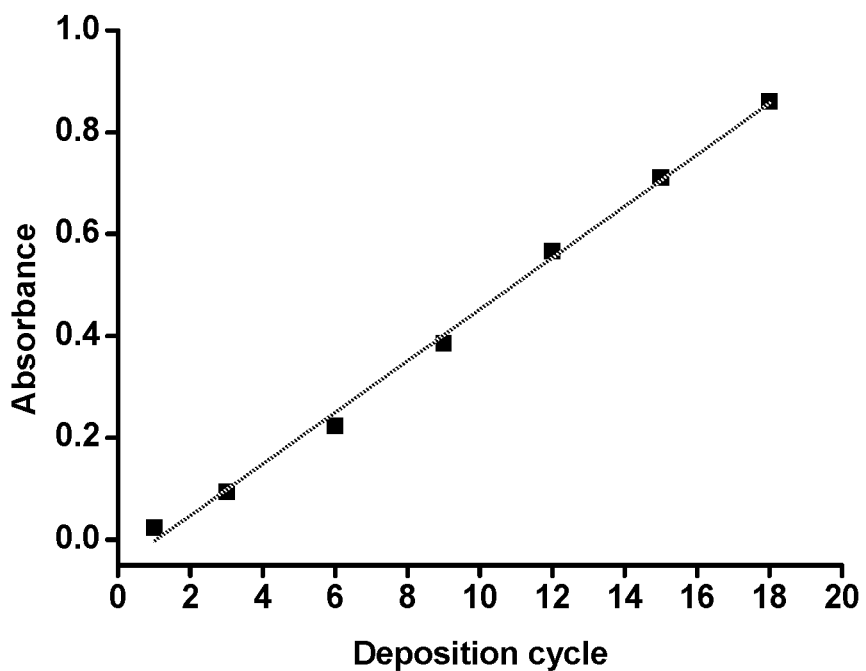

Compound 1DB M=Fe has a characteristic MLCT band at λ=578 nm, while Compound 2DB M=Fe has two distinct MLCT bands at λ=452 nm and λ=598 nm. The combination of these two compounds gives rise to a MLCT band at λ=589 nm, that is increasing linearly as the number of deposition cycles increases (FIGS. 39A-39B).

Electrochemistry in Solution

Figure 40:
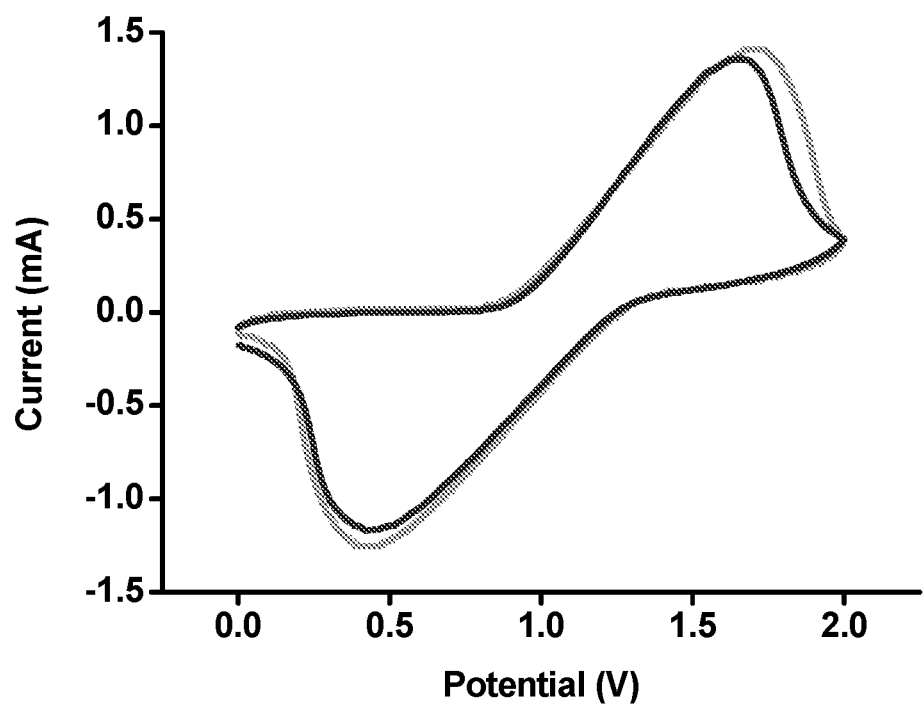
FIG. 40 illustrates the cyclic voltammetry of an assembly composed of equimolar mixture of Compound 1DB M=Fe and Compound 2DB M=Fe on 6 cm×2 cm ITO/PET substrate. The orange curve indicates the CV of the assembly before any bending forces were applied, and the green curve indicates the CV of the assembly when it is held bent with a radius of curvature of 2.5 cm.
Figure 41:
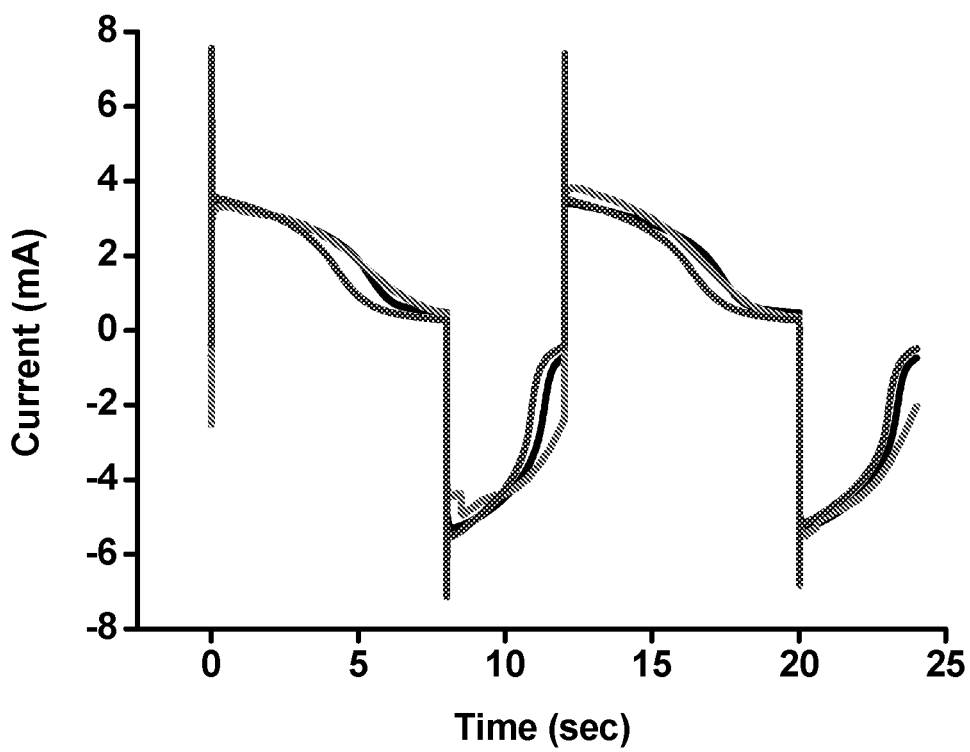
FIG. 41 illustrates the chronoamperometry (CA) of an assembly composed of equimolar mixture of Compound 1DB M-Fe and Compound 2DB M=Fe on 6 cm×1 cm ITO/PET substrate, with resistivity of 60 ohm/sq. The CA was recorded when the assembly was held at the following positions: (blue) upright (red) bent at a radius of curvature of 2.5 cm. (black) upright after being bent for 10 s at a radius of curvature of 2.5 cm.

The electrochemical properties of these systems deposited on ITO/PET 60 ohm/sq were evaluated using three-electrode cell configuration consisting of the modified ITO/PET substrate as working electrode, Pt wire and Ag/Ag+ wire as counter, and reference electrodes respectively. Chronoamperometry and cyclic voltammetry were measured in order to test the film's durability to bending: The film was measured when it was upright, then it was measured while bent in a curvature radius of 2.5 cm, and finally again when it was back upright. The electrochemical switching was performed by applying (−0.5 V) for 4 seconds and (2 V) for 8 seconds for few cycles, while the CV was recorded at a scan rate of 0.05 V/sec, at a potential window of 0-2 V. The results show no significant difference when the film was measured before or after the bending, as FIGS. 40 and 41 demonstrates.

Figure 42:
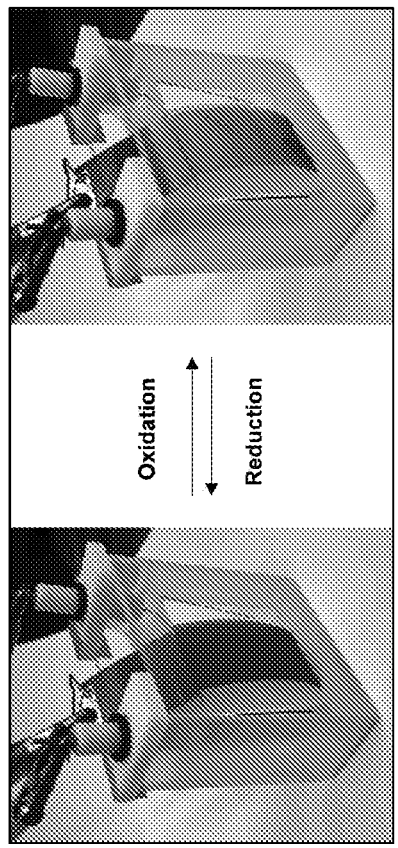
FIG. 42 illustrates photographs of the colored and the bleached states of an assembly composed of equimolar mixture of Compound 1DB M=Fe and Compound 2DB M=Fe on 6 cm×1 cm ITO/PET substrate, with resistivity of 60 ohm/sq. The photographs were taken when the assembly was held at the following positions: upright (left) and bent at a radius of curvature of 2.5 cm (right).
Figure 42:
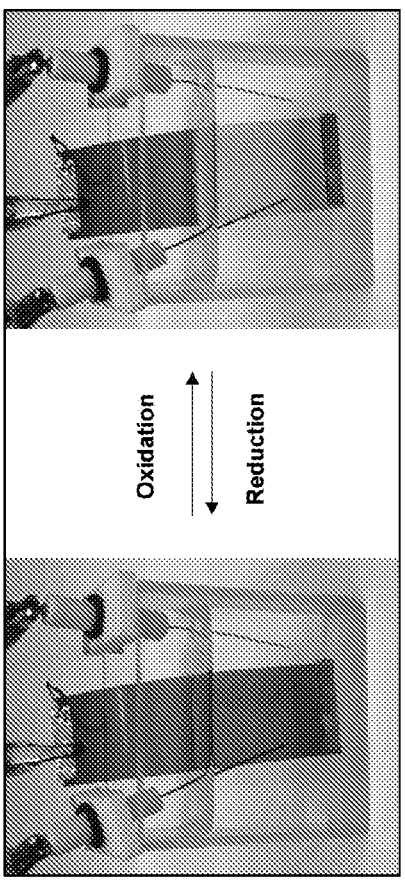
Figure 43:
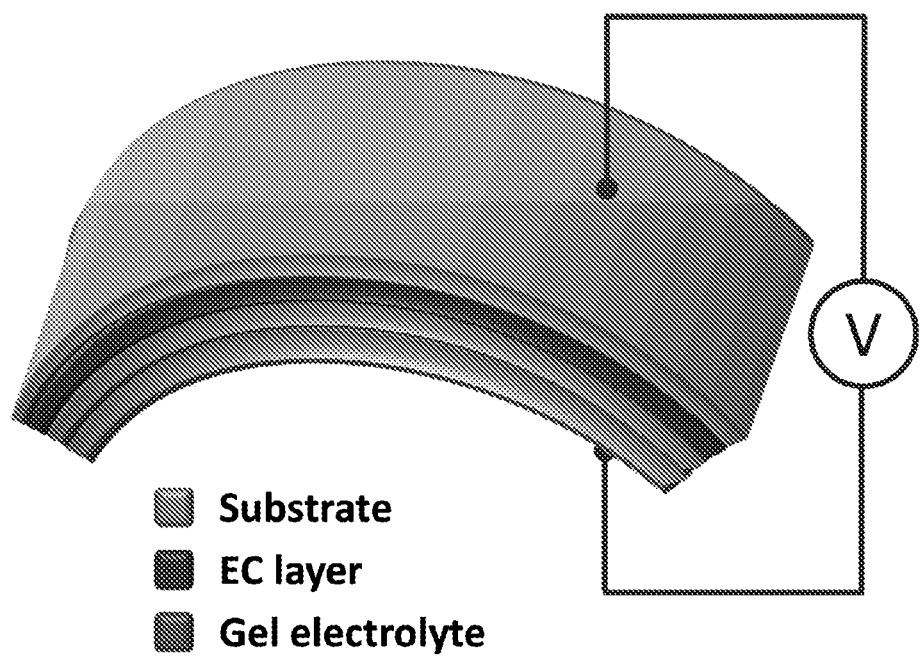
FIG. 43 is a schematic representation of a flexible electrochromic device, where the substrates are transparent conducting electrodes and the spacer is 3M 9088 double sided tape.

The Photographs in FIG. 42 show the colored and the bleached states of such 1 cm×6 cm device, wherein (left) the film is upright, and (right) the film is bent at a curvature radius of 2.5 cm. The electrochemical switching was performed by applying −0.5 V for 4 seconds and 2 V for 8 seconds for few cycles. FIG. 43 is a schematic representation of a flexible electrochromic device. The substrates are transparent conducting electrodes and the spacer is 3M 9088 double sided tape.

Figure 44:
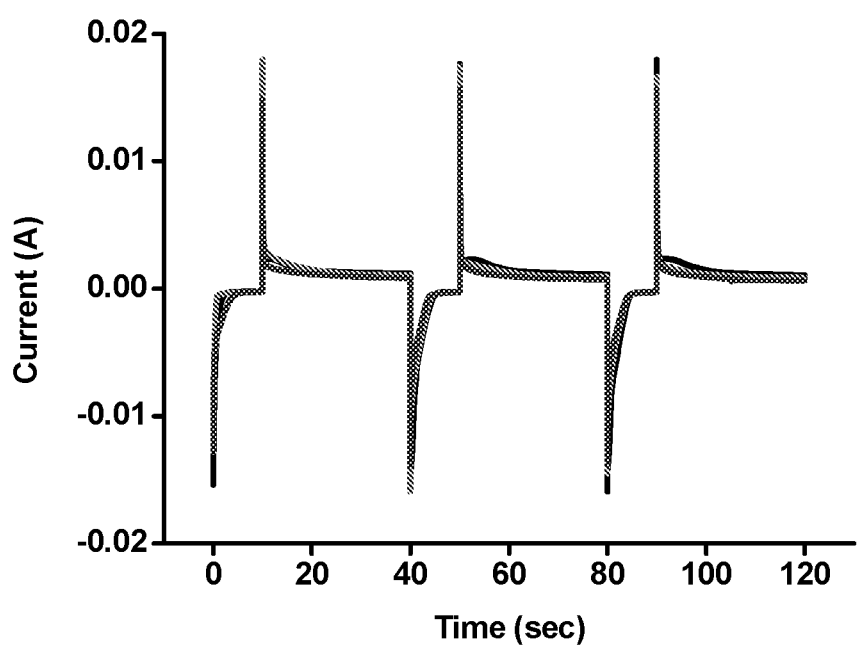
FIG. 44 illustrates the electrochemical behavior of 6 cm×1 cm electrochromic device, where the working electrode is an assembly composed of equimolar mixture of Compound 1DB M-Fe and Compound 2DB M-Fe on ITO/PET 60 ohm/sq. (after 18 deposition cycles) and the counter electrode is a bare 60 ohm/sq. ITO/PET. The CA was recorded when the assembly was held at the following positions: (blue) upright (red) bent at a radius of curvature of 2.5 cm. (black) upright after being bent for 10 s at a radius of curvature of 2.5 cm.

ECDs were constructed by sandwiching such mixed-layer Fe-complexed films (1DB and 2DB|18|ITO/PET 60 ohm/sq) with a bare 60 ohm/sq ITO/PET. An electrolyte (Li salt in propylene carbonate, with or without PMMA as a plasticizer) or an ionic liquid was placed in between the two electrodes. The contacts were made of copper tape or silver paste, and the spacing between the two electrodes was achieved by introducing 50-200 μm double-sided tape. Chronoamperometry was measured in order to test the device's durability to bending: the device was measured when it was upright, then it was measured while bent in a curvature radius of 2.5 cm, and finally again when it was back upright. The electrochemical switching was performed by applying −2.5 V for 10 seconds and 3 V for 30 seconds for few cycles. The results show no significant difference when the device was measured before or after the bending, as FIG. 44 demonstrates.

Figure 45:
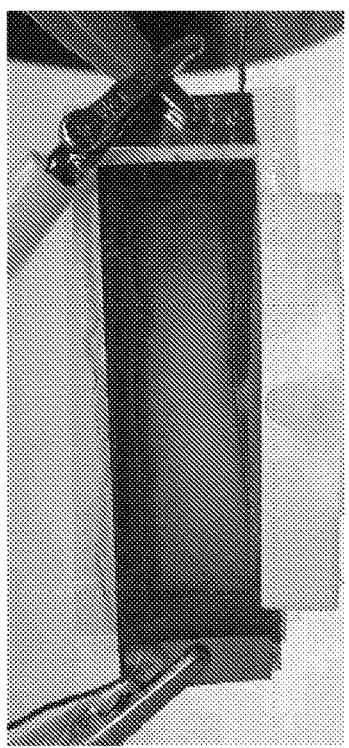
FIG. 45 shows photographs of the colored (left) and the bleached (right) of a flexible electrochromic device, where the working electrode is an assembly composed of equimolar mixture of Compound 1DB M=Fe and Compound 2DB M=Fe on ITO/PET 60 ohm/sq. (after 18 deposition cycles) and the counter electrode is a bare 60 ohm/sq. ITO/PET.
Figure 45:
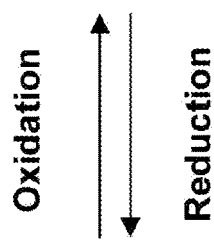
Figure 45:
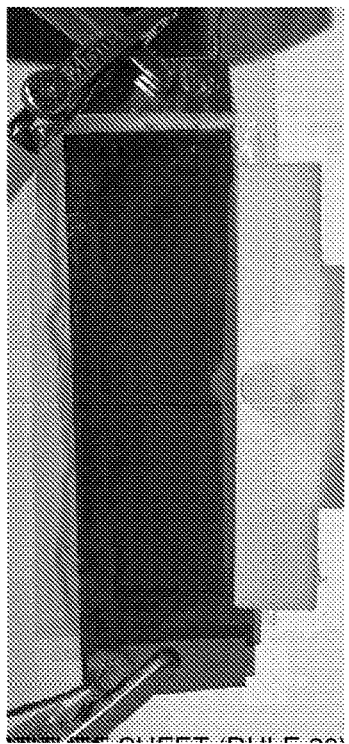

The Photographs shown in FIG. 45 of the colored (left) and the bleached (right) of a flexible electrochromic device, where the working electrode is a film comprising mixed layers of (Fe-complexes 1DB and 2DB|18|ITOTET 60 ohm/sq.) and the counter electrode is bare 60 ohm/sq. ITO/PET substrate. The electrochemical switching was performed by applying −2.5 V for 10 seconds and 3 V for 30 seconds.

Figure 46:
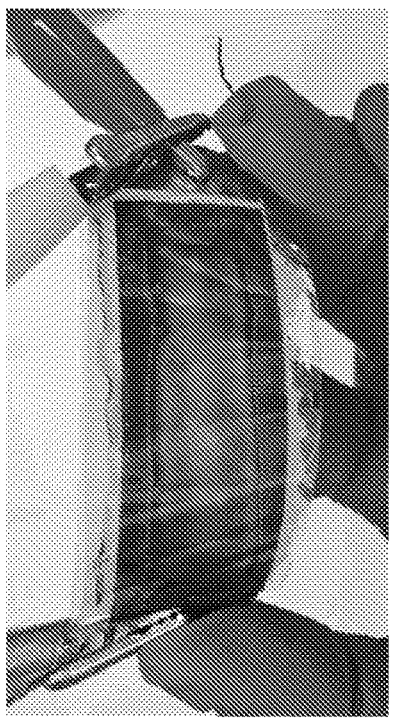
FIG. 46 shows photographs of the colored (left) and the bleached (right) of a flexible electrochromic device, where the working electrode is an assembly composed of equimolar mixture of Compound 1DB M=Fe and Compound 2DB M=Fe on ITO/PET 60 ohm/sq. (after 18 deposition cycles) and the counter electrode is a bare 60 ohm/sq. ITO/PET. The device undergoes switching when held bent.
Figure 46:
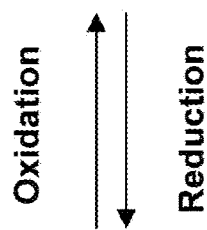
Figure 46:

The Photographs shown in FIG. 46 of the colored (left) and the bleached (right) of a flexible electrochromic device, where the working electrode is a film comprising mixed layers of (Fe-complexes 1DB and 2DB|18|ITO/PET 60 ohm/sq.) and the counter electrode is bare 60 ohm/sq. ITO/PET substrate. The electrochemical switching was performed by applying −2.5 V for 10 seconds and 3 V for 30 seconds, when the device was being held at a curvature radius of 2.5 cm.

8. Study of Additional Polypyridyl Complexes

Figure 47A:
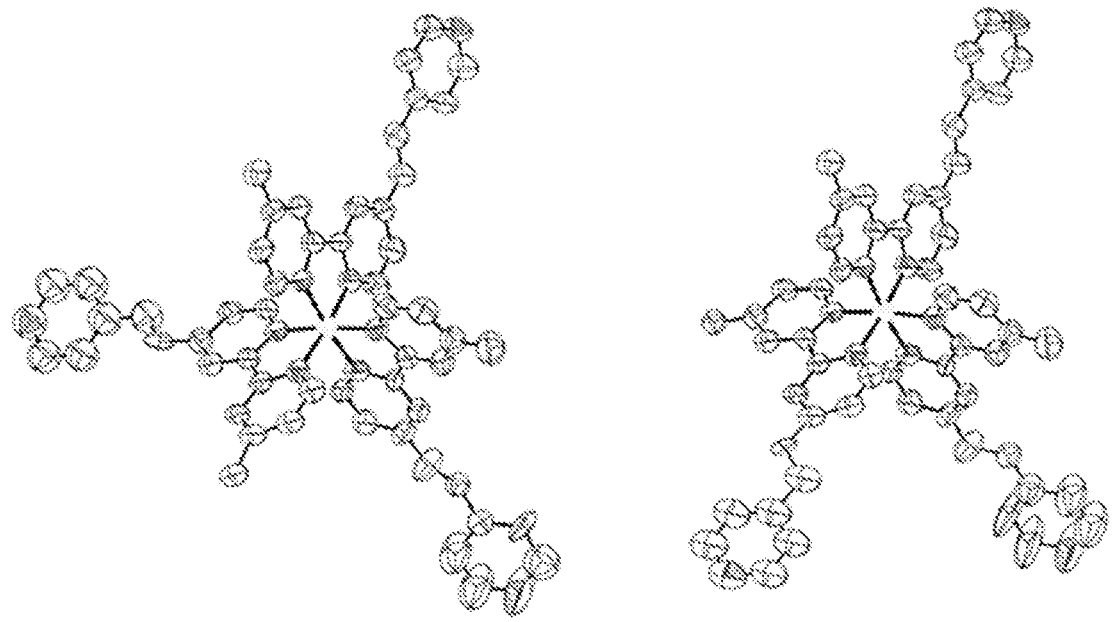
FIGS. 47A-47B shows crystal structures of complexes 1DB M=Fe and 2DB M=Fe.
Figure 47B:
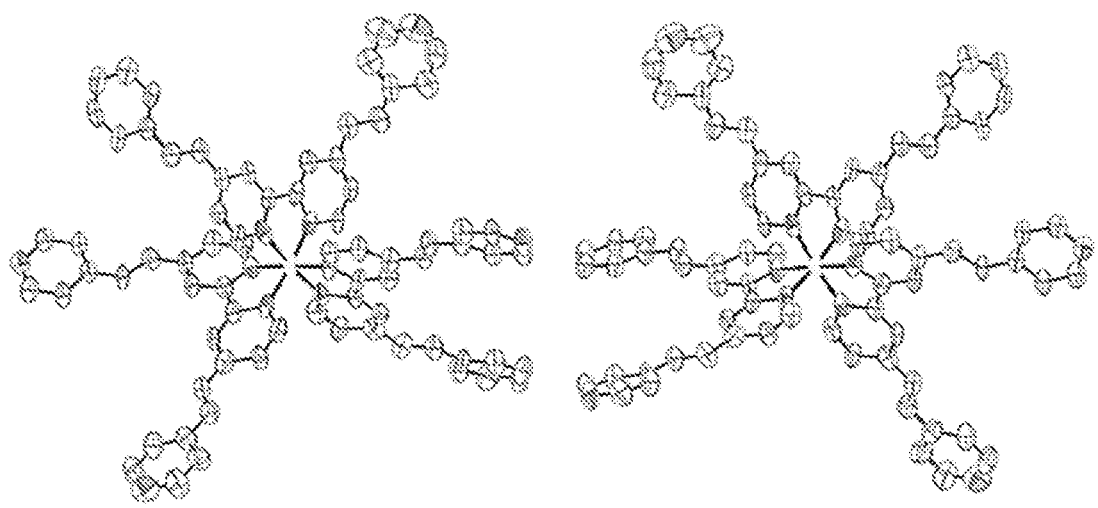
Figure 48:
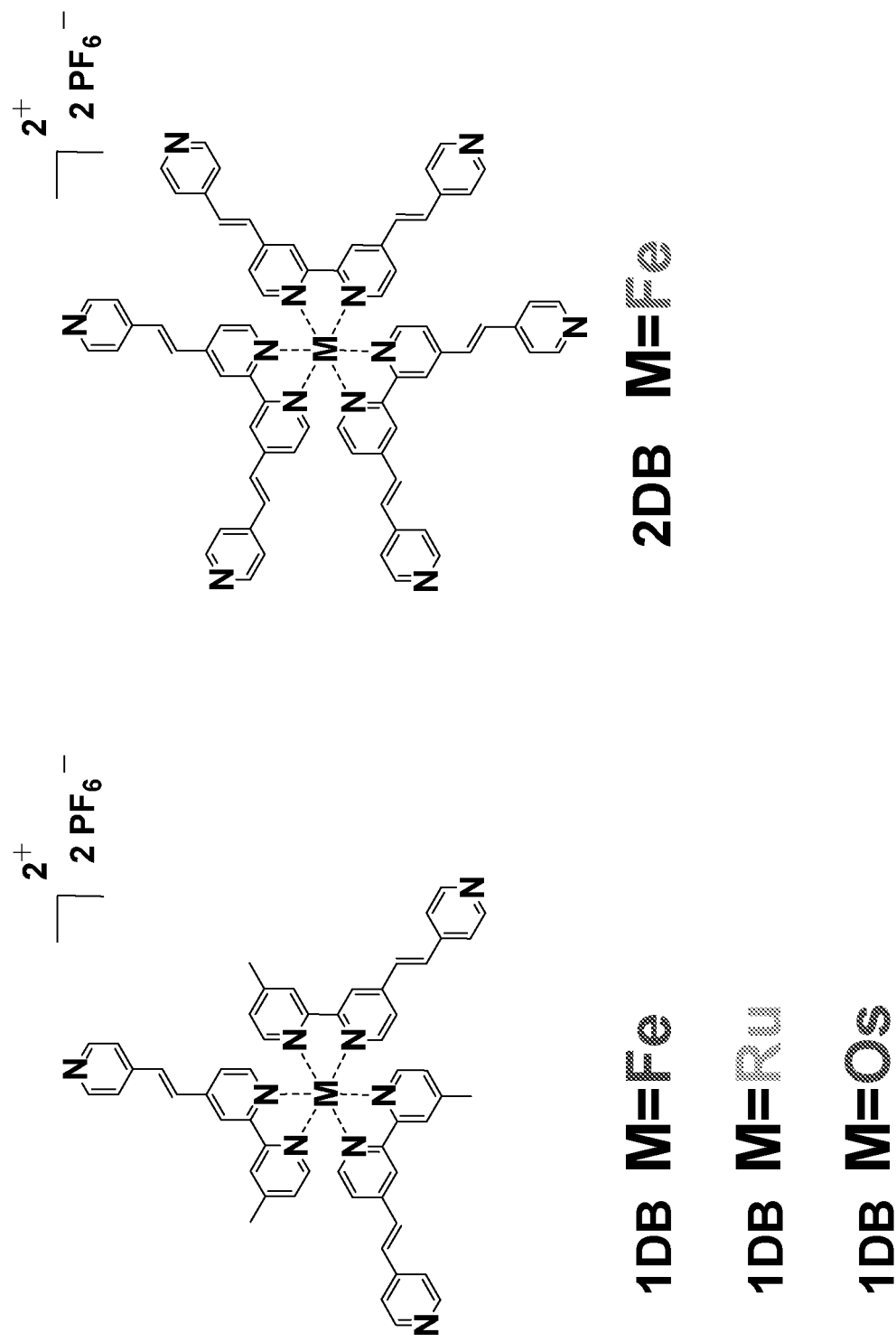
FIG. 48 shows molecular structures of polypyridyl complexes 1DB-2DB with various metal ions (Fe, Ru and Os as shown in the figure).
Figure 49A:
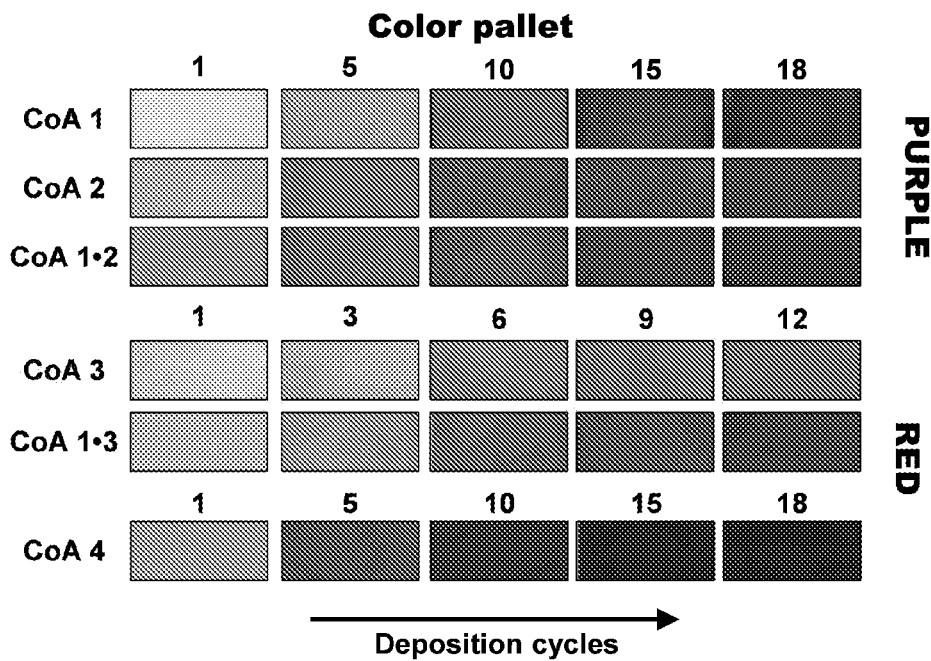
FIG. 49A-49B Color diversity.
Figure 49B:
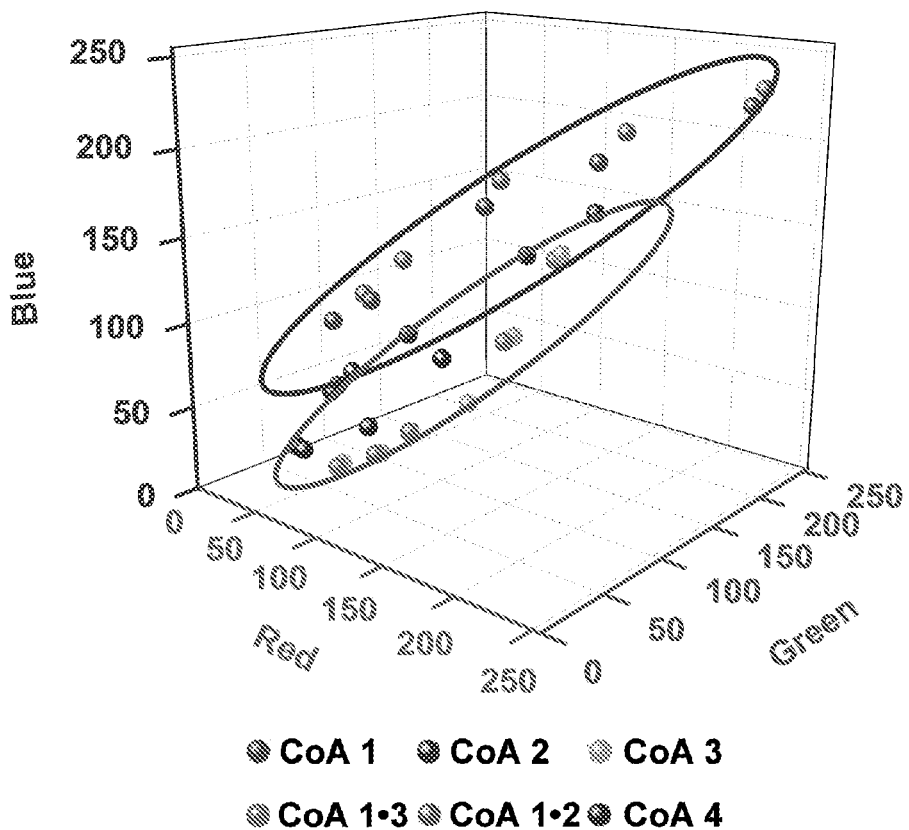
Figure 50A:
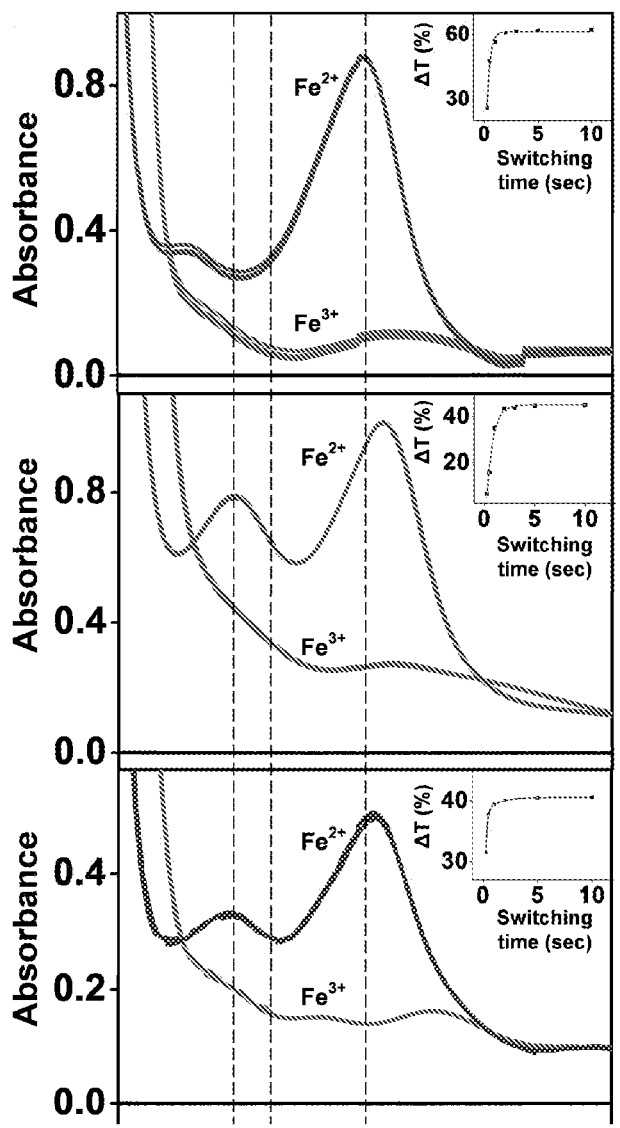
FIGS. 50A-50B Spectroelectrochemical (SEC) activity of the different assemblies on FTO/glass, in an electrolyte solution.
Figure 50B:
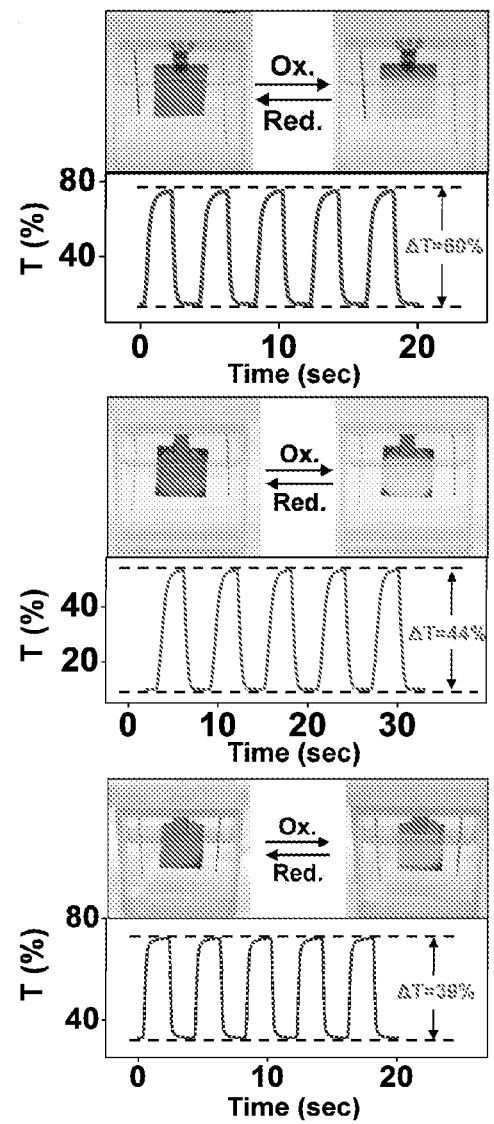

The crystal structure of complexes 1DB M=Fe and 2DB M=Fe were obtained, and the library of complexes has been expanded to include complexes 1DB M=Ru and 1DB M=Os. The crystal structure of complexes 1DB M=Fe and 2DB M=Fe is presented in FIGS. 47A-47B, and the additional complexes 1DB M=Ru and 1DB M=Os are presented in FIG. 48.

9. Patterned Electrochromic Surfaces

Figure 51:
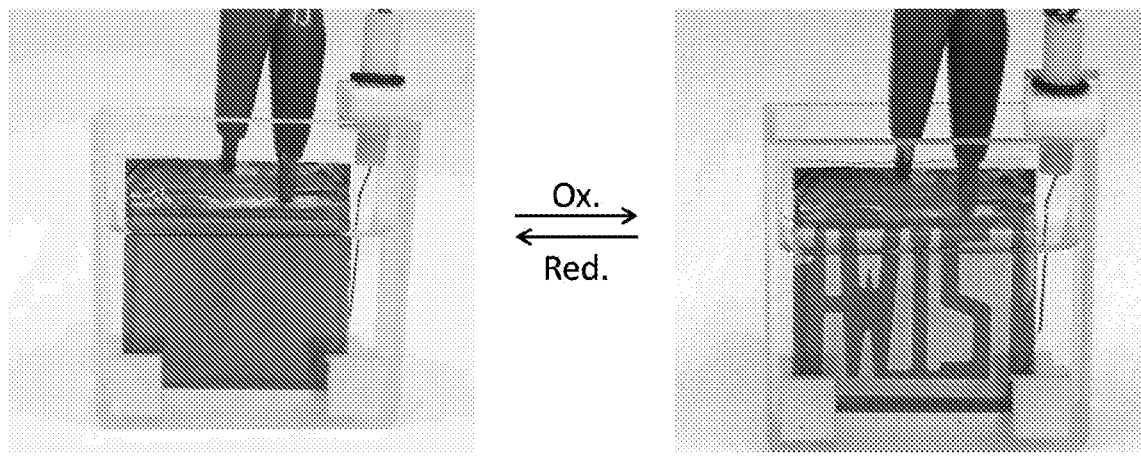
FIG. 51 Selective switching. The reduced (left) and oxidized (right) states of a patterned electrochromic surface of FTO/glass modified with complex 1DB M=Fe.

Selective switching of an electrochromic surface was demonstrated, by depositing the EC material on a glass substrate that was only partially coated by ITO according to a certain pattern. Using this technique, the selective switching was used for "writing" and "erasing" with response to an external potential (see FIG. 51).

10. Open Circuit Behavior

Figure 52:
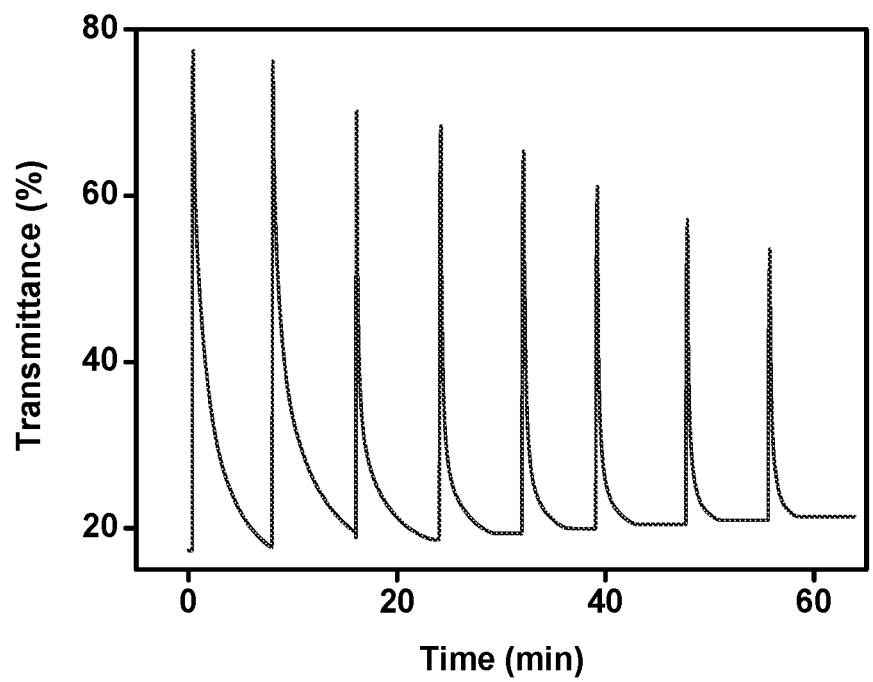
FIG. 52 Open circuit stability. Each pulse is generated by applying 1.6 V (oxidation potential) on a complex 1DB M=Fe-modified FTO/glass surface.

Open circuit stability is defined as the ability of a material to restore its original state after being subjected to an external stimulus. It was found that after being oxidized, and therefore bleached, the assemblies (the films, i.e. the EC materials on a substrate in embodiments as described herein above) were able to get reduced, and therefore colorful, spontaneously. The spectroelectrochemical profile of an open circuit experiment is presented in FIG. 52. The rate constant of the time that it takes to the assembly to restore its original state is extracted from the decaying exponents, and was found to be $2.25 \pm 0.37$ min$^{-1}$. An application to this characteristic behavior is the ability to use this spontaneous flow of electrons in order to satisfy an electrical consumer, e.g. LED. In order to satisfy an electrical consumer, e.g. LED, one needs to supply an electric current. When getting reduced under open circuit, the device may generate a spontaneous electric current that can be of further use.

11. Operation of Few Devices in Parallel

Figure 53:
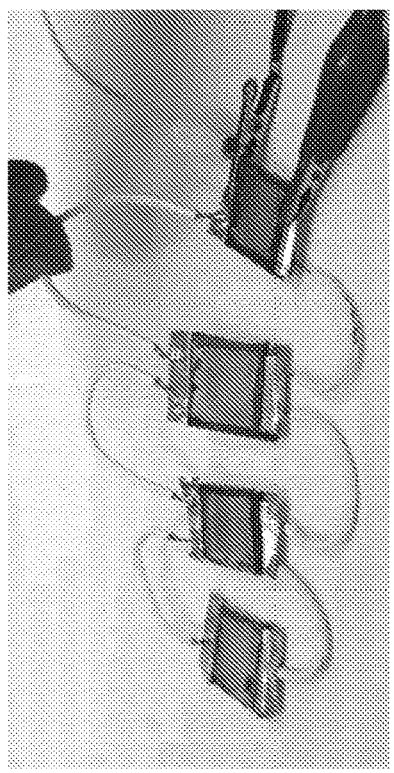
FIG. 53 Connecting devices in parallel. Left: the devices in its reduced state; Right: the devices in its oxidized state, after being subjected to the usual potential window for solid state devices.
Figure 53:
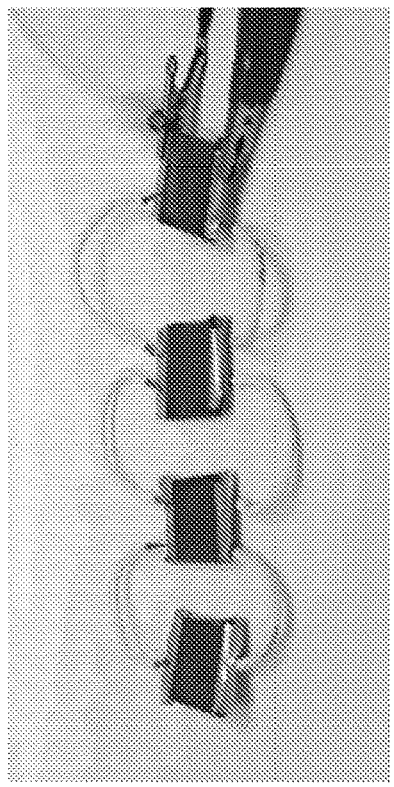

Few devices were connected in parallel. Such configuration allowed applying the same voltage to all the devices, while summing up the currents through each device. Also, connecting few devices together allowed increase of the active area, and by that overcoming resistivity issues which arises when it comes to larger surfaces (see FIG. 53).

12. Charge Trapping Systems

When combining two complexes with different redox potentials, the hierarchy of the assembly becomes an important parameter which determines the electrochemical properties of the assembly. In this example, dual-component systems were investigated: assembly of (1DB M=Fe and 1DB M=Ru) and assembly of (2DB M=Fe and 1DB M=Os). Table 2 presents the redox potentials of the different complexes, which allows the existence of three different outcomes depends on the hierarchy of the assemblies:

1) When the two components were mixed and deposited on the substrate randomly, both of the complexes should be electrochemically accessible and therefore active. This situation allows "three state system", as the system can exhibit one of three states: (a) the two components are reduced; (b) one is reduced and one is oxidized; (c) the two components are oxidized.

2) When the lower redox potential component is closer to the substrate than the higher redox potential component, oxidation of the top component was not possible, and therefore the system cannot reach a fully oxidized (fully bleached) state.

3) When the higher redox potential component is closer to the substrate than the lower redox potential component, reduction of the top component is not possible, which leads to charge trapping, as the top part is in its oxidized form, but won't be able to get reduced. This property of charge trapping can be used as new battery-like technology, as the trapped charge can be released on demand, by applying an external stimuli, e.g. light or over-potential. Every external stimulus has its own mechanism of operation. In general by applying a stimulus, one can overcome the energetic barrier that causes the charge trapping, and therefore the charge can be released.

TABLE 2

Redox potentials of complexes 1DBFe, 2DBFe, 1DBRu and 1DBOs.

| Complex | Metal center | Redox potential (V) |
|---|---|---|
| 1 DB M = Fe | Fe | 1.01 |
| 2 DB M = Fe | Fe | 1.01 |
| 1 DB M = Ru | Ru | 1.2 |
| 1 DB M = Os | Os | 0.8 |

Figure 54A:
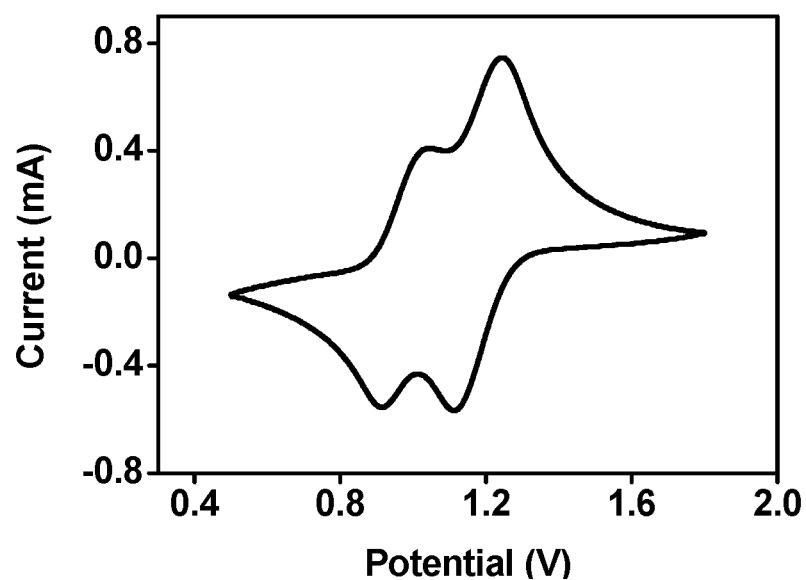
FIGS. 54A-54C Cyclic voltammograms of assembly made of compound 1DB M=Fe and compound 1DB M=Ru.
Figure 54B:
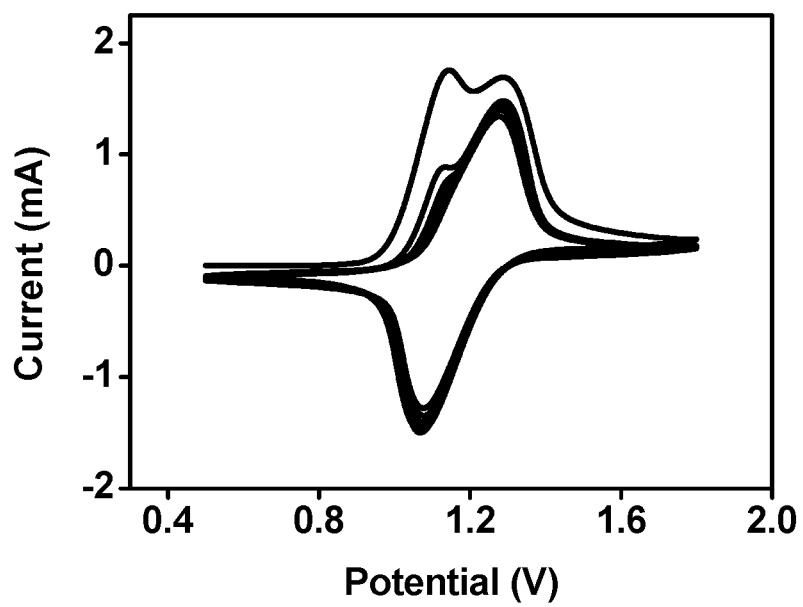
Figure 54C:
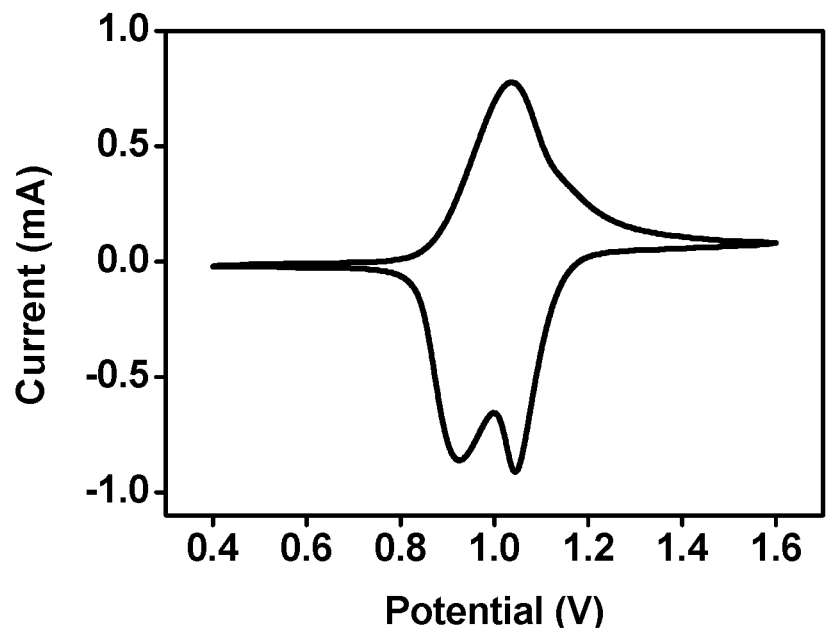

The three different hierarchies (1,2,3 above) were studied for both of the presented systems: assembly comprising 1DB M=Fe and 1DB M=Ru and assembly comprising 2DB M=Fe and 1DB M=Os. In the case of assembly 1DB M=Fe and 1DB M=Ru, the lower redox potential component is complex 1DB M=Fe (Fe-based complex with redox potential of 1 V), and the higher redox potential component is complex 1DB M=Ru (Ru-based complex with redox potential of 1.2 V), FIGS. 54A-54C present the cyclic voltammograms for assemblies composed of compounds 1DB M=Fe and 1DB M=Ru in each of the discussed hierarchies. In FIG. 54A, the redox waves of the two components are evident. In FIG. 54B, the phenomena of charge trapping is exhibited, as in the first redox cycle, the two oxidation peaks of the two components are present, however as the assembly is being repeatedly cycled, the top component cannot get reduced and therefore its oxidation wave is decreasing. In FIG. 54C, the reduction waves of the two components are evident, however, only the bottom component can get fully oxidized.

Figure 55A:
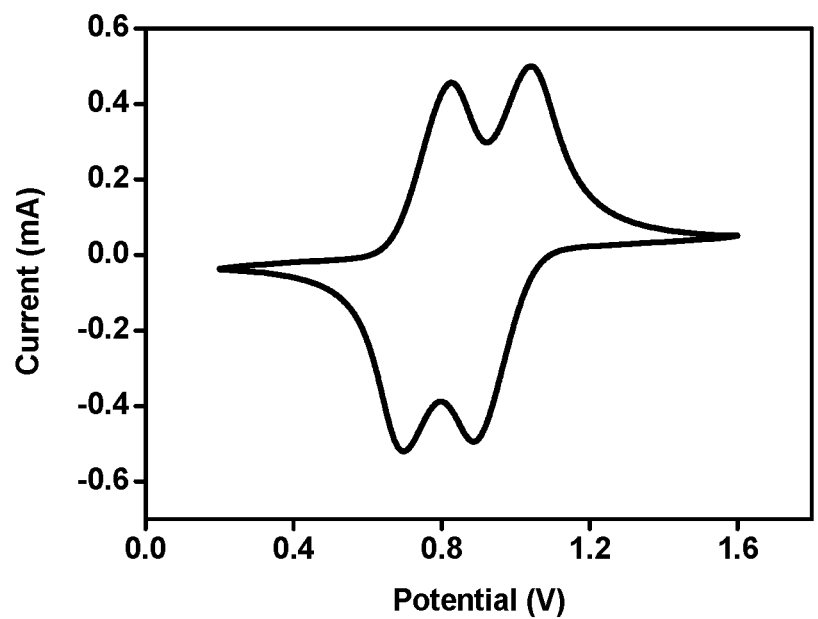
FIGS. 55A-55C Cyclic voltammograms of assembly made of compound 2DB M=Fe and compound 1DB M=Os.
Figure 55B:
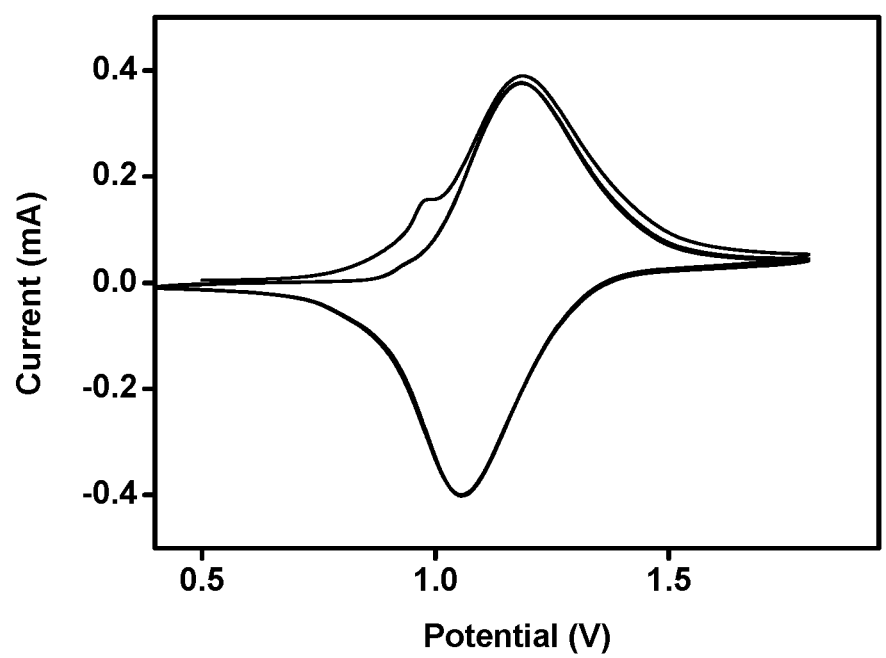
Figure 55C:
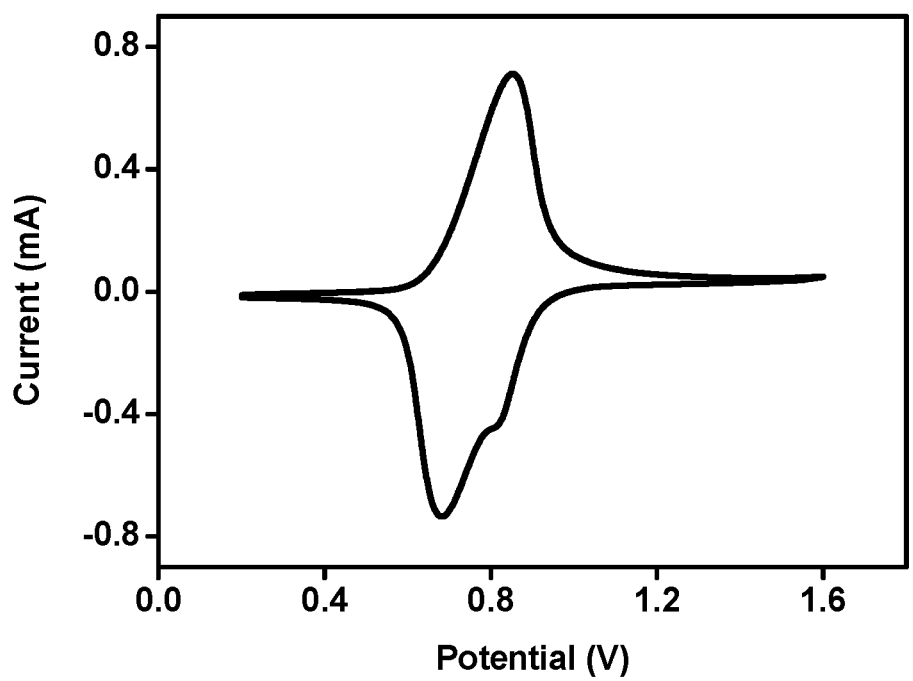

In the case of assembly 2DB M=Fe and 1DB M=Os, the lower redox potential component is complex 1DB M=Os (Os-based complex with redox potential of 0.8 V), and the higher redox potential component is complex 2DB M=Fe (Fe-based complex with redox potential of 1 V). FIGS. 55A-55C present the cyclic voltammograms for assemblies composed of compounds 2DB M=Fe and 1DB M=Os in each of the discussed hierarchies. The same characteristics that were observed in FIGS. 54A-54C, are now observed in FIGS. 55A-55C, where FIG. 55A representing the mixed hierarchy, FIG. 55B stands for the blocks hierarchy where complex 1DB M=Os is on top of complex 2DB M=Fe, and FIG. 55C represents the opposite blocks hierarchy, where complex 2DB M=Fe is on top of complex 1DB M=Os.

What is claimed is:

1. A method for making an electrochromic EC material comprising providing a substrate, applying at least one metal linker directly to the substrate, applying at least one metal-coordinated organic complex to form a layer, and repeating the applying steps to obtain a multiple layer EC material, wherein said substrate is not modified with a coupling layer.

2. The method of claim 1, wherein said metal-coordinated organic complex comprises at least one functional group, said functional group capable of binding to said metal linker.

3. The method of claim 2, wherein said binding comprises a coordination bond between said functional group and said metal linker.

4. The method of claim 1, wherein said metal-coordinated organic complex is polypyridyl complex.

5. The method of claim 4 wherein said polypyridyl complex comprises one isomer, or more isomers of the same compound, or a mixture of said isomers.

6. The method of claim 5, wherein said isomers are enantiomers and wherein said polypyridyl complex comprises one or two enantiomers of the same compound or a mixture of said one or two enantiomers.

7. The method according to claim 4, wherein the polypyridyl complex is represented by Formula I:

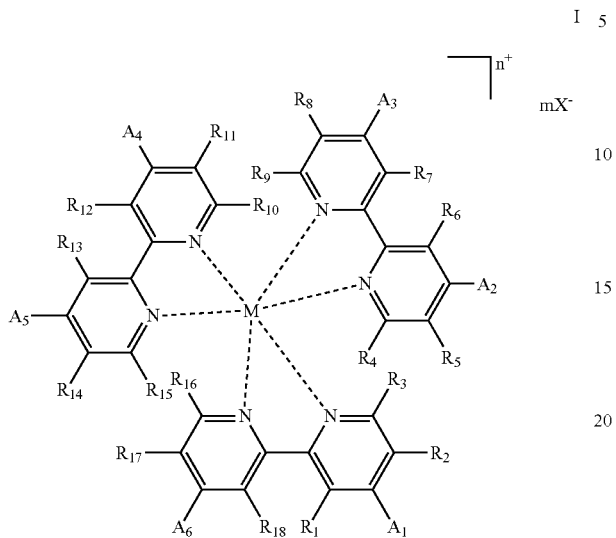

wherein

M is a transition metal selected from Mn, Fe, Co, Ni, Cu, Zn, Ti, C, Cr, Rh, or Ir;

n is the formal oxidation state of the transition metal, wherein n is 0-6;

X is a counter ion;

m is a number ranging from 0 to 6;

$R_1$ to $R_{18}$ each independently is selected from H, halogen, —OH, —$N_3$, —$NO_2$, —CN, —N($R_{20}$)$_2$, —CON($R_{20}$)$_2$, —COO$R_{20}$, —S$R_{20}$, —$SO_3H$, —CH=CH-pyridyl, —($C_1$-$C_{10}$)alkyl, —($C_2$-$C_{10}$)alkenyl, —($C_2$-$C_{10}$)alkynyl, —($C_1$-$C_{10}$)alkoxy, cycloalkyl, heterocycloalkyl, aryl, heteroaryl, wherein the ($C_1$-$C_{10}$)alkyl, ($C_2$-$C_{10}$)alkenyl, ($C_2$-$C_{10}$)alkynyl, cycloalkyl, heterocycloalkyl, aryl, or heteroaryl may optionally be substituted with halogen, —O$R_{20}$, —CO$R_{20}$, —COO$R_{20}$, —OCOO$R_{20}$, —OCON($R_{20}$)$_2$, —($C_1$-$C_8$)alkylene-COO$R_{20}$, —CN, —N($R_{20}$)$_2$, —$NO_2$, —S$R_{20}$, —($C_1$-$C_8$)alkyl, —O—($C_1$-$C_8$)alkyl, —CON($R_{20}$)$_2$, or —$SO_3H$;

$A_1$ to $A_6$ each independently is a group of Formula III, or of Formula IV, linked to the ring structure of the complex of general Formula I via $R_{19}$

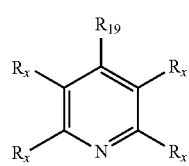

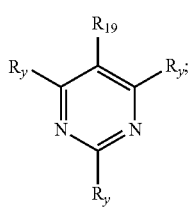

$R_{19}$ each independently is selected from a covalent bond, $H_2C$—$CH_2$, HC=CH, C≡C, N=N, HC=N, N=CH, $H_2C$—NH, HN—$CH_2$, —COO—, —CONH—, —CON(OH)—, —N$R_{20}$—, —Si($R_{20}$)$_2$—, an alkylene optionally interrupted by one or more heteroatoms selected from O, S, or N, phenylene, biphenylene, a peptide moiety consisting of 3 to 5 amino acid residues,

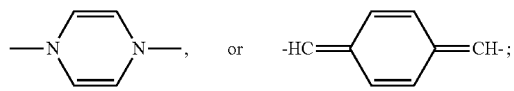

$R_x$ and $R_y$ each independently is selected from H, halogen, —OH, —$N_3$, —$NO_2$, —CN, —N($R_{20}$)$_2$, —CON($R_{20}$)$_2$, —COO$R_{20}$, —S$R_{20}$, —$SO_3H$, —CH=CH-pyridyl, —($C_1$-$C_{10}$)alkyl, —($C_2$-$C_{10}$)alkenyl, —($C_2$-$C_{10}$)alkynyl, —($C_1$-$C_{10}$)alkoxy, cycloalkyl, heterocycloalkyl, aryl, heteroaryl, protected carboxyl, or protected amino, wherein the ($C_1$-$C_{10}$)alkyl, ($C_2$-$C_{10}$)alkenyl, ($C_2$-$C_{10}$)alkynyl, cycloalkyl, heterocycloalkyl, aryl, or heteroaryl may optionally be substituted with halogen, —O$R_{20}$, —CO$R_{20}$, —COO$R_{20}$, —OCOO$R_{20}$, —OCON($R_{20}$)$_2$, —($C_1$-$C_8$)alkylene-COO$R_{20}$, —CN, —N($R_{20}$)$_2$, —$NO_2$, —S$R_{20}$, —($C_1$-$C_8$)alkyl, —O—($C_1$-$C_8$)alkyl, —CON($R_{20}$)$_2$, or $SO_3H$; and $R_{20}$ each independently is H, ($C_1$-$C_6$)alkyl, or aryl.

8. The method according to claim 4, wherein the polypyridyl complex is represented by Formula II:

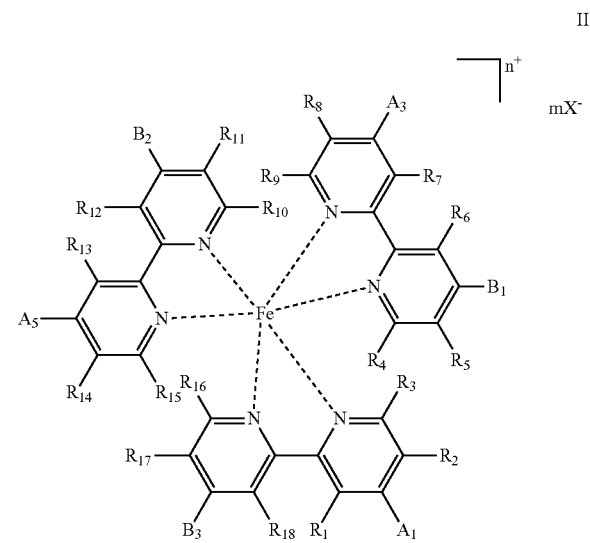

wherein n is the formal oxidation state of Fe, wherein n is 0-6;

X is a counter ion;

m is a number ranging from 0 to 6;

$R_1$ to $R_{18}$ each independently is selected from H, halogen, —OH, —$N_3$, —$NO_2$, —CN, —N($R_{20}$)$_2$, —CON($R_{20}$)$_2$, —COO$R_{20}$, —S$R_{20}$, —$SO_3H$, —CH=CH-pyridyl, —($C_1$-$C_{10}$)alkyl, —($C_2$-$C_{10}$)alkenyl, —($C_2$-$C_{10}$)alkynyl, —($C_1$-$C_{10}$)alkoxy, cycloalkyl, heterocycloalkyl, aryl, heteroaryl, wherein the ($C_1$-$C_{10}$)alkyl, ($C_2$-$C_{10}$)alkenyl, ($C_2$-$C_{10}$)alkynyl, cycloalkyl, heterocycloalkyl, aryl, or heteroaryl may optionally be substituted with halogen, —OR$_{20}$, —COR$_{20}$, —COOR$_{20}$, —OCOOR$_{20}$, —OCON(R$_{20}$)$_2$, —(C$_1$-C$_8$)alkylene-COOR$_{20}$, —CN, —N(R$_{20}$)$_2$, —NO$_2$, —SR$_{20}$, —(C$_1$-C$_8$)alkyl, —O—(C$_1$-C$_8$)alkyl, —CON(R$_{20}$)$_2$, or SO$_3$H;

A$_1$, A$_3$, and A$_5$ each independently is a group of Formula III, or of Formula IV, linked to the ring structure of the complex of general Formula II via R$_{19}$

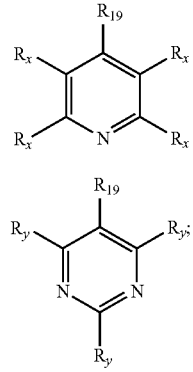

R$_{19}$ each independently is selected from a covalent bond, H$_2$C—CH$_2$, cis/tran HC=CH, C≡C, N=N, HC=N, N=CH, H$_2$C—NH, HN—CH$_2$, —COO—, —CONH—, —CON(OH)—, —NR$_{20}$—, —Si(R$_{20}$)$_2$—, an alkylene optionally interrupted by one or more heteroatoms selected from O, S, or N, phenylene, biphenylene, a peptide moiety consisting of 3 to 5 amino acid residues,

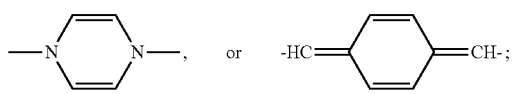

R$_x$ and R$_y$ each independently is selected from H, halogen, —OH, —N$_3$, —NO$_2$, —CN, —N(R$_{20}$)$_2$, —CON(R$_{20}$)$_2$, —COOR$_{20}$, —SR$_{20}$, —SO$_3$H, —CH=CH-pyridyl, —(C$_1$-C$_{10}$)alkyl, —(C$_2$-C$_{10}$)alkenyl, —(C$_2$-C$_{10}$)alkynyl, —(C$_1$-C$_{10}$)alkoxy, cycloalkyl, heterocycloalkyl, aryl, heteroaryl, protected carboxyl, or protected amino, wherein the (C$_1$-C$_{10}$)alkyl, (C$_2$-C$_{10}$)alkenyl, (C$_2$-C$_{10}$)alkynyl, cycloalkyl, heterocycloalkyl, aryl, or heteroaryl may optionally be substituted with halogen, —OR$_{20}$, —COR$_{20}$, —COOR$_{20}$, —OCOOR$_{20}$, —OCON(R$_{20}$)$_2$, —(C$_1$-C$_5$)alkylene-COOR$_{20}$, —CN, —N(R$_{20}$)$_2$, —NO$_2$, —SR$_{20}$, —(C$_1$-C$_5$)alkyl, —O—(C$_1$-C$_5$)alkyl, —CON(R$_{20}$)$_2$, or —SO$_3$H;

B$_1$ to B$_3$ each independently is selected from H, halogen, —OH, —N$_3$, —NO$_2$, —CN, —N(R$_{20}$)$_2$, —CON(R$_{20}$)$_2$, —COOR$_{20}$, —SR$_{20}$, —SO$_3$H, —CH=CH-pyridyl, —(C$_1$-C$_{10}$)alkyl, —(C$_2$-C$_{10}$)alkenyl, —(C$_2$-C$_{10}$)alkynyl, —(C$_1$-C$_{10}$)alkoxy, cycloalkyl, heterocycloalkyl, aryl, heteroaryl, protected carboxyl, or protected amino, wherein the (C$_1$-C$_{10}$)alkyl, (C$_2$-C$_{10}$)alkenyl, (C$_2$-C$_{10}$)alkynyl, cycloalkyl, heterocycloalkyl, aryl, or heteroaryl may optionally be substituted with halogen, —OR$_{20}$, —COR$_{20}$, —COOR$_{20}$, —OCOOR$_{20}$, —OCON(R$_{20}$)$_2$, —(C$_1$-C$_8$)alkylene-COOR$_{20}$, —CN, —N(R$_{20}$)$_2$, —NO$_2$, —SR$_{20}$, —(C$_1$-C$_8$)alkyl, —O—(C$_1$-C$_8$)alkyl, —CON(R$_{20}$)$_2$, or —SO$_3$H; and R$_{20}$ each independently is H, (C$_1$-C$_6$)alkyl, or aryl.

9. The method according to claim 4, wherein the polypyridyl complex is represented by one of the following formulas, or by a mixture of the following formulas, or by a combination of the following formulas with molecules with different metal centers or ligands:

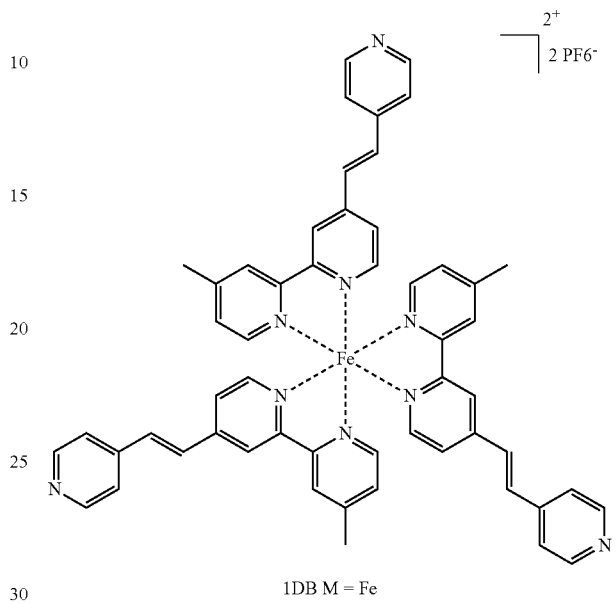

1DB M = Fe

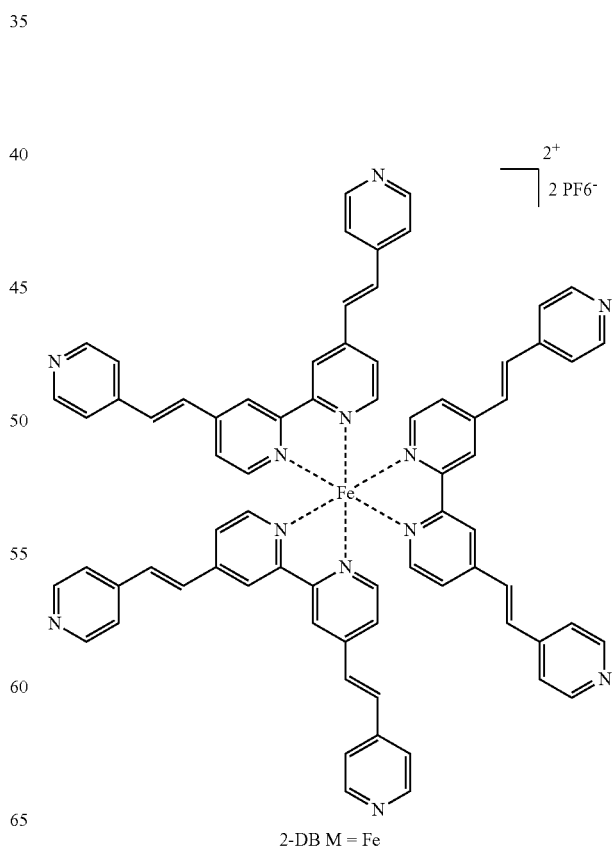

2-DB M = Fe

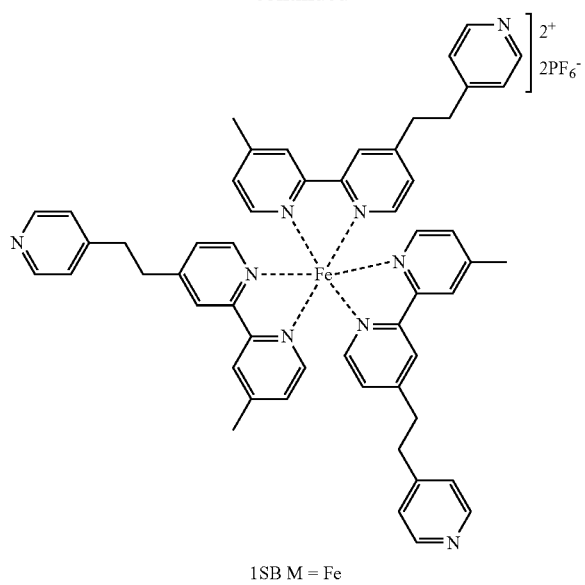

1SB M = Fe

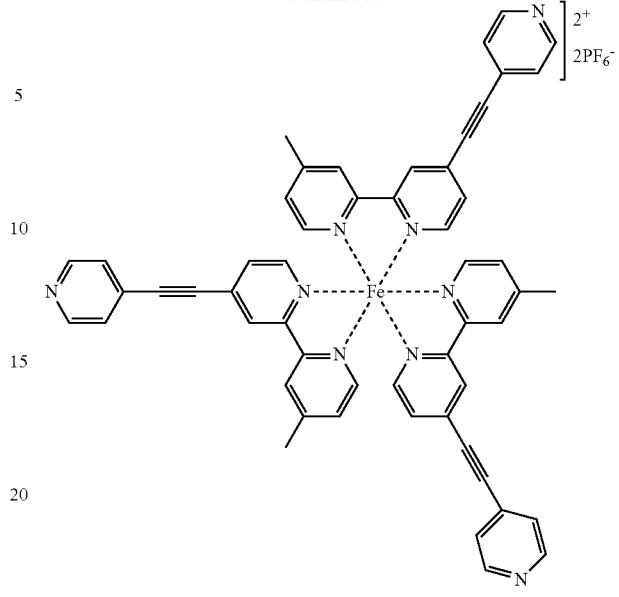

1-TB M = Fe

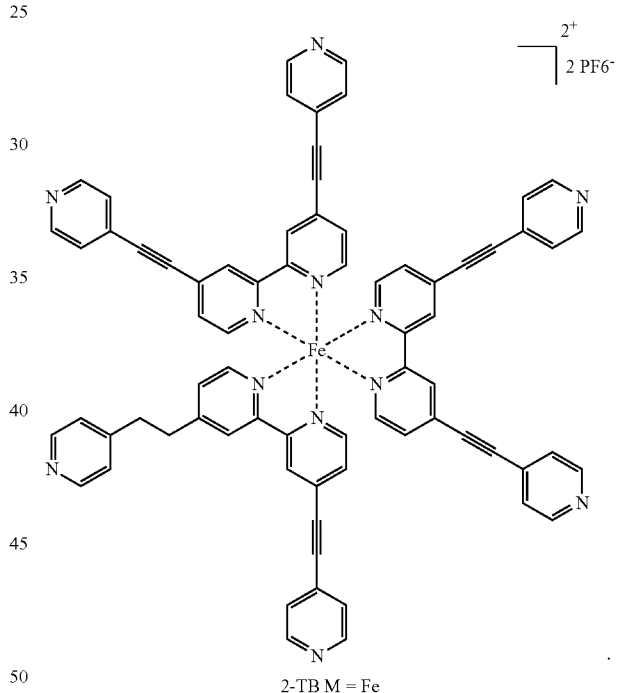

2-TB M = Fe

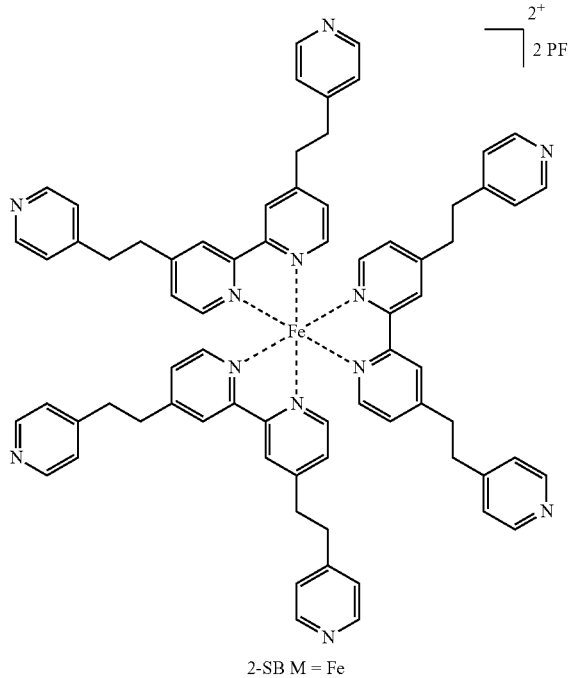

2-SB M = Fe

10. The method according to claim 4, wherein the polypyridyl complex is a mixture of polypyridyl complexes.

11. The method of claim 1, wherein said applying steps comprise roll-to-roll, spin coating, dip coating, spray coating, physical vapor deposition PVD, chemical vapor deposition CVD.

12. The method of claim 11, wherein said applying steps comprise spin coating.

13. The method according to claim 12, wherein the spin coating step to apply the metal linker has a first spin rate and a first spin time.

14. The method according to claim 13, wherein the first spin rate is from 100 to 2000 rpm.

15. The method according to claim 13, wherein the first spin time is from 0.3 sec to 60 sec.

16. The method according to claim 12, wherein the spin coating step to apply the metal linker has a second spin rate and a second spin time.

17. The method according to claim 16, wherein the second spin rate is from 200 to 3000 rpm.

18. The method according to claim 16, wherein the second spin time is from 1 second to 120 seconds.

19. The method according to claim 1, wherein both applying steps are repeated to obtain from 2 to 80 layers.

20. The method according to claim 1, wherein the colored state is the stable state, and the bleached state requires applied potential.

21. The method according to claim 1, wherein the metal linker is at least one selected from the group consisting of Zn, Os, Ru, Fe, Pt, Pd, Ni, Ir, Rh, Co, Cu, Re, Tc, Mn, V, Nb, Ta, Hf, Zr, Cr, Mo, W, Ti, Sc, Ag, Au, and Y.

22. The method according to claim 1, wherein the substrate is selected from the group consisting of indium tin oxide ITO, fluorine doped tin oxide FTO, ITO or FTO coated polyethylene terephthalate, ITO coated glass or quartz, and FTO coated glass or quartz.

23. The method according to claim 1, wherein the metal linker is a mixture of metal linkers.

24. The method of claim 1, wherein the step of applying at least one metal linker comprises applying the metal linker from a solution comprising said linker, and wherein the step of applying at least one metal-coordinated organic complex comprises applying the said metal-coordinated organic complex from a solution comprising the metal-coordinated organic complex, and wherein said solutions comprise a solvent, said solvent is selected from the group consisting of tetrahydrofuran THF, alcohols, ethers, esters, halogenated solvents, hydrocarbons, ketones, or a mixture thereof.

25. The method of claim 24, wherein the concentration of said linker in said solution and the concentration of said metal-coordinated organic complex in said solution ranges between 0.1 mM and 10 mM.

26. An EC material made by the method according to claim 1 having a transmittance difference between the oxidized and the reduced states of 10% and higher.

27. An EC material made by the method according to claim 1 having a transmittance difference between the oxidized and the reduced states of 64% and higher.

28. An EC material made by the method according to claim 1 able to retain at least 40% of its maximum contrast ratio after 50 switching cycles between oxidized and reduced states.

29. An EC material made by the method according to claim 1 able to retain at least 54% of its maximum contrast ratio after 1000 switching cycles between oxidized and reduced states.

30. The method of claim 1, wherein following the step of applying at least one metal-coordinated organic complex to form a layer and prior to the step of repeating the applying steps to obtain a multiple layer EC material, a step of washing the layer and drying the layer is performed.

31. The method according to claim 30, wherein the washing solvent is selected from the group consisting of alcohols, ethers, esters, halogenated solvents, hydrocarbons, ketones, or a mixture thereof.

32. A method for making an EC material comprising providing a substrate, applying at least one metal linker directly to the substrate by spin coating, applying at least one polypyridyl complex by spin coating to form a layer, and repeating the applying steps to obtain a multiple layer EC material, wherein the step of applying the metal linker has a first spin rate, a second spin rate, a first spin time and a second spin time, and wherein said substrate is not modified with a coupling layer.

33. The method according to claim 32, wherein the step of applying the polypyridyl complex has a first spin rate, a second spin rate, a first spin time and a second spin time.

34. The method according to claim 32, wherein the metal linker is applied as a metal complex.

35. The method of claim 32, wherein following the step of applying at least one polypyridyl complex by spin coating to form a layer and prior to the step of repeating the applying steps to obtain a multiple layer EC material, a step of washing the layer and drying the layer is performed.

36. The method of claim 35, wherein the washing solvent is selected from the group consisting of alcohols, ethers, esters, halogenated solvents, hydrocarbons, ketones, or a mixture thereof.

* * * * *